(12) United States Patent
Jain et al.

(10) Patent No.: US 11,763,919 B1
(45) Date of Patent: Sep. 19, 2023

(54) PLATFORM TO INCREASE PATIENT ENGAGEMENT IN CLINICAL TRIALS THROUGH SURVEYS PRESENTED ON MOBILE DEVICES

(71) Applicant: Vignet Incorporated, Fairfax, VA (US)

(72) Inventors: Praduman Jain, Fairfax, VA (US); Josh Schilling, Salem, OR (US); Yue Cao, Vienna, VA (US); Jack Burtch, Bristow, VA (US)

(73) Assignee: VigNet Incorporated, Fairfax, VA (US)

( * ) Notice: Subject to any disclaimer, the term of this patent is extended or adjusted under 35 U.S.C. 154(b) by 13 days.

(21) Appl. No.: 17/068,898

(22) Filed: Oct. 13, 2020

(51) Int. Cl.
G16H 10/20 (2018.01)
G16H 15/00 (2018.01)
G16H 50/30 (2018.01)
G06F 40/174 (2020.01)

(52) U.S. Cl.
CPC .......... *G16H 10/20* (2018.01); *G06F 40/174* (2020.01); *G16H 15/00* (2018.01); *G16H 50/30* (2018.01)

(58) Field of Classification Search
CPC ........ G16H 10/20; G16H 15/00; G16H 50/30; G06F 40/174
See application file for complete search history.

(56) References Cited

U.S. PATENT DOCUMENTS

| | | | |
|---|---|---|---|
| 5,545,186 A | 8/1996 | Olson et al. | |
| 5,547,878 A | 8/1996 | Kell | |
| 6,019,777 A | 2/2000 | Mackenzie | |
| 6,029,144 A | 2/2000 | Barrett et al. | |
| 6,029,195 A | 2/2000 | Herz | |
| 6,039,688 A | 3/2000 | Douglas et al. | |
| 6,260,022 B1 | 7/2001 | Brown | |
| 6,269,339 B1 | 7/2001 | Silver | |
| 6,321,172 B1 | 11/2001 | Jakob et al. | |
| 6,514,200 B1 | 2/2003 | Khouri | |

(Continued)

FOREIGN PATENT DOCUMENTS

| | | |
|---|---|---|
| CN | 106384321 | 2/2017 |
| EP | 1551282 | 7/2005 |

(Continued)

OTHER PUBLICATIONS

Burke et al., "Ecological Momentary Assessment in Behavioral Research: Addressing Technological and Human Participant Challenges", Journal of Medical Internet Research, Mar. 2017, 19(3):e77.

(Continued)

*Primary Examiner* — Hien L Duong
(74) *Attorney, Agent, or Firm* — Fish & Richardson P.C.

(57) ABSTRACT

Methods, systems, and apparatus, including computer programs encoded on a computer storage medium, for generating and delivering interactive modules. In some implementations, form data for an interactive module is accessed. Based on the form data, a first element from among the plurality of elements specified by the form data is presented. The system determines (i) a first score based on a user response to the first element and (ii) a cumulative score for the interactive module based at least in part on the first score. The system selects from among multiple options for adjusting presentation of the interactive module based on the scores.

20 Claims, 8 Drawing Sheets

(56) References Cited

U.S. PATENT DOCUMENTS

| | | |
|---|---|---|
| 6,663,846 B1 | 12/2003 | McCombs et al. |
| 6,828,992 B1 | 12/2004 | Freeman |
| 6,879,970 B2 | 4/2005 | Shiffman et al. |
| 6,904,408 B1 | 6/2005 | McCarthy |
| 7,054,782 B2 | 5/2006 | Hartlaub |
| 7,076,534 B1 | 7/2006 | Cleron et al. |
| 7,086,007 B1 | 8/2006 | Bushey |
| 7,225,414 B1 | 5/2007 | Sharma et al. |
| 7,251,609 B1 | 7/2007 | McAlindon et al. |
| 7,253,817 B1 | 8/2007 | Plantec et al. |
| 7,308,418 B2 | 12/2007 | Malek et al. |
| 7,330,717 B2 | 2/2008 | Gidron et al. |
| 7,383,283 B2 | 6/2008 | Carrabis |
| 7,415,447 B2 | 8/2008 | Shiffman et al. |
| 7,729,532 B2 | 6/2010 | Tedesco et al. |
| 7,752,059 B2 | 7/2010 | Sweeney et al. |
| 7,809,802 B2 | 10/2010 | Lerman et al. |
| 7,827,478 B2 | 11/2010 | Farr et al. |
| 7,827,495 B2 | 11/2010 | Bells et al. |
| 7,853,455 B2 | 12/2010 | Brown |
| 7,853,456 B2 | 12/2010 | Soto et al. |
| 7,953,613 B2 | 5/2011 | Gizewski |
| 7,966,282 B2 | 6/2011 | Pinckney et al. |
| 7,970,718 B2 | 6/2011 | Guyon et al. |
| 8,056,100 B2 | 11/2011 | Herz et al. |
| 8,065,180 B2 | 11/2011 | Hufford et al. |
| 8,078,956 B1 | 12/2011 | Feldman |
| 8,103,691 B2 | 1/2012 | Chunilal |
| 8,145,677 B2 | 3/2012 | Al-Shameri |
| 8,180,688 B1 | 5/2012 | Velummylum et al. |
| 8,239,918 B1 | 8/2012 | Cohen |
| 8,340,982 B2 | 12/2012 | Bjorner |
| 8,347,263 B1 | 1/2013 | Offer |
| 8,380,531 B2 | 2/2013 | Paty et al. |
| 8,433,605 B2 | 4/2013 | Hufford et al. |
| 8,533,013 B2 | 9/2013 | Cole |
| 8,533,029 B2 | 9/2013 | Hufford et al. |
| 8,566,175 B1 | 10/2013 | Nguyen et al. |
| 8,667,487 B1 | 3/2014 | Boodman et al. |
| 8,708,904 B2 | 4/2014 | Stivoric et al. |
| 8,775,415 B2 | 7/2014 | Jeon et al. |
| 8,799,666 B2 | 8/2014 | Kesanupalli et al. |
| 8,805,734 B2 | 8/2014 | Diana et al. |
| 8,805,759 B1 | 8/2014 | Cha et al. |
| 8,819,726 B2 | 8/2014 | Wetzer et al. |
| 8,850,304 B2 | 9/2014 | Ye et al. |
| 8,978,106 B2 | 3/2015 | Swamy et al. |
| 8,990,250 B1 | 3/2015 | Chowdry et al. |
| 8,997,038 B2 | 3/2015 | Becker |
| 9,049,259 B2 | 6/2015 | Rathod et al. |
| 9,134,964 B2 | 9/2015 | Hirsch |
| 9,135,445 B2 | 9/2015 | Kay et al. |
| 9,170,800 B2 | 10/2015 | Lang |
| 9,171,079 B2 | 10/2015 | Banka et al. |
| 9,183,365 B2 | 11/2015 | Taveau et al. |
| 9,208,692 B2 | 12/2015 | Considine et al. |
| 9,218,574 B2 | 12/2015 | Phillipps et al. |
| 9,256,698 B2 | 2/2016 | Vincent, III |
| 9,275,093 B2 | 3/2016 | Pandey et al. |
| 9,330,239 B2 | 5/2016 | Koduri et al. |
| 9,361,011 B1 | 6/2016 | Burns |
| 9,426,433 B1 | 8/2016 | Mazzarella |
| 9,461,972 B1 | 10/2016 | Mehta |
| 9,524,283 B2 * | 12/2016 | Folsom ............... G06F 40/143 |
| 9,542,649 B2 | 1/2017 | Su |
| 9,715,370 B2 | 7/2017 | Friedman |
| 9,753,618 B1 | 9/2017 | Jain et al. |
| 9,760,343 B2 | 9/2017 | Noens et al. |
| 9,824,606 B2 | 11/2017 | Basson et al. |
| 9,844,725 B1 | 12/2017 | Durkin et al. |
| 9,848,061 B1 | 12/2017 | Jain et al. |
| 9,858,063 B2 | 1/2018 | Jain et al. |
| 9,928,230 B1 | 3/2018 | Jain et al. |
| 9,940,454 B2 | 4/2018 | Richardson et al. |
| 9,942,358 B2 | 4/2018 | Babu et al. |
| 9,983,670 B2 | 5/2018 | Coleman et al. |
| 9,983,775 B2 | 5/2018 | Jain et al. |
| 10,002,199 B2 | 6/2018 | Matamala et al. |
| 10,068,270 B1 | 9/2018 | Kay et al. |
| 10,068,422 B2 | 9/2018 | Gadher et al. |
| 10,068,673 B2 | 9/2018 | Madan et al. |
| 10,069,934 B2 | 9/2018 | Jain et al. |
| 10,095,688 B1 | 10/2018 | Jain et al. |
| 10,152,761 B2 | 12/2018 | Kress et al. |
| 10,202,769 B2 | 2/2019 | Gya |
| 10,205,769 B2 | 2/2019 | Sehgal |
| 10,231,622 B2 | 3/2019 | Soyao et al. |
| 10,248,401 B1 | 4/2019 | Chen et al. |
| 10,304,000 B2 | 5/2019 | Birnbaum et al. |
| 10,311,478 B2 | 6/2019 | Dai et al. |
| 10,311,694 B2 | 6/2019 | Mcintosh et al. |
| 10,353,911 B2 | 7/2019 | Reynolds et al. |
| 10,402,748 B2 | 9/2019 | Virkar et al. |
| 10,410,626 B1 * | 9/2019 | Sherstinsky ........ H04M 3/5233 |
| 10,482,135 B2 | 11/2019 | Rychikhin |
| 10,521,557 B2 | 12/2019 | Jain et al. |
| 10,547,709 B2 | 1/2020 | Burningham et al. |
| 10,565,894 B1 | 2/2020 | Jain et al. |
| 10,616,138 B2 | 4/2020 | Garnal et al. |
| 10,705,816 B2 | 7/2020 | Jain et al. |
| 10,733,116 B2 | 8/2020 | Litichever et al. |
| 10,733,266 B2 | 8/2020 | Whitehurst |
| 10,749,775 B2 | 8/2020 | Holmes et al. |
| 10,756,957 B2 | 8/2020 | Jain et al. |
| 10,762,990 B1 | 9/2020 | Jain et al. |
| 10,775,974 B2 | 9/2020 | Schilling et al. |
| 10,902,946 B2 | 1/2021 | Narasimhan et al. |
| 10,915,306 B2 | 2/2021 | Jain |
| 10,938,651 B2 | 3/2021 | Jain et al. |
| 11,056,242 B1 | 7/2021 | Jain et al. |
| 11,061,798 B1 | 7/2021 | Jain et al. |
| 11,082,487 B1 | 8/2021 | Jain et al. |
| 11,102,304 B1 | 8/2021 | Jain et al. |
| 11,132,750 B2 * | 9/2021 | Malone ................. G16H 10/20 |
| 11,501,060 B1 | 11/2022 | Jain et al. |
| 11,507,737 B1 | 11/2022 | Jain et al. |
| 2001/0019338 A1 | 9/2001 | Roth |
| 2002/0022973 A1 | 2/2002 | Sun |
| 2002/0035486 A1 | 3/2002 | Huyn |
| 2002/0099570 A1 | 7/2002 | Knight |
| 2002/0143595 A1 | 10/2002 | Frank et al. |
| 2002/0157091 A1 | 10/2002 | DeMello et al. |
| 2003/0065669 A1 | 4/2003 | Kahn et al. |
| 2003/0078960 A1 | 4/2003 | Murren et al. |
| 2003/0130871 A1 | 7/2003 | Rao et al. |
| 2003/0229522 A1 | 12/2003 | Thompson et al. |
| 2004/0073868 A1 | 4/2004 | Easter et al. |
| 2004/0122715 A1 | 6/2004 | McAuliffe |
| 2004/0172447 A1 | 9/2004 | Miller |
| 2004/0210457 A1 | 10/2004 | Sameh |
| 2004/0216054 A1 | 10/2004 | Matthews |
| 2005/0050320 A1 | 3/2005 | Wassmann et al. |
| 2005/0055687 A1 | 3/2005 | Mayer |
| 2005/0071752 A1 | 3/2005 | Marlatt |
| 2005/0086587 A1 | 4/2005 | Balz |
| 2005/0144072 A1 | 6/2005 | Perkowski et al. |
| 2005/0165626 A1 | 7/2005 | Karpf |
| 2005/0186550 A1 | 8/2005 | Gillani |
| 2005/0246304 A1 | 11/2005 | Knight et al. |
| 2006/0004603 A1 | 1/2006 | Peterka et al. |
| 2006/0107219 A1 | 5/2006 | Ahya |
| 2006/0184493 A1 | 8/2006 | Shiffman et al. |
| 2006/0205564 A1 | 9/2006 | Peterson |
| 2006/0206861 A1 | 9/2006 | Shenfield et al. |
| 2006/0259483 A1 * | 11/2006 | Ozana ..................... G06F 16/95 |
| | | 707/999.005 |
| 2006/0282516 A1 | 12/2006 | Taylor |
| 2007/0021984 A1 | 1/2007 | Brown |
| 2007/0072156 A1 | 3/2007 | Kaufman et al. |
| 2007/0136093 A1 | 6/2007 | Rankin et al. |
| 2007/0179361 A1 | 8/2007 | Brown et al. |
| 2007/0250429 A1 | 10/2007 | Walser et al. |
| 2008/0005679 A1 | 1/2008 | Rimas-Ribikauskas |
| 2008/0010254 A1 | 1/2008 | Settimi |

(56) References Cited

U.S. PATENT DOCUMENTS

| | | |
|---|---|---|
| 2008/0021287 A1 | 1/2008 | Woellenstein et al. |
| 2008/0034314 A1 | 2/2008 | Louch et al. |
| 2008/0077865 A1 | 3/2008 | Hiles et al. |
| 2008/0126110 A1 | 5/2008 | Haeberle |
| 2008/0127040 A1 | 5/2008 | Barcellona |
| 2008/0140444 A1 | 6/2008 | Karkanias |
| 2008/0140758 A1* | 6/2008 | Lee .................. G06F 40/174 709/201 |
| 2008/0177638 A1 | 7/2008 | Butler |
| 2008/0201174 A1 | 8/2008 | Ramsubramanian |
| 2008/0261191 A1 | 10/2008 | Woolf et al. |
| 2008/0301118 A1 | 12/2008 | Chien |
| 2009/0024944 A1 | 1/2009 | Louch |
| 2009/0035733 A1 | 2/2009 | Meitar et al. |
| 2009/0043689 A1 | 2/2009 | Yang |
| 2009/0076856 A1 | 3/2009 | Darby et al. |
| 2009/0094052 A1 | 4/2009 | James et al. |
| 2009/0119678 A1 | 5/2009 | Shih |
| 2009/0150814 A1 | 6/2009 | Eyer |
| 2009/0150919 A1 | 6/2009 | Lee et al. |
| 2009/0156190 A1 | 6/2009 | Fisher |
| 2009/0163182 A1 | 6/2009 | Gatti |
| 2009/0172002 A1 | 7/2009 | Bathiche |
| 2009/0248883 A1 | 10/2009 | Suryanarayana et al. |
| 2009/0276771 A1 | 11/2009 | Nickolov et al. |
| 2010/0036681 A1 | 2/2010 | Naik et al. |
| 2010/0041378 A1 | 2/2010 | Aceves |
| 2010/0088245 A1 | 4/2010 | Harrison et al. |
| 2010/0122286 A1 | 5/2010 | Begeja |
| 2010/0131482 A1 | 5/2010 | Linthicum |
| 2010/0179833 A1 | 7/2010 | Roizen et al. |
| 2010/0211941 A1 | 8/2010 | Roseborough |
| 2010/0218132 A1 | 8/2010 | Soni et al. |
| 2010/0235889 A1 | 9/2010 | Chu et al. |
| 2010/0250258 A1 | 9/2010 | Smithers et al. |
| 2010/0262664 A1 | 10/2010 | Brown et al. |
| 2010/0325144 A1 | 12/2010 | Fischer et al. |
| 2010/0333037 A1 | 12/2010 | Pavlovski |
| 2011/0066934 A1 | 3/2011 | Treisman |
| 2011/0112852 A1 | 5/2011 | Ware et al. |
| 2011/0126119 A1 | 5/2011 | Young |
| 2011/0145747 A1 | 6/2011 | Wong et al. |
| 2011/0173308 A1 | 7/2011 | Gutekunst |
| 2011/0200979 A1 | 8/2011 | Benson |
| 2011/0225203 A1* | 9/2011 | Hart-Davidson ...... G06Q 10/10 707/E17.055 |
| 2011/0288900 A1 | 11/2011 | McQueen et al. |
| 2011/0307331 A1 | 12/2011 | Richard et al. |
| 2012/0035954 A1 | 2/2012 | Yeskel |
| 2012/0036220 A1 | 2/2012 | Dare et al. |
| 2012/0047029 A1 | 2/2012 | Veres et al. |
| 2012/0069977 A1* | 3/2012 | Oberoi ................ H04M 3/5158 379/92.01 |
| 2012/0072232 A1 | 3/2012 | Frankham et al. |
| 2012/0084399 A1 | 4/2012 | Scharber et al. |
| 2012/0089521 A1 | 4/2012 | Abrevaya et al. |
| 2012/0102050 A1 | 4/2012 | Button |
| 2012/0143694 A1 | 6/2012 | Zargahi |
| 2012/0143697 A1 | 6/2012 | Chopra |
| 2012/0214147 A1 | 8/2012 | Ernst et al. |
| 2012/0215639 A1 | 8/2012 | Ramer et al. |
| 2012/0260294 A1 | 10/2012 | Reichardt et al. |
| 2012/0266251 A1 | 10/2012 | Birtwhistle et al. |
| 2012/0272156 A1 | 10/2012 | Kerger |
| 2013/0060922 A1 | 3/2013 | Koponen et al. |
| 2013/0085744 A1 | 4/2013 | Arias |
| 2013/0103749 A1 | 4/2013 | Werth et al. |
| 2013/0110565 A1 | 5/2013 | Means |
| 2013/0145024 A1 | 6/2013 | Cao |
| 2013/0145457 A1 | 6/2013 | Papkipos et al. |
| 2013/0151710 A1 | 6/2013 | D'souza et al. |
| 2013/0158368 A1 | 6/2013 | Pacione et al. |
| 2013/0166494 A1 | 6/2013 | Davis |
| 2013/0179472 A1 | 7/2013 | Junqua |
| 2013/0197894 A1* | 8/2013 | Sablinski ............ G16H 10/20 703/11 |
| 2013/0212487 A1 | 8/2013 | Cote |
| 2013/0238686 A1 | 9/2013 | O'Donoghue |
| 2013/0283188 A1 | 10/2013 | Sanghvi |
| 2013/0326375 A1 | 12/2013 | Barak et al. |
| 2013/0329632 A1 | 12/2013 | Buyukkoc et al. |
| 2014/0017648 A1 | 1/2014 | Williams et al. |
| 2014/0019480 A1 | 1/2014 | Rychikhin |
| 2014/0026113 A1 | 1/2014 | Farooqi |
| 2014/0033171 A1 | 1/2014 | Lorenz |
| 2014/0052681 A1 | 2/2014 | Nitz et al. |
| 2014/0088995 A1 | 3/2014 | Damani |
| 2014/0100883 A1* | 4/2014 | Hamilton ............ G16H 50/70 705/3 |
| 2014/0101628 A1 | 4/2014 | Almog |
| 2014/0109072 A1 | 4/2014 | Lang et al. |
| 2014/0109115 A1 | 4/2014 | Low |
| 2014/0109177 A1 | 4/2014 | Barton et al. |
| 2014/0155705 A1 | 6/2014 | Papadopoulos et al. |
| 2014/0156645 A1 | 6/2014 | Brust |
| 2014/0156823 A1 | 6/2014 | Liu |
| 2014/0157171 A1 | 6/2014 | Brust et al. |
| 2014/0173405 A1 | 6/2014 | Ferrara |
| 2014/0181715 A1 | 6/2014 | Axelrod |
| 2014/0187228 A1 | 7/2014 | Fisher |
| 2014/0240122 A1 | 8/2014 | Roberts |
| 2014/0257058 A1 | 9/2014 | Clarysse et al. |
| 2014/0258827 A1 | 9/2014 | Gormish |
| 2014/0273913 A1 | 9/2014 | Michel |
| 2014/0278536 A1 | 9/2014 | Zhang |
| 2014/0282061 A1 | 9/2014 | Wheatley et al. |
| 2014/0288955 A1 | 9/2014 | Zhou et al. |
| 2014/0288971 A1 | 9/2014 | Whibbs, III |
| 2014/0298260 A1* | 10/2014 | Abowd ............ G06F 3/04842 715/810 |
| 2014/0309868 A1 | 10/2014 | Ricci |
| 2014/0310607 A1* | 10/2014 | Abraham ........... G06F 16/2457 715/738 |
| 2014/0317595 A1 | 10/2014 | Kilby |
| 2014/0344397 A1 | 11/2014 | Kostof |
| 2014/0358482 A1 | 12/2014 | Sehgal |
| 2014/0358828 A1 | 12/2014 | Phillipps et al. |
| 2014/0365961 A1 | 12/2014 | Lefor et al. |
| 2015/0006214 A1 | 1/2015 | Lavoie et al. |
| 2015/0012301 A1 | 1/2015 | Weschler et al. |
| 2015/0019342 A1 | 1/2015 | Gupta |
| 2015/0025917 A1 | 1/2015 | Stempora |
| 2015/0025997 A1 | 1/2015 | Tilenius et al. |
| 2015/0056589 A1 | 2/2015 | Zhang et al. |
| 2015/0074635 A1 | 3/2015 | Margiotta |
| 2015/0088955 A1 | 3/2015 | Hendrick et al. |
| 2015/0089224 A1 | 3/2015 | Beckman |
| 2015/0100887 A1 | 4/2015 | Verkasalo |
| 2015/0106449 A1 | 4/2015 | Cherry |
| 2015/0135160 A1 | 5/2015 | Gauvin |
| 2015/0143470 A1 | 5/2015 | Stiekes et al. |
| 2015/0148061 A1 | 5/2015 | Koukoumidis |
| 2015/0154002 A1 | 6/2015 | Weinstein et al. |
| 2015/0163121 A1 | 6/2015 | Mahaffey |
| 2015/0178473 A1 | 6/2015 | Hufford et al. |
| 2015/0178474 A1 | 6/2015 | Hufford et al. |
| 2015/0199490 A1 | 7/2015 | Iancu et al. |
| 2015/0212714 A1 | 7/2015 | Hua |
| 2015/0220233 A1 | 8/2015 | Kok et al. |
| 2015/0286802 A1 | 10/2015 | Kansara |
| 2015/0294090 A1 | 10/2015 | Kodiyan |
| 2015/0317337 A1 | 11/2015 | Edgar |
| 2016/0004831 A1 | 1/2016 | Carlson et al. |
| 2016/0021040 A1 | 1/2016 | Frei et al. |
| 2016/0058287 A1 | 3/2016 | Dyell |
| 2016/0085754 A1 | 3/2016 | Gifford et al. |
| 2016/0092339 A1 | 3/2016 | Straub |
| 2016/0124930 A1 | 5/2016 | Dhawan |
| 2016/0139884 A1 | 5/2016 | Valentino et al. |
| 2016/0196389 A1 | 7/2016 | Moturu et al. |
| 2016/0203663 A1 | 7/2016 | Proctor |
| 2016/0217118 A1 | 7/2016 | Singh |
| 2016/0234624 A1 | 8/2016 | Riva et al. |

(56) References Cited

U.S. PATENT DOCUMENTS

| | | |
|---|---|---|
| 2016/0300570 A1 | 10/2016 | Gustafson et al. |
| 2016/0314110 A1 | 10/2016 | Corcoran |
| 2016/0357794 A1 | 12/2016 | Liang et al. |
| 2016/0357944 A1 | 12/2016 | Iyer et al. |
| 2017/0000422 A1 | 1/2017 | Moturu et al. |
| 2017/0004516 A1* | 1/2017 | Hudson .............. G06Q 30/0203 |
| 2017/0024546 A1 | 1/2017 | Schmidt |
| 2017/0039324 A1 | 2/2017 | Francois et al. |
| 2017/0048215 A1 | 2/2017 | Straub |
| 2017/0097743 A1 | 4/2017 | Hameed et al. |
| 2017/0124276 A1 | 5/2017 | Tee |
| 2017/0132395 A1 | 5/2017 | Futch |
| 2017/0169343 A1 | 6/2017 | Kirkham et al. |
| 2017/0118159 A1 | 7/2017 | Ratiu et al. |
| 2017/0201779 A1 | 7/2017 | Publicover et al. |
| 2017/0228229 A1 | 8/2017 | Jain et al. |
| 2017/0231528 A1 | 8/2017 | Nathan |
| 2017/0286389 A1 | 10/2017 | Ceneviva |
| 2017/0303187 A1 | 10/2017 | Crouthamel et al. |
| 2017/0308680 A1 | 10/2017 | Efros et al. |
| 2017/0323064 A1 | 11/2017 | Bates |
| 2017/0329483 A1 | 11/2017 | Jann et al. |
| 2017/0329500 A1 | 11/2017 | Grammatikakis et al. |
| 2017/0330297 A1 | 11/2017 | Cronin et al. |
| 2017/0344895 A1 | 11/2017 | Roy |
| 2017/0358242 A1 | 12/2017 | Thompson et al. |
| 2017/0374178 A1 | 12/2017 | Sharma et al. |
| 2018/0046780 A1 | 2/2018 | Graiver et al. |
| 2018/0089159 A1 | 3/2018 | Jain et al. |
| 2018/0090229 A1 | 3/2018 | Sanyal |
| 2018/0114596 A1 | 4/2018 | Churchwell et al. |
| 2018/0121187 A1 | 5/2018 | Jain et al. |
| 2018/0122509 A1 | 5/2018 | Christiansson |
| 2018/0144100 A1 | 5/2018 | Chalas et al. |
| 2018/0150523 A1 | 5/2018 | Shiffman et al. |
| 2018/0174243 A1* | 6/2018 | Mishra ................. G06Q 40/123 |
| 2018/0176331 A1 | 6/2018 | Jain et al. |
| 2018/0197624 A1 | 7/2018 | Robaina et al. |
| 2018/0206775 A1 | 7/2018 | Saria et al. |
| 2018/0210870 A1 | 7/2018 | Jain et al. |
| 2018/0210936 A1 | 7/2018 | Reynolds et al. |
| 2018/0246570 A1 | 8/2018 | Coleman et al. |
| 2018/0286509 A1 | 10/2018 | Shah |
| 2018/0302357 A1* | 10/2018 | Cohen ................... H04L 51/212 |
| 2018/0330281 A1 | 11/2018 | Teller et al. |
| 2018/0341378 A1 | 11/2018 | Morrow |
| 2018/0365316 A1 | 12/2018 | Liang et al. |
| 2019/0002982 A1 | 1/2019 | Wang |
| 2019/0026663 A1 | 1/2019 | Homeyer et al. |
| 2019/0043619 A1 | 2/2019 | Vaughan et al. |
| 2019/0068753 A1 | 2/2019 | Jain et al. |
| 2019/0174165 A1 | 6/2019 | Pizzurro et al. |
| 2019/0198172 A1 | 6/2019 | Nelson, Jr. |
| 2019/0201123 A1 | 7/2019 | Shelton et al. |
| 2019/0207814 A1 | 7/2019 | Jain |
| 2019/0294633 A1* | 9/2019 | Dembo ............... G06F 3/04847 |
| 2019/0306093 A1 | 10/2019 | Schilling et al. |
| 2019/0320310 A1 | 10/2019 | Horelik et al. |
| 2019/0361579 A1 | 11/2019 | Srivastava |
| 2020/0005417 A1 | 1/2020 | Agasi et al. |
| 2020/0035335 A1* | 1/2020 | Kivatinos ............ G06N 3/0454 |
| 2020/0035341 A1 | 1/2020 | Kain et al. |
| 2020/0050330 A1 | 2/2020 | Schilling et al. |
| 2020/0082918 A1 | 3/2020 | Simhon et al. |
| 2020/0131581 A1 | 4/2020 | Jain et al. |
| 2020/0203012 A1 | 6/2020 | Kamath et al. |
| 2020/0241859 A1 | 7/2020 | Jain et al. |
| 2020/0241860 A1 | 7/2020 | Jain et al. |
| 2020/0243167 A1 | 7/2020 | Will et al. |
| 2020/0250508 A1 | 8/2020 | De Magalhaes |
| 2020/0267110 A1 | 8/2020 | Nolan et al. |
| 2020/0278852 A1 | 9/2020 | Jain et al. |
| 2020/0279622 A1 | 9/2020 | Heywood et al. |
| 2020/0303074 A1 | 9/2020 | Mueller-Wolf |
| 2020/0336450 A1 | 10/2020 | Gao et al. |
| 2020/0348919 A1 | 11/2020 | Jain |
| 2020/0356353 A1 | 11/2020 | Jain |
| 2020/0364588 A1 | 11/2020 | Knox |
| 2021/0026615 A1 | 1/2021 | Jain |
| 2021/0090103 A1* | 3/2021 | Deshmukh .............. G06N 3/084 |
| 2021/0391083 A1* | 12/2021 | Moturu .................. G09B 19/00 |

FOREIGN PATENT DOCUMENTS

| | | |
|---|---|---|
| EP | 2851820 | 3/2015 |
| EP | 2545468 | 1/2016 |
| JP | 2016512619 A | 4/2016 |
| JP | 2019526851 A | 9/2019 |
| WO | WO 1995012812 | 5/1995 |
| WO | WO 2011112556 | 9/2011 |
| WO | WO 2012078753 | 6/2012 |
| WO | WO 2013144769 | 10/2013 |

OTHER PUBLICATIONS

Conductscience.com, "Learn about your patients in their territory", published on or before Oct. 12, 2020, retrieved on Mar. 4, 2021, retrieved from URL<https://conductscience.com/human-lab/digital-health/ecological-momentary-assessments/>, 28 pages.

Final Office Action in U.S. Appl. No. 15/040,635, dated Apr. 13, 2017, 13 pages.

Final Office Action in U.S. Appl. No. 15/152,411, dated Mar. 17, 2017, 17 pages.

ilumivu.com, "Ecological Momentary Intervention", published in 2009, retrieved on Mar. 4, 2021, retrieved from URL<https://ilumivu.com/markets/researchers/ecological-momentary-intervention/>, 3 pages.

KhanAcademy.org, [online] "Khan Academy," Available on or before Nov. 2, 2012, via Internet Archive: Wayback Machine URL <http://web.archive.org/web/20111202083549/http://www.khanacademy.org/> retrieved Mar. 11, 2020, 20 pages.

Maher et al., "Ecological Momentary Assessment Is a Feasible and Valid Methodological Tool to Measure Older Adults' Physical Activity and Sedentary Behavior", Frontiers in Psychology, published on Aug. 15, 2018, 9:1485.

McDevitt-Murphy et al., "Use of Ecological Momentary Assessment and Intervention in Treatment with Adults", Focus, 2018, 6 pages.

Moskowitz et al., "Ecological Momentary Assessment: What it is and why it is a method of the future in clinical psychopharmacology", Journal of Psychiatry and Neuroscience, 2006, 31(1):13-20.

NationalElfService.net, "Ecological Momentary Interventions: Smartphones have changed everything and heres how digital mental health might begin to catch up", published on Jul. 28, 2017, retrieved on Mar. 4, 2021, retrieved from URL<https://www.nationalelfservice.net/treatment/digital-health/ecological-momentary-interventions-smartphones-have-changed-everything-and-heres-how-digital-mental-health-might-begin-to-catch-up/>, 13 pages.

Non-Final Office Action in U.S. Appl. No. 15/040,635, dated Dec. 30, 2016, 11 pages.

Non-Final Office Action in U.S. Appl. No. 15/040,635, dated Jul. 8, 2016, 9 pages.

Non-Final Office Action in U.S. Appl. No. 15/067,046, dated Nov. 1, 2016, 19 pages.

Non-Final Office Action in U.S. Appl. No. 15/152,411, dated Dec. 7, 2016, 10 pages.

Non-Final Office Action in U.S. Appl. No. 15/279,845, dated Apr. 21, 2017, 10 pages.

Non-Final Office Action in U.S. Appl. No. 15/337,222, dated Mar. 23, 2017, 13 pages.

Non-Final Office Action in U.S. Appl. No. 15/382,126, dated Mar. 17, 2017, 16 pages.

Parmar et al., "Ecological Momentary Interventions Delivered by Smartphone Apps: Applications in Substance Use Treatment in Indian Scenario", Indian Journal of Psychological Medicine, Feb. 2017, 39(1):102-103.

Shiffman et al., "Ecological Momentary Assessment", Annual Review of Clinical Psychology, 2008, 4(1):1-32.

(56) References Cited

OTHER PUBLICATIONS

Shiffman., "Ecological Momentary Assessment", Oxford Handbook of Substance Use and Substance Use Disorders, Oct. 2016, 2:86 pages.
Wikipedia.com, "Experience sampling method", published in 2020, retrieved on Mar. 4, 2021, retrieved from URL<https://en.wikipedia.org/wiki/Experience_sampling_method>, 4 pages.
[No Author] "Methods for JITAIs Just in Time Adaptive Intervention," Nov. 9, 2016, retrieved on Nov. 9, 2016, retrieved from URL<https://community.isr.umich.edu/public/Default.aspx?alias=community.isr.umich.edu/public/jitai&>, 1 page.
Airwatch: "Airwatch Laptop Management Demo," YouTube, Oct. 3, 2014, retrieved on May 3, 2017, retrieved from URL<https://www.youtube.com/watch?v=3gHfmdVZECM>, 1 page.
alphr.com [online], "How to Write a Chrome Extension", published on Nov. 22, 2010, retrieved on Oct. 18, 2021, retrieved from URL<https://www.alphr.com/tutorials/363031/how-to-write-a-chrome-extension/>, 12 pages.
Conner, "Experience Sampling and Ecological Momentary Assessment with Mobile Phones," 2015, retrieved on May 3, 2017, retrieved from URL<http://www.otago.ac.nz/psychology/otago047475.pdf>, 4 pages.
ditoweb.com [online], "What is the Google Chrome Web Store?", published in Aug. 2012, retrieved on Oct. 18, 2021, retrieved from URL<https://www.ditoweb.com/2012/08/what-is-google-chrome-web-store/>, 8 pages.
edsurge.com [online], "Extensions, Add-Ons and Apps, Oh My! How to Utilize Google in Your Classroom", published on Oct. 13, 2014, retrieved on Oct. 18, 2021, retrieved from URL<https://www.edsurge.com/news/2014-10-13-extensions-add-ons-and-apps-oh-my-how-to-utilize-google-in-your-classroom>, 5 pages.
ghacks.net [online], "The Best Way to Find New Extensions on the Chrome Web Store", published on May 12, 2014, retrieved on Oct. 18, 2021, retrieved from URL<https://www.ghacks.net/2014/05/12/best-way-find-new-extensions-chrome-web-store/>, 6 pages.
Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.
groovypost.com [online], "How Safe is it to Download Chrome Extensions", published on Mar. 4, 2011, retrieved on Oct. 18, 2021, retrieved from URL<https://www.groovypost.com/howto/reviews/chrome-extensions-privacy-security/>, 7 pages.
Guyot, "Apple's ResearchKit: Our Complete Overview," Mar. 9, 2015, retrieved on Mar. 30, 2020, retrieved from URL<https://www.macstories.net/news/apples-researchkit-our-complete-overview/>, 8 pages.
Henze et al., "Push the study to the App store: evaluating off-screen visualizations for maps in the android market," Proceedings of the 12th Conference on Human-Computer Interaction with Mobile Devices and Services, Lisbon, Portugal, Sep. 7-10, 2010, 373-374.
Heron, "Ecological Momentary Intervention [EMI]: Incorporating mobile technology into a disordered eating treatment program for college women," Psychology—Dissertations, paper 157, 2011.
Kotsiantis, "Supervised Machine Learning: A Review of Classification Techniques", Informatica 31, Jul. 2007, pp. 249-268.
Lunn et al., "Using Mobile Technology to Engage Sexual and Gender Minorities in Clinical Research," Plos One, May 2, 2019, 14(5), 19 pages.
makeuseof.com [online], "How Safe Is the Chrome Web Store Anyway?", published on Apr. 10, 2015, retrieved on Oct. 18, 2021, retrieved from URL<https://www.makeuseof.com/tag/secure-chrome-web-store-anyway/>, 16 pages.
Matthews, "Johns Hopkins Researchers to Use Apple Watch Data to Study Epilepsy," Oct. 15, 2015, retrieved on Mar. 30, 2020, retrieved from URL<https://hub.jhu.edu/2015/10/15/apple-watch-epi-watch/>, 3 pages.
Milward, "Ecological momentary assessment," Jul. 2015, retrieved on May 12, 2017, retrieved from URL <https://www.addiction-ssa.org/commentary/emerging-research-methods-series-ecological-momentary-assessment>, 3 pages.
obgyn.com [online], "Neural Networks", published in 2002, retrieved on Jan. 19, 2021, 34 pages.
Pogue, "Apple's First 5 Health ResearchKit Apps in Brief," Jul. 1, 2015, retreived on Mar. 30, 2020, retrieved from URL<https://www.scientificamerican.com/article/pogue-apples-first-5-health-researchkit-apps-in-brief/>, 4 pages.
Rabelo et al., "Development of a real-time learning scheduler using reinforcement learning concepts", Proceedings of the 1994 9th IEEE International Symposium on Intelligent Control, 1994, pp. 291-296.
Runyan et al., "Virtues, ecological momentary assessment/intervention and smartphone technology," Frontiers in Psychology, May 2015, 6:481, 24 pages.
sbir.cancer.gov [online], "322 Real-Time Integration of Sensor and Self-Report Data for Clinical and Research Applications", published on Jun. 24, 2015, retrieved on Oct. 18, 2021, retrieved from URL<https://sbir.cancer.gov/funding/contracts/pastcontracts/322>, 3 pages.
sbir.cancer.gov [online], "340 Validation of Mobile Technologies for Clinical Assessment, Monitoring and Intervention", published on Jun. 24, 2015, retrieved on Oct. 18, 2021, retrieved from URL<https://sbir.cancer.gov/funding/contracts/pastcontracts/340>, 3 pages.
sbir.cancer.gov [online], "NIH/NCI 342: Validation of Mobile Technologies for Clinical Assessment, Monitoring and Intervention", published on Jul. 24, 2015, retrieved on Oct. 24, 2015, retrieved from URL<https://sbir.cancer.gov/funding/contracts/nihnci342>, 4 pages.
sitepoint.com [online], "How to Create a Chrome Extension in 10 Minutes Flat", published on Apr. 8, 2015, retrieved on Oct. 18, 2021, retrieved from URL<https://www.sitepoint.com/create-chrome-extension-10-minutes-flat/>, 11 pages.
smallbusiness.chron.com [online], "What Is the Chrome Web Store", published on Oct. 6, 2011, retrieved on Oct. 18, 2021, retrieved from URL<https://smallbusiness.chron.com/chrome-store-26652.html>, 5 pages.
Taivan et al., "Application Diversity in Open Display Networks," Proceedings of the International Symposium on Pervasive Displays, Copenhagen, Denmark, Jun. 2014, 68-73.
techcrunch.com [online], "Google Gives Chrome Web Store a Welcome New Lick of Paint", published on Oct. 15, 2011, retrieved on Oct. 18, 2021, retrieved from URL<https://techcrunch.com/2011/10/25/google-gives-chrome-web-store-a-welcome-new-lick-of-paint/>, 8 pages.
web.archive.com [online], "Extension Templates and Samples", published on Jul. 15, 2020, retrieved on Oct. 18, 2021, retrieved from URL<https://web.archive.org/web/20200715011834/https:/dev.opera.com/extensions/extension-samples/>, 5 pages.
West et al., "There's an App for That: Content Analysis of Paid Health and Fitness Apps," Journal of Medical Internet Research, May-Jun. 2012, 14(3): e72, 12 pages.

\* cited by examiner

PLATFORM TO INCREASE PATIENT ENGAGEMENT IN CLINICAL TRIALS THROUGH SURVEYS PRESENTED ON MOBILE DEVICES

FIELD OF INVENTION

This application generally relates to the generating and delivering interactive modules over a network.

BACKGROUND

Various techniques are used for interacting with users of mobile devices. Mobile applications often provide interactions that include games, user-fillable forms, displayable content and so on. Different approaches are used to generate and deliver the content that is displayed to users.

SUMMARY

In some implementations, a computer system is configured to provide interactive modules that can dynamically adjust their interaction with users depending on user inputs and other factors. For example, a module can present prompts to a user of the computer system (e.g., a survey or other interactions to gather data from a user), and the system can vary the set of prompts or other interactions depending on the scoring and cumulative set of interactions of the user with the module. As an example, the system may receive a form data package corresponding to a particular module that the user has been tasked with completing. The form data package may contain various prompts, rules for presenting the prompts and scoring the corresponding input, and metadata that relates the prompts to the rules. After presenting a prompt to the user, the system may receive corresponding input in the form of user responses and/or sensor data, and proceed to use the rules to score the input. The system may track the collective score for the module or a particular portion of the module, and use the collective score in combination with the rules to, for example, select a subsequent prompt to present, determine if the current portion of the module is complete, select a subsequent portion of the module to have the user start, or determine if the module is complete.

As discussed further below, the system can provide cumulative ranking and scoring across multiple questions and inputs. A user's cumulative interactions with a module or portion of a module can be scored in an ongoing manner, during the interactions. For example, as a user answers questions in a series of questions, a cumulative score can be updated for each interaction. The system can then evaluate the cumulative score for a group of questions to change state of the form (e.g., a set or sequence of views or questions) a cumulative score for the answers to multiple questions. A cumulative score is determined across different questions or interactive element, with the cumulative score being updated with each user interaction. The module provide dynamic termination or adjustment of the survey in response to the cumulative score reaching a threshold. The threshold might be a confidence level in a certain decision, a desired level of data collection being reached, or achievement of another purpose for the module.

In some implementations, the interactive module includes different sections. These portions of the assessment may each include one or more prompts (e.g., questions requesting an answer, activities requesting an input or selection by the user, requests for the user to perform a physical activity, etc.). As an example, if the user has been tasked with completing a health assessment containing a mental health section, a cardiovascular health section, and a sleep quality section, the system may start the assessment by presenting prompts that are part of the mental health section and track a collective score for the mental health section based on the user's corresponding responses. The system may compare the collective score to a score threshold in the rules for the mental health section. In comparing the collective score to the score threshold, the system may determine that the collective score meets the score threshold, indicating, for example, that there is sufficient confidence that the user is not at risk of having a mental disorder. In response, the system may determine that the mental health section is complete and present the user a first prompt of the cardiovascular section.

In some implementations, an interactive module includes scoring parameters indicating how scores for the user interactions with the module are to be determined (e.g., equations, rules, tables, etc. for generating scores) and how the scores are to be evaluated (e.g., thresholds, ranges, rules, and other criteria). The scoring parameters may include, for example, scores that correspond to particular prompts, scores that correspond to predetermined inputs that a user might provide (e.g., different scores for different multiple-choice options) or ranges of inputs that a user might enter (e.g., if user input is numerical from 0-10, a score for an input in a 0-2 range, another score for an input in a 3-5 range, and so on), score thresholds for particular sections of the interactive module, and a score threshold for completing or otherwise ending the interactive module. The scoring parameters may further include score threshold for making other determination or for performing other actions. For example, if, after completing all prompts of a cardiovascular section of the interactive module, the collective score for the cardiovascular section does not meet a minimum score threshold, the system may determine that the user is at a serious risk of a heart attack. In response, the system may end the interactive module, present a notification to the user of the health risk, and contact the user's doctor.

In some implementations, the rules include collection parameters that provide various requirements for input corresponding to the prompts. For example, the collection parameters may outline a minimum response time to prevent the user from answering prior to reading the prompt, a maximum response time which may result in a time-out, requirements that the same response (e.g., yes or no, choice A, etc.) cannot be inputted more than a threshold number of times consecutively, etc. The collection parameters may also indicate information for the system to collect. For example, based on the collection parameters, the system may track user response times, matching user responses or substantially similar user responses, indications of skipped prompts or sections of the interactive module, etc.

The modules discussed herein can be server-based content modules that have interactions and content incrementally served to user devices, such as one question or interaction at a time or in groups of interactions at a time. User responses can be provided back to the server over a network. Score determination, analysis of the scores, and adjustment to the presentation of the module (e.g., adding questions, skipping questions, initiating a different section of interactions, terminating early, using a different sequence or path through the questions, etc.) can be done by the server. Alternatively, a module can have the content, parameters, rules, scoring criteria and reference values, etc. included into a data package that is sent over a network for an application on the user device to receive and process. The data package can provide the client device the content and logic needed for the client device to generate and present the interactions of the module, including to dynamically score the module and adjust the presentation according to the scores.

In one general aspect, a method performed by an electronic device includes: receiving, by the electronic device, a form data package from a server system over a communication network, wherein the form data package specifies (i) a plurality of form elements for presentation by the electronic device and (ii) one or more rules configured to control output by the electronic device and evaluate user input provided in response to the form elements; based on the form data package, presenting, by the electronic device, a first element from among the plurality of form elements specified by the form data package received from the server system over the communication network; determining, by the electronic device, (i) a first score based on a user response to the first element and (ii) a cumulative score for the form data package based at least in part on the first score; and controlling, by the electronic device, operation of the electronic device based on application of the one or more rules specified in the form data package received from the server system over the communication network, wherein controlling the operation of the electronic device comprises selectively presenting other form elements from among the plurality of elements based on an evaluation performed using the cumulative score.

In some implementations, the form data package comprises scoring parameters indicating how to generate scores for the form data package and to evaluate generated scores.

In some implementations, controlling operation of the device comprises adjusting sensor data collection by the electronic device, adjusting data storage or data reporting by the electronic device, or adjusting a set of form elements presented by the electronic device.

In another general aspect, a method performed by one or more computing devices includes: accessing, by the one or more computing devices, form data for an interactive module, wherein the form data that specifies (i) a plurality of elements for presentation by the one or more computing devices and (ii) one or more rules for evaluating user input provided in response to presentation of the elements; based on the form data, causing, by the one or more computing devices, presentation of a first element from among the plurality of elements specified by the form data; determining, by the one or more computing devices, (i) a first score based on a user response to the first element and (ii) a cumulative score for the interactive module based at least in part on the first score; and based at least in part on the cumulative score, selecting, by the one or more computing devices, from among multiple options for adjusting presentation of the interactive module, wherein the multiple options include at least one of selectively presenting other elements from among the plurality of elements, terminating presentation of the interactive module, or initiating presentation of an additional interactive module.

In some implementations, the form data comprises scoring parameters indicating how to generate scores for the interactive module and to evaluate generated scores.

In some implementations, selecting from among the multiple options comprises adjusting sensor data collection by a device associated with the user, adjusting data storage or data reporting of the interactive module, or adjusting a set of form elements presented for the interactive module.

In some implementations: the cumulative score is generated based on responses to each element in a series of multiple form elements presented at the electronic device; the evaluation comprises determining that the cumulative score satisfies a threshold; and controlling the operation of the electronic device comprises bypassing presentation of one or more form elements in the plurality of form elements based on determining that the cumulative score satisfies the threshold.

In some implementations, the cumulative score indicates a confidence level or a level of completeness of data collection for the form package.

In some implementations, the cumulative score indicates a risk level for a health condition.

In some implementations, the interactive module provides an ecological momentary assessment or an ecological momentary intervention.

In some implementations, the element comprises a request for the user to perform a physical activity, and the element causes the user device to generate sensor data monitoring the physical activity.

In some implementations, adjusting presentation of the interactive module to perform the selected option.

In some implementations, the cumulative score is used to selectively present the prompts. Only a proper subset of the prompts in a module may be presented based on the user's responses and the scores for the user's responses, and how those scores combine into the cumulative score relative to a reference value.

In some implementations, a module includes multiple groups of questions that are each scored together. The system can determine cumulative scores for each group and use the cumulative scores to selectively present score; then score the groups In some implementations, the system updates and compares the cumulative score with a reference value to determine how to adjust presentation of the module after each user response to a question.

In some implementations, the system updates and compares the cumulative score with a reference value to determine how to adjust presentation of the module after the each of multiple different groups of multiple questions.

In some implementations, the cumulative score represents a measure of data quality or validity for data being collected using the module. If the cumulative score falls below a threshold the series of interactions can be changed to abort the assessment or to add additional interactions (e.g., additional survey questions, sensor data collection, etc.) to increase the quality of the collected data.

In some implementations, the cumulative score indicates a level of confidence (e.g., in a classification of the user, a risk level for the user, a likelihood or severity of a risk to the user, etc.). When providing the module for presentation to the user, the system can evaluate the cumulative score to see if it reaches a threshold, which can represent a targeted minimum level of confidence. The module can continue to present interactions that are designed to increase the level of confidence until the cumulative score reaches the threshold, at which point the segment or session can end (e.g., because a risk has been confirmed or ruled out with sufficient confidence).

In some implementations, the cumulative score indicates a level of completeness of information gathered, so that when the cumulative score reaches a desired level the information gathering purpose of the module has been achieved. Reaching the completion threshold for the cumulative score can be done without answering all of the questions in the module, and through different numbers of questions and different sets of questions in the module.

Rather than simply assessing whether all questions are answered or whether a certain amount of the total are answered, the cumulative score can represent the information gain from the different responses, where answering different questions contributes differently to the cumulative score and different answers to an individual question may contribute differently to the cumulative score. As a result, the module can allow different paths through the available questions or interactions to reach the module's goal of collecting information of certain predetermined types (e.g., with answers to questions 1, 2, and 3; or with answers to questions 2, 3, 4, and 5; or with answers to any of questions 1, 3, or 5 along with participating in a mobile-device-based game; etc.).

In another general aspect, a method performed by one or more computers includes: selecting, by the one or more computers, a form module with which to provide a form at a user device, the form module being selected from among a plurality of form modules that each include (i) a set of form elements and (ii) corresponding scoring criteria for evaluating responses to the form elements; determining, by the one or more computers, data collection parameters based on the selected form module, wherein the data collection parameters that adjust a process of collecting input through the form by the user device; determining, by the one or more computers, scoring parameters based on the selected form module, wherein the scoring parameters specifying criteria for assessing responses to the form elements; generating, by the one or more computers, one or more scores for the form based on responses to the form elements, the responses being collected according to the data collection parameters, the one or more scores being determined based on the scoring parameters; and based on an evaluation of the generated one or more scores, providing, by the one or more computers, at least one of (i) an additional form to present at the user device, (ii) an interaction module configured to prompt a user for input or (iii) data indicating a completion event for a session at the user device.

In some implementations, the method includes: determining a set of data elements to be collected through presentation of the form based on the selected form module; and providing form data to the user device over a network, the form data enabling the user device to present a form configured to collect the determined set of data elements.

In some implementations, the data collection parameters specify a range of time that a collected data item is valid. The method comprises: determining that a data item associated with the user device was previously collected within the range of time specified by the data collection parameters; and omitting from presentation one or more form elements configured to collect the data item.

In some implementations, the method includes determining that a data item corresponding to a particular form element can be collected using a sensor of the user device or another device in communication with the user device; collecting the data item using the sensor of the user device or the other device; and omitting the particular data element from presentation.

In some implementations, one or more of the form elements prompt for input of data that is dependent on a current context of the user device or a user of the user device.

In some implementations, one or more of the form elements prompt for input describing a current experience, current behavior, or current mood of a user of the user device.

In some implementations, the collection parameters specify at least one of: a type of data to be collected through the form; a maximum response time for a form element; a maximum response time for the form as a whole; an order of presentation of the form elements; a frequency with which to present the form; an activity for a user to perform; characteristics of responses to measure for one or more form elements; a validity period for prior data collected; or an alternative source of data for one or more form elements.

In some implementations, the scoring parameters specify at least one of: criteria for assessing validity of responses; criteria for assessing validity of input patterns; a threshold or reference for comparison with generated scores for the form; data specifying conditions for achieving a goal or purpose of the form; or criteria for determining when to end a session of interaction with a user.

Other embodiments of these and other aspects disclosed herein include corresponding systems, apparatus, and computer programs encoded on computer storage devices, configured to perform the actions of the methods. A system of one or more computers can be so configured by virtue of software, firmware, hardware, or a combination of them installed on the system that, in operation, cause the system to perform the actions. One or more computer programs can be so configured by virtue having instructions that, when executed by data processing apparatus, cause the apparatus to perform the actions.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
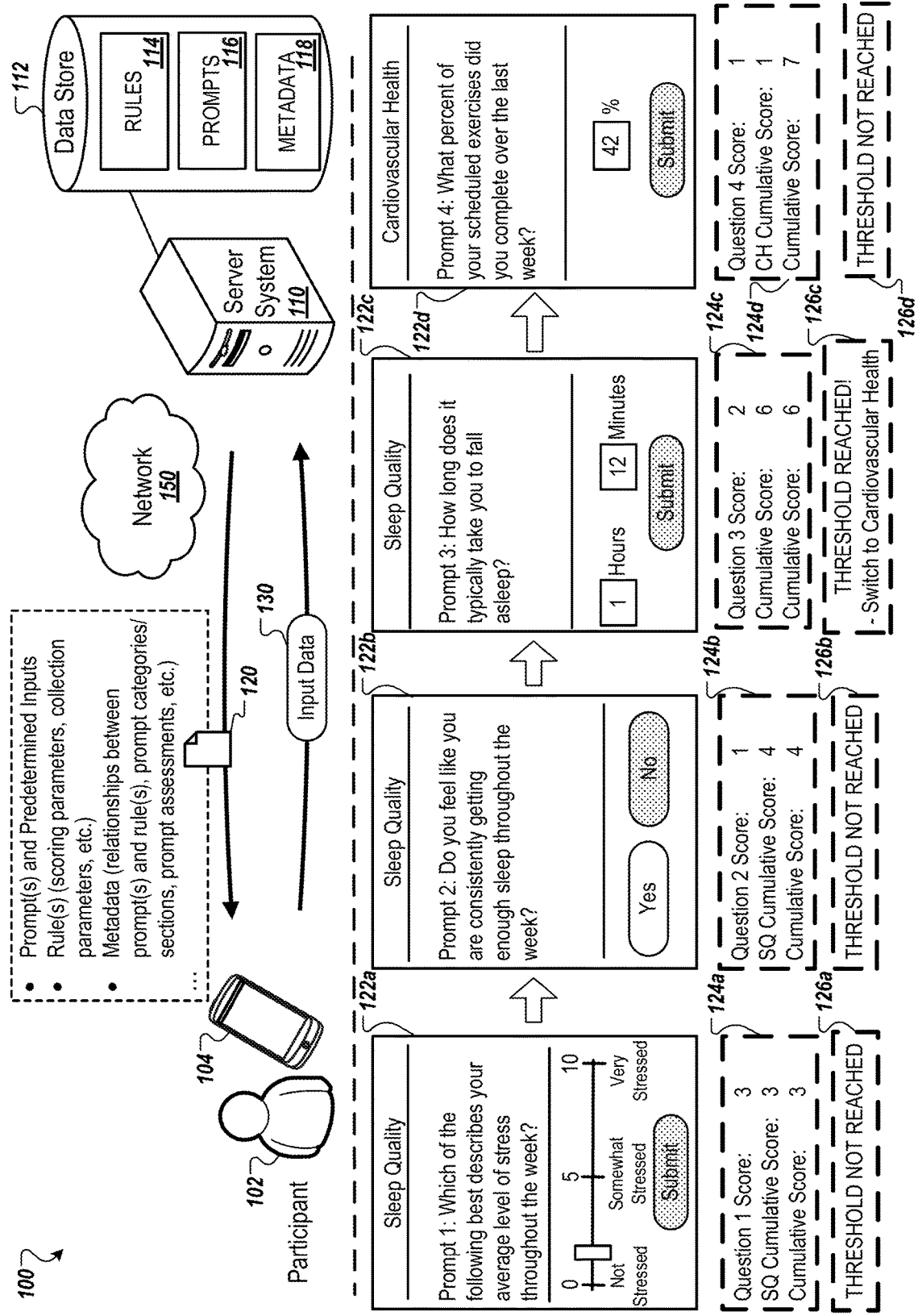
FIG. 1 is a diagram that illustrates an example system for dynamically scoring and presenting an interactive module.

FIG. 1 is a diagram that illustrates an example system 100 for dynamically scoring and presenting an interactive module. The interactive module can be used to provide interactions to a user, e.g., through a mobile device application, and collect information from the user. Among other uses, the system 100 can be used to selectively present prompts of interactive modules, score the corresponding responses, and modify the presentation of the modules or end the modules based on the scores. The interactive modules may be part of research studies, e.g., clinical trials, experimental studies, longitudinal studies, correlational studies, case studies, etc. For example, a researcher may task a participant 102, or a cohort that the participant 102 belongs to, with completing a module or completing the module on a periodic basis (e.g., every day, every week, every month, etc.). The results of the module may indicate, for example, with sufficient confidence that a participant is at risk of having a certain medical condition or has a certain medical condition. Similarly, the results may indicate that a participant is not at risk of a certain medical condition or does not have a certain medical condition. In some cases, the results may include a recommendation of further evaluation, such as a follow-up module or a medical appointment.

The system can assist researchers to efficiently conduct research studies. In the field of medical and health research, many research studies involve tasking a variety of participants with the completion of health-related interactive modules. However, researchers often encounter responses that are inaccurate due to, for example, fatigue of the study participants. In some systems, participants are typically required to respond to every prompt of an assessment before results can be generated. The system can be used to improve the efficiency of research studies by, for example, reducing the length of assessments and the time required to confirm or reject that a given individual is at risk of a medical condition. For example, once enough information is obtained to conclude that a user is not at risk of a certain medical condition or is at risk of a certain medical condition, the system may, in response, skip to a different section of the interactive module or end presentation of the interactive module. This can be used to reduce the number of prompts that the study participants have to respond to and, therefore, can reduce the time required of the participants to complete the interactive module, increase the accuracy of the responses as the participants are less likely to suffer fatigue, reduce the time needed to contact doctors or emergency services if a serious medical condition or risk of a medical condition is detected, etc.

Researchers that conduct health research studies need to extract information from participants throughout a study. The present system can provide a way for them to initiate surveys, forms, actions, and experiences for users, and then obtain and view various results. The results may be more than simply the answers or responses that a user provides. For example, additional context information and information about how the user answered (e.g., time between questions, switching between answers, sensor data and environmental data, and so on). The data gathered the can be provided for viewing and analysis in an online or offline format (e.g., for download). Some examples of information gathered includes a duration of form input contributions, allowing Participant Reported Outcomes (PRO) and factors such as a completion rate, whether there were pauses during presentation of the module, etc. The interactive modules can instruct an application or device to collect context data or sensor data, and then report the collected data back to a server where it is stored in association with the user's identity and an identifier for the research study the user is enrolled in. These can include Data Information Reported Outcomes, such as results of game that detects risk vs. reward preferences of a user or other mental or brain-health related challenges and active engagements. The system can provide classification responses from form data inputs by users, which can have clinical usefulness for health research, mental health, (e.g., cognitive response time, brain fog, decision making, etc.), physical health, (e.g., attribute measures for health-related scoring and decision making, to facilitate risk measures, and goal setting, etc.), emotional health, occupational health, social health, environmental health, spiritual health, and so on, allowing for use in total wellness and holistic care.

The system can use previous survey data to find relationships among the data, which can include using machine learning models to perform clustering analysis. The system can connect different events and interactions to "daisy chain" different interactive elements. For example, rules can conditionally concatenate or bypass certain modules or groups of questions within modules based on the scores for one or more questions. As a result, the same module may present different questions to a user at different times, depending on the context and situation of the user. Survey data for an individual is stored in association with a user identifier for the individual, which is also linked to the user's user profile, medical records (e.g., electronic medical records (EMR) or electronic health records (EHR)), and other information about the user. This information can be used to customize the presentation of the module based on the prior interactions with the module, or with other modules, or with any of the other information collected for the user through other sources (e.g., clinical visits, enrollment surveys, etc.). Related to this is the ability of the system to automatically re-use information previously administered modules (e.g., within a period of validity for the data, such as one week) as a way to reduce the risk of re-asking the same questions again and again.

The system allows modules to be designed that have multiple paths for scoring, such as different ways for a user to reach a desired target score, different branches or sets of questions that are used for different situations, and so on. Other modules may have a single path of scoring. Scores for a module can be based on a series of one or more ecological momentary assessments (EMAs), ecological momentary interventions (EMIs), surveys, survey instrumentation, forms, form data and any active or passive engagement module collected during the inquiry, where scoring can trigger an intervention as an EMI, or another instrument such as another EMA.

EMA techniques provide methods to collect information about an individual (e.g., patient, research participant, etc.) such as symptoms, affect, behavior, and cognitions, close in time to the individual's experience of those elements. This can include measures of a person's physical, mental, and/or emotional state. Often the EMA includes self-reported input from an individual that describes or measures the individual's subjective experience, as well as potentially objective actions, conditions, and context of the individual. In some cases, it is important that at least some of the data gathered reflect the individual's perception about himself or herself (e.g., pain level, fatigue level, mood, etc.) or about the individual's actions or context. Other types of information, such as for physiological data collection or facts about behavior (e.g., did the individual take a medication or not, did the user exercise for 30 minutes today, etc.) objective or factual answers are called for.

Unlike testing for academic performance or in educational settings, the purpose of the EMAs in the modules is typically not to determine how much a person knows or if the user can select a predetermined correct answer to a problem. Rather than testing knowledge or scholastic ability, the EMAs often seek to collect information about the current or recent experience and conditions of the user. Another difference is that the "correct" answer for a given user often varies from one presentation of the EMA to another, the purpose is often data collection of an item not known in advance to the system. For example, a question about a user's mood may be used to find out what the user's mood is, and at different times the user's mood may be different, appropriately leading to different answers for different presentations of the EMA. The answers for an EMA can be the type that change based on context, so that if a user is given the same question each day the answer may be different due to the context. The same question can have different answers depending on the context the user is in. Thus, unlike academic assessments, which are typically knowledge-based questions, there is no single correct answer for most EMAs. EMAs generally do not simply requesting general factual information or preferences, although these may also be requested and provided. Also, unlike personality tests that attempt to measure long-term aspects that do not change quickly, EMAs can be used to measure aspects that do change, and are expected to change frequently, such as potentially on a monthly basis, a weekly basis, a daily basis, or perhaps more frequently.

EMIs can be provided in the same manner as EMAs, wherever an EMA or more general "prompt" is discussed herein. An EMI is an interaction that attempts to promote a behavioral change. For example, an EMI can be a notification or activity on a mobile device that impacts what a user is doing or how the user is behaving. Typically, this includes interactions on a device (e.g., the user's phone) to affect a type of behavior of the user separate from interaction with the device (e.g., diet, exercise, travel, etc.). As a simple example, an EMI in a module could be designed to detect various sensor inputs, determine when a certain combination of data items are detected to classify an activity or condition of the user, and then provide a notification such as "The system observed that you're doing action X, can you do action Y instead?"

An EMA can include sampling data about a subject's current behaviors and experiences in real time, in real-world settings, such as in the subject's natural environment (e.g., in whatever context the person is in at the time). EMA aims to minimize recall bias (e.g., retrospective bias, where the user's answer after the fact may be inaccurate), maximize ecological validity, and allow study of behavior in real-world contexts. EMAs can include self-reported data, such as an individual report conditions present, behaviors performed, and the individual's own rating or estimation of symptoms, capabilities, and so on. An EMA is not restricted to self-reported data, however, and as discussed below an EMA may collect data through information about the user captured through other means, such as performance in a mobile-device-based game (e.g., a video game); data captured before, during, or after a physical activity; assessment of the timing and behavior around answering questions (e.g., to test fatigue in a cognitive fatigue test); and so on.

EMAs, provided through customized modules as discussed herein, can be used to gather information about many different individuals, such as different patients receiving medical care or monitoring, participants in research studies (e.g., members of a clinical trial cohort), and others. The same customized module can be used for different individuals (e.g., different members of a research study cohort, different patients having a same or similar medical condition, etc.) and still the module may provide different presentations of the EMAs (e.g., different formatting, content, sets of questions, sets of data to be gathered, etc.) based on the different responses of the individuals and the available information in their user profiles (e.g., medical history, clinical data, EMR/EHR, etc.). The same customized module can be used repeatedly for a single individual, such as daily or weekly, to acquire longitudinal data showing the user's status over time. In this case, different instances of presentation of the module to even the same user may vary from one time to another, based on factors such as the scoring of responses during the presentation of the module, the period of validity (e.g., time before needing to re-test) for different EMA items, the set of recent data available outside the collection through the module, and so on. Of course, a single research study or clinical setting may concurrently use multiple modules to provide different interactions through an application if desired.

The data retrieved through EMAs provided by the modules helps in assessing the daily routine of individuals and their thinking patterns. The EMAs provided by a module can use event-based and/or time-based sampling schemes. In event-based monitoring, the data is recorded in response to the occurrence of a predefined event of interest, such as the system determining that the user has arrived at a predetermined location or type of location, or has begun a predetermined activity. For example, a module may specify certain conditions that should be monitored for and which may trigger the presentation of one or more EMAs/EMIs of the module. When those conditions are detected (e.g., by a client device or by a server receiving data from a client device), the module initiates the presentation of one or more EMAs/EMIs from the module (e.g., either starting the presentation of the whole module or a portion relevant to the condition triggering presentation). Time-based assessments can be initiated at predetermined intervals. These can be regular intervals, such as at the same time each day or at specific times prompted by the system. Alternatively, irregular intervals may be used, such as allowing the user to perform an EMA at their own discretion within a time frame or time window, such as requiring completion once per day, but allowing the user flexibility to complete it at a time of the user's choice each day. Still other time-based systems can have a variable schedule, such as to present an EMA and collect data at random occasions.

EMA/EMI presentation is often initiated to a user by a notification to a user from an application. From the notification, the user may be able to select a link, button, or other control that starts the data collection process (e.g., survey question presentation or other activities) The experience sampling method evaluates the experience, behavior, and moment to moment fluctuations in mental states in the daily life. In general, EMAs may request that the participants to complete an assessment usually in the form of short questionnaires, which are often provided repeatedly (e.g., daily, weekly, etc.) over a specific period of time. The surveys or other EMAs that a module provides can request information about current mood, perceptions, cognitions, behaviors, and the description of the momentary context (e.g., location, company, activity, etc.). As a whole, EMAs may focus on the symptoms, adaptive functioning, and the overall well-being of the participants.

EMAs/EMIs can collect data for different types of analysis, such as for individual differences, temporal sequences, contextual associations, ongoing assessment during treatment, and to provide real-time interventions in treatment. For assessing individual differences, the data collected through EMAs can be aggregated to measure an individual subject's responses over a period of time. For instance, in the case of pain experienced by a patient, the data could be gathered before and after an intervention to quantify the subject's quality of life. The aggregated data is projected to be reliable because of aggregation of various observations and valid because of the representative sampling, ecological validity, and absence of recall bias.

For natural history, EMA responses can measure how an individual's response changes or fluctuates over a period of time. In other words, time serves as an independent variable, while the subject's intrinsic variation over time is taken the dependent variable. The basic descriptive evidence about the natural history of the symptoms over time can pave path for the better understanding of clinical disorders and consequences.

For temporal sequences data capture and analysis, the longitudinal nature of EMA data can be employed to probe events or experiences in the closest time possible, whether to document antecedents or outcomes of events or behaviors or to examine the cascades of events. In these assessments, the sequence of events is the main focus. These cases represent the utilization of EMA data to assess a hypothesis with respect to the dynamic connections among procedures over time. Data provided by EMA studies can show dynamic correlations that emerge over time as more data is collected, whereas recall-based assessments typically provide information about a static instance in time. By providing temporal resolution, experience sampling methods enable investigators to scrutinize sequences of events and experiences, and to analyze and break down the cascade of events in specific periods of time for better understanding.

Contextual association studies usually investigate the association between two or more events or experiences occurring simultaneously. Although the data is collected longitudinally, the analysis of contextual association is cross-sectional, and it focuses on the co-occurrence of events or experiences rather than their sequence.

Experience sampling techniques can also be used in medical treatment and other interventions. For example, an EMA/EMI can also help in designing effective treatment and intervention plans. Besides the applications in research, EMAs can also be employed for ongoing assessment during treatment. A properly structured EMA module can provide revealing opportunities for a treatment plan. As change is expected during treatment, ongoing assessments can prove to be informative, allowing a system to update or customize the user's treatment plan. EMA data can also capture the processes and mediators of psychotherapy-induced change. Other interventions can be provided. The implementation of EMA methods in real-time interventions can itself be an element of clinical treatment plans. In other words, EMIs can delivering intervention immediately to a user, e.g., to address behaviors at crucial moments in patient's life, as triggered by the detection of certain conditions, contexts, activities, and so on through a mobile-device-generated data stream (e.g., sensor measurements, device activity measures, indications of devices of other users nearby, etc.). The individual patient's history may prove to be helpful in designing effective interventions for others. Additionally, the screening of patients over time could be beneficial in making predictive algorithms. For instance, by noticing indications of increasing stress levels, a module may intervene in an early phase before the individual's symptoms get worse.

The system 100 includes a client device 104, a server system 110, and a data store 112 that stores rules 114, prompts 116, and metadata 118. The client device 104 and the server system 110 may communicate over a network 150. The data store 112 may be part of the server system 110 or a system that is remote with respect to the server system 110. The server system 110 may be capable of accessing data from the data store 112 over a wired connection, or wirelessly over the network 150. The client device 104 may also be capable of accessing data from the data store 112 wirelessly over the network 150.

The network 150 can include public and/or private networks and can include the Internet. The network 150 may include wired networks, wireless networks, cellular networks, local area networks, wide area networks, etc.

The data store 112 provides data storage and retrieval capabilities to the server system 110 and/or to the client device 104. The data store 112 may include, but is not required to include, one or more of a relational database, a centralized database, a distributed database, a data warehouse, a noSQL database, an object-oriented database, a graph database, a cloud-computing database, a data repository, a data lake, etc.

The rules 114 stored in the data store 112 may include scoring parameters and collection parameters that are used by the server system 110 and/or the client device 104 to conduct assessments with the interactive modules. The prompts 116 may include predetermined prompts (e.g., questions, requests, etc.) and input controls or areas (e.g., multiple choice options, numerical field, text field, slider, etc.). The metadata 118 may relate the prompts 116 with the rules 114. That is, the metadata 118 may indicate which scoring parameters and collection parameters should be applied to particular prompts and/or expected inputs of those prompts. The metadata 118 may further indicate categories that the prompts belong to, such as particular sections of a module that the prompt is assigned to. Similarly, in cases where the prompts appear in multiple modules, the metadata 118 may indicate the specific modules that the prompts and their corresponding inputs appear in.

In general, the scoring parameters of the rules 114 may include an indication of scores that are assigned to particular prompts or predetermined inputs (e.g., values expected or of those prompts. For example, for each prompt, the scoring parameters may include multiple scores that can be assigned for the prompt, depending on the user response to the prompt. The predetermined inputs for a prompt may be multiple-choice questions or forced-choice prompts that require selection from a finite set of options (e.g., 3, 5, 10, or some other discrete number of options displayed to the user). The scoring parameters may include a score (e.g., a base score) for each response choice. Similarly, if the predetermined inputs correspond to a slider interface element that is to be presented on the client device 104, the scoring parameters may include a score for each position of the slider if there are discrete positions, or an equation for calculating a resulting score from a slider position. If, instead, the potential inputs for a prompt may be along a range, the parameters may indicate discrete scores for inputs in different ranges, such as a score for each of the identified ranges of values. In some cases, an input for a particular prompt that falls outside of a predetermined range value ranges may result in an error (in which case the system may ask the participant 102 to provide a different input) or a score of 0.

In some cases, the scores assigned to a prompt or to a particular predetermined input for a prompt may be modified. For example, if sensor data from a device of the participant 102 indicates a heightened cardiovascular risk, the client device 104 (or the server system 110) may apply a weight to all scores corresponding to prompts belonging to a cardiovascular section of the module (or otherwise affect the cardiovascular section of the module) to effectively decrease the scores that correspond to those prompts (e.g., a weight of 0.8 may be applied to a base score assigned to each of those prompts). As explained below, this may have the effect of requiring the participant 102 to respond to more prompts in the cardiovascular section of the module.

Additionally or alternatively, the scoring parameters of the rules 114 may include score thresholds for modules and/or different portions of modules. For example, the client device 104 and/or the server system 110 may track collective scores and perform actions in response to those collective scores. Collective scores may be tracked for particular portions (e.g., sections) of a module, and/or for the entirety of the module. If a score threshold for a section is met, the client device 104 may, for example, switch to a different section of the module (or may end the module if other sections are complete). Similarly, if a score threshold for the module is met, the client device 104 may, for example, end presentation of the module.

In some cases, the scoring parameters include score thresholds for particular health conditions. For example, a score threshold for a sleep quality section of a module may indicate that the participant 102 has insomnia or is at risk of insomnia if the threshold is not met after the participant 102 has provided responses for the prompts in the sleep quality section. In response to a score threshold for a particular health condition being met or not being met, the client device 104 (or the server system 110) may generate a notification indicating that the participant 102 is at risk of a health condition, or likely has a health condition. The client device 104 may present the notification to the participant 102 and/or provide it to the server system 110. In turn, the server system 110 may notify a researcher, a doctor for the participant 102, and/or emergency services (e.g., depending on the severity of the health condition and/or confidence in the participant 102 having the health condition). The client device 104 may additionally or alternatively recommend further evaluation for the participant 102 regarding the health condition, such as a recommendation for the participant 102 to complete a module that further evaluates the health condition.

In some cases, the score threshold may be modified based on detected conditions. For example, the scoring parameters may indicate that a score threshold for a mental health section of a module should be increased if a score threshold for a sleep quality section is not met (e.g., indicating poor sleep quality). That is, the scoring parameters may account for how different sections (or even responses to individual prompts) affect other sections of the module. In the above example, the scoring parameters may account for the possibility that poor sleep quality is an indicator for one or more mental health conditions. Accordingly, the score threshold of the mental health section may be dynamically increased to collect additional mental health data from the participant 102, and/or to increase the required confidence for concluding that the participant 102 does not have a mental health condition or is not at risk of a mental health condition.

In some cases, the scoring parameters are particular to the anticipated participant. For example, a user profile for the participant 102 may indicate that the participant 102 has never experienced cardiovascular health issues and/or is at sufficiently low risk of experiencing cardiovascular health issues. In response, the scoring parameters for the participant 102 may indicate that a score threshold for a cardiovascular health section of the module is lower for the participant 102 than other participants (e.g., other participants in the same cohort).

The scoring parameters may also include criteria for scoring a quality of data collected. These quality score(s) may differ from the scores discuss above in that instead of being indicative of a user's traits (e.g., physiological health), they are indicative of the validity and/or trustworthiness of the data collected. The data may be in the form of user responses and/or sensor data collected from a device of the user. As will be discussed in more detail below, the collection parameters may provide for the collection of information that can be used with the scoring parameters to determine quality scores. The collection parameters may provide for the collection of particular data or for the tracking of particular data, such as prompt response times, time for the user to respond to a predetermined number of prompts (e.g., time that the user spent answering the last three prompts, the last five prompts, the last ten prompts, etc.), the time for the user to complete a section of a module, or the total time for the user to complete the module. Other data can include sensor data, such as a heart rate data (e.g., which may indicate a current stress level of the user, cardiovascular health of the user, etc.). Similarly, the collection parameters may provide for identifying inconsistent responses provided by a user (e.g., a user response that is inconsistent with a response the user previously provided during the module, or during a previously provided module), or inaccurate responses (e.g., user responses that are in conflict with collected sensor data).

The quality of data criteria of the scoring parameters may indicate how to generate a quality score for the data collected during the module, or for the quality of data collected during a portion of the module. For example, the quality score may be a cumulative score for an entire module, or for a portion of a module (e.g., a section of the module). The quality score may be calculated using collected data. For example, a response time collected for a particular prompt may be used to determine a quality score for the prompt.

In some cases, collected data corresponding to the collection parameters are used to determine quality scores. As will be discussed in more detail below, the collection parameters may include, for example, minimum response times, maximum response times, suspicious response patterns, etc. As an example, if a user's response time for a particular prompt does not meet a minimum response time (e.g., which may indicate that the user did not read the prompt before responding), then a quality score of 0 may be assigned to the particular prompt and/or added to a cumulative quality score in accordance with the scoring parameters. Similarly, if a user's response time for a particular prompt exceeds a maximum response time (e.g., which may indicate that the user is fatigued), then a quality score of 0.5 (e.g., instead of a maximum score of 1.0) may be assigned to the particular prompt and/or added to a cumulative quality score in accordance with the scoring parameters.

In some cases, the scoring parameters for determining quality scores include criteria that is similar to the collection parameters. For example, the scoring parameters may define a minimum response time that is different from a minimum response time of the collection parameters. If, for example, a user's response time for a particular prompt does not meet a first minimum response time defined in the collection parameters, then the response may be deemed invalid and a score might not be generated for the corresponding prompt. However, if the user's response does meet the first minimum response time, but does not meet a second minimum response time defined in the scoring parameters, then a base quality score (e.g., of 1.0) may be divided in half (e.g., to 0.5).

The quality score (e.g., for a particular prompt) may depend on the extent that collected data deviates from typical data. For example, if a response time for a given prompt deviates more than a threshold percentage from an established typical response time (e.g., response time that is typical for the particular user across all prompts or all prompts of the same type; response time that is typical for the particular user given the amount of text in the prompt and/or the actions that the prompt asks from the user; an average response time for the particular prompt across all past users; etc.), then a quality score of 0.7 (e.g., instead of a maximum score of 1.0) may be assigned to the particular prompt and/or added to a cumulative quality score in accordance with the scoring parameters. The threshold percentage may be set to 100%, such that if a user's response time is more than double the expected response time, then a quality score is determined to be 0.7.

As another example, the quality score (e.g., for a particular prompt) may depend on a detected pattern. For example, if the response times for the last three prompts has increased by at least 50% with each subsequent prompt, then a quality score of 0.6 may be determined for the latest prompt (e.g., to account for the increased likelihood that the user is not reading the entire prompt). Similarly, if the response time has been ten seconds or greater for at least three questions, then a quality score of 0.8 may be determined for the latest prompt (e.g., to account for the increased likelihood of the user becoming fatigued).

As another example, the quality score (e.g., for a particular prompt) may depend on whether a response was out of range. For example, a prompt may have multiple predetermined acceptable responses and/or ranges of acceptable responses that a user can provide. For example, a prompt that is asking a user how many hours of sleep they had last night may request the user to enter a numerical value into a field. The acceptable values for this field would be, for example, between zero and twenty-four. If, for example, the user enters a value of twenty-five to indicate that they slept twenty-five hours last night, the system may lower the quality score for this prompt from 1.0 to 0 (e.g., since this response is not possible).

The scoring parameters may provide for an algorithm to determine a quality score. For example, the scoring parameters may include one or more algorithms for a particular prompt, for a particular type of prompt, for a particular section of the module, or for the selected module. The algorithm(s) may receive data corresponding to the collection parameters as input data. As an example, an algorithm may receive the current response time to the most recent prompt and the user's typical response times as input. The output of the algorithm may be a quality score that it calculates by reducing the maximum score (e.g., of 1.0) by the detected percent change in the user's response time from their typical response time.

A cumulative quality score may be compared to a threshold quality score. For example, if the user's cumulative quality score for a section of the module does not meet a threshold quality score for the particular section, the user may be deemed to have failed the section and, optionally, be asked to retake the section. Similarly, if the user's cumulative quality score for the entire module does not meet a threshold quality score, the user may be deemed to have failed the module and, optionally, be asked to retake the module (or to schedule a time when they can retake the module). For example, if after responding to all prompts in the module a threshold quality score for the module is not reached, then the user may be deemed to have failed the module.

In some cases, the quality score(s) is the only score determined and tracked during a module. That is, a score corresponding to the validity/trustworthiness of the data collected may be the only score that is tracked through a module (e.g., and used to determine if the user successfully completed or failed the module).

In general, the collection parameters of the rules 114 may include an indication of data collection requirements, and/or requirements for ensuring the validity of responses provided by participants. The collection parameters may provide that a particular type of data needs to be collected. For example, the collection parameters may indicate that response times need to be monitored for every prompt, that the time for the user to respond to a predetermined number of prompts must be monitored throughout the module, that the time for the user to complete a section of a module must be monitored, and/or that the total time for the user to complete the module must be monitored. Similarly, the collection parameters may provide for the collection of other data, such as sensor data. For example, the collection parameters may provide for the collection of sensor data that is related to the prompt being asked (e.g., which can be used to determine if the user's responses are consistent with the sensor data, and, therefore, if the user's responses are trustworthy). Other data can include sensor data, such as a heart rate (e.g., which may indicate a current stress level of the user).

The collection parameters may also include criteria for determining the validity of the user's responses and/or other data collected. For example, the collection parameters may include one or more minimum response times that are applicable to all prompts or to a subset of prompts (e.g., may be based on the type of prompt, such whether the prompt requires a multiple choice selection or a text input; may be based on the amount of text in the prompt; may be based on the section of the module that the prompt is in; etc.). Similarly, the collection parameters may provide a maximum response time before a time-out occurs, e.g., and the participant 102 is reminded to respond to the prompt or to confirm that they need more time to respond to the prompt. The maximum response time(s) may be applicable to all prompts or to a subset of prompts.

The collection parameters may also outline other requirements for determining validity of data collected. For example, the collection parameters may include age requirements for sensor data and/or for records (e.g., medical records). Specifically, the collection parameters may provide that sensor data and/or medical records that indicate that the weight of user must have been generated within the last month to be valid. For example, if a user profile for the user indicates that the user self-reported a weight of 234 lb forty days ago, the system may determine that a prompt asking for an updated weight be included in the module and/or not hidden since not valid weight data is available per the collection parameters. Similarly, if the prompt from the user elicits medical records stored on a client device of the user for identifying a verified weight for the user and if the medical records are forty days old, the system may determine that the weight is invalid in accordance with the collection parameters and new weight data is required.

In some cases, the collection parameters indicate the type of data that is to be collected as input and/or requirements for presenting a prompt. For example, the collection parameters may indicate that a particular prompt of the module requires text input and/or should be presented on an interface of the client device 104 with a text field. The collection parameters may also indicate sensor data that should be collected. For example, the collection parameters may indicate that a prompt that asks the participant 102 for their heart rate should not be presented on the interface of the client device 104 if the participant 102's heart rate can be acquired from a device, such as fitness tracker that the participant 102 is presently wearing. Similarly, for a particular prompt, the collection parameters may indicate that both a response and sensor data, if available, should be collected. If there is a conflict between the sensor data and the response, the client device 104 (or the server system 110) may default to accepting the sensor data over the response, or may calculate a substitute value by applying a first weight to the response and a second weight (e.g., higher than the first weight) to the sensor data. For example, if the prompt asks how many hours the participant 102 slept last night and the participant indicates more than eight hours but sensor data from a fitness tracker indicates seven hours, the client device may use the collection parameters to determine that a weight of 0.8 should be applied to the seven hours and a weight of 0.2 should be applied to the eight hours to obtain a substitute value of 7.2 hours of sleep.

In some cases, the collection parameters are particular to the anticipated participant. For example, a user profile for the participant 102 may indicate that the participant 102 generally requires at least 0.8 seconds to response to a prompt. Accordingly, the collection parameters for the participant 102 may provide for a minimum response time of 0.8 seconds.

In some cases, the collection parameters indicate when a user is likely fatigued. That is, the collection parameters may specify criteria that is indicative of user being fatigued. For example, longer than usual response times, a pattern of increasing response times, and/or successive longer than usual response times may be indicative that a user is fatigued. A typical response time be defined by the collection parameters as, for example, a response time that is typical for the particular user across all prompts or all prompts of the same type, a response time that is typical for the particular user given the amount of text in the prompt and/or the actions that the prompt asks from the user, or an average response time for the particular prompt across all past users. The collection parameters may outline that longer than usual is when a response time deviates a threshold percentage from the typical response time (e.g., a 100% deviation would mean that the response time monitored was twice that of a typical response time).

As an example, the system may determine that the user is fatigued if the user responds to a first prompt within three seconds, a second prompt in five seconds, and a third prompt in seven seconds, establishing a pattern of increasing response times. Similarly, the system may determine that the user is fatigued if they take more than ten seconds to respond to three successive prompts.

In response to determining that the user is fatigued, the system may perform one or more actions. For example, the system may request that the user revisit those prompts, may adjust scores corresponding to those prompts, and/or may pause the module and request that the user take a break before restarting (e.g., five minute break).

In some cases, the scoring parameters may indicate score changes if certain collection parameters are not met. For example, if the response time for a prompt does not meet a minimum response time of the collecting parameters, the resulting score may be lowered in accordance with the scoring parameters to account for decreased trust in the participant 102's response. That is, in addition to or in place of keeping a separate quality score, the regular score being tracked may be adjusted based on the trustworthiness of the user's responses.

In general, a prompt may include information that illicit a response from the user. The prompt may include text asking the user to make a selection, enter a value, and/or to perform an action. As an example, a prompt may include one or more questions, such as questions related to treatment during a clinical trial. Additionally or alternatively, the prompt may include diagrams that express a task for the user (e.g., making a selecting, entering a value, and/or performing an action). The task may include requesting the user to perform one or more actions as sensor data is collected. For example, a prompt may ask a user to run in place for three minutes as a sensor collects the user's heart rate data, and another sensor monitors their blood oxygen level.

The server system 110 may have the functionality to generate and provide form data packages to the client device 104 which allow the client device 104 to conduct the corresponding module or a portion of the corresponding module. For example, using contents of a form data package 120 sent by the server system 110, the client device 104 may present prompts of the corresponding module and score the participant 102's responses corresponding to the prompts. The data package 120 may include, for example, a subset of the rules 114 (e.g., one or more rules), a subset of the prompts 116 (e.g., one or more prompts), and a subset of the metadata 118. The data package 120 may further include instructions for presenting prompts of a module. For example, instructions may be included that indicate how to present particular prompts on an interface of the client device 104. These instructions may specify particular interface element(s) that must be presented with the prompts, such as slider(s), button(s), text field(s), numerical field(s), etc.

The client device 104 and/or the server system 110 can score the responses provided by the participant 102. Based on the resulting scores, the client device 104 and/or the server system 110 can modify how the module should be presented to the participant 102. For example, where the form data package 120 corresponds to an entire module, the client device 104 may conduct the module without further data from the server system 110. The client device 104 may present prompts (e.g., in an order selected by the client device 104, specified by the form data package 120, or randomly or semi-randomly selected), and receive responses from the participant 102. The client device 104 may proceed to determine corresponding scores and track collective score(s) that it may use to, for example, identify when to rearrange an order of prompts to present, remove or replace prompts to present, switch sections of the module, or to end the module.

As another example, the form data package 120 may correspond to only a particular portion of the module, such as a particular section of the module. Using the form data package 120, the client device 104 may present prompts that are in this particular section of the module and track a collective score for the section. Once the client device 104 determines that a score threshold for the section is met, the client device 104 may request a new form data package from the server system 110. The client device 104 may additionally provide information to the server system 110 that the server system 110 can use to generate the new form data package, or to determine that the module should be ended. This information may include, for example, the responses that the participant 102 provided, sensor data collected, response times, and other collection related data. The server system 110 may use this information to, for example, determine which section of the module the participant 102 should complete next. The server system 110 may additionally or alternatively use this information to make other determinations, such as if any prompts should be removed or added to the module, or that the module should be ended.

As a further example, the form data package 120 may correspond to a single prompt or there may be no form data package. For example, the server system 110 may provide an individual prompt to the client device 104 with corresponding instructions on how to present the prompt. The client device 104 may send the response and, optionally, corresponding information (such as a response time and/or sensor data related to the prompt) back to the server system 110. The server system 110 may use the response and, optionally, the corresponding information to determine a score for the prompt. After determining the score, the server system 110 may proceed with the module by sending (and/or selecting) a subsequent prompt to send to the client device 104, or may choose to end presentation of the module (e.g., based on the score or a collective score). Similarly, the scoring of the individual prompts may alternatively be performed by the client device 104. For example, the form data package 120 may include a single prompt and rules corresponding to the single prompt. The client device 104 may send the resulting score, e.g., along with the response and corresponding information, to the server system 110 which may track one or more collective scores and select a subsequent prompt to send to the client device 104.

As illustrated in FIG. 1, the client device 104 receives the form data package 120 from the server system 110. The form data package 120 corresponds to a module that includes multiple sections. In particular, the module includes a sleep quality section and a cardiovascular health section. The module may also include one or more additional sections, such as a mental health section.

In response to receiving the form data package 120, the client device 104 may extract the contents of the form data package 120 and use the contents to present a first prompt to the participant 102. The first prompt may be selected randomly (e.g., from all prompts of the module) or semi-randomly (e.g., from all prompts of a particular section that the participant 102 is to complete first). Alternatively, the first prompt may be pre-selected and an indication of which prompt should be presented first may be included in the form data package 120.

The client device 104 presents the first prompt on an interface 122a of the client device 104. The first prompt is presented with a slider interface element that allows the participant 102 to provide numerical inputs corresponding to stress levels recently experienced by the participant 102. The participant 102 can provide a response to the first prompt by moving the slider and/or selecting a submit interface element after the slider is in the position that the participant 102 desires. Here, the participant 102 has moved the slider to a "2" position corresponding with low level of stress before selecting the submit interface element.

The client device 104 may proceed to determine and/or update scores 124a. Specifically, the client device 104 may determine a score for the first prompt using the participant 102's response indicating a low level of stress and the scoring parameters of the form data package 120. For example, the scoring parameters may indicate that a response between "0" and "2" for the first prompt corresponds to a maximum score of three for the first prompt. The client device 104 also starts tracking a cumulative score for the sleep quality section (SQ Cumulative Score) and a cumulative score for the entire module.

The client device 104 may compare the scores 124a to one or more score thresholds of the scoring parameters of the form data package 120 to make a determination 126a. As shown, because no score thresholds have been met, the determination 126a indicates that the threshold(s) have not been met. Based on the determination 126a, the client device 104 proceeds to present a second prompt.

The client device 104 presents the second prompt on an interface 122b of the client device 104. The second prompt is presented with two interface elements, one corresponding to a "Yes" response and a second corresponding to a "No" response. The participant 102 can provide a response to the second prompt by selecting one of the two interface elements. Here, the participant 102 has selected the interface element corresponding to a "No" response.

The client device 104 may proceed to determine and/or update scores 124b. Specifically, the client device 104 may determine a score for the second prompt using the participant 102's response indicating that they did not believe they got enough sleep over the past week and the scoring parameters of the form data package 120. For example, the scoring parameters may indicate that a response of "No" corresponds to a score of one for the second prompt. The client device 104 proceeds to update the sleep quality cumulative score to four and the cumulative score to four.

The client device 104 may again compare the scores 124b to one or more score thresholds of the scoring parameters of the form data package 120 to make a determination 126b. As shown, because no score thresholds have been met, the determination 126b again indicates that the threshold(s) have not been met. Based on the determination 126b, the client device 104 proceeds to present a third prompt.

The client device 104 presents the third prompt on an interface 122c of the client device 104. The third prompt is presented with two numerical fields, one corresponding to hours and a second corresponding to minutes. The participant 102 can provide a response by entering a value into each of the numerical fields and selecting a submit interface element. Here, the participant 102 has provided a response indicating that it typically takes them one hour and twelve minutes to fall asleep.

The client device 104 may proceed to determine and/or update scores 124c. Specifically, the client device 104 may determine a score for the third prompt using the participant 102's response and the scoring parameters of the form data package 120. For example, the scoring parameters may indicate that range of times between 1.0 and 2.0 hours corresponds to a score of two for the third prompt. The client device 104 proceeds to update the sleep quality cumulative score to six and the cumulative score to six.

The client device 104 may again compare the scores 124c to one or more score thresholds of the scoring parameters of the form data package 120 to make a determination 126c. As shown, a score threshold for the sleep quality section has been met. Based on this, the client device 104 determines that the sleep quality section of the module is complete and that the participant 102 should start a different section of the module. Specifically, the client device 104 determines, e.g., based on the contents of the form data package 120 and/or the scores 124c, that the participant 102 should complete a cardiovascular health section next.

In some cases, the determination 126c is made by the server system 110. For example, the input data 130 provided by the client device 104 may include the participant 102's responses and/or the scores 124c for the sleep quality section of the module. The server system 110 may use this information to generate a new data package corresponding to the cardiovascular health section, and/or may provide instruction to the client device 104 indicating to next present prompts corresponding to the cardiovascular health section. The server system 110 may store all or part of the input data 130. The input data 130 may also be used to update a user profile for the participant 130.

Based on the determination 126c, the client device 104 presents a fourth prompt on an interface 122c of the client device 104 that corresponds to a different section of the module, the cardiovascular health section. The fourth prompt is presented with a single numerical field that corresponds to a percentage. The participant 102 can provide a response by entering a value into the numerical field and selecting a submit interface element. Here, the participant 102 has provided a response indicating that they completed about 42% of their exercises over the last week.

The client device 104 may proceed to determine and/or update scores 124d. Specifically, the client device 104 may determine a score for the fourth prompt using the participant 102's response and corresponding scoring parameters (e.g., from the form data package 120 or a new form data package). For example, the scoring parameters may indicate a formula that is used to calculate a score that uses the percentage as an input variable. The client device 104 may use the formula to calculate a score of one for the fourth prompt using the participant 102's 42% response as an input. The client device 104 proceeds to start a cardiovascular health score and updates the cumulative score to seven.

The client device 104 may again compare the scores 124c to one or more score thresholds of the scoring parameters of the form data package 120 to make a determination 126d that no score thresholds have been met. Based on the determination 126d, the client device 104 may determine to present one or more additional prompts to present to the participant 102, such as one or more additional prompts from the cardiovascular health section of the module.

The scores 124a-124d may indicate that traits of the participant 102. For example, the scores 124a-124d may individually or collectively indicate the participant 102's physiological health.

In some cases, the server system 110 (or the client device 454) determines quality scores corresponding to the prompts 122a-122d. The quality score may be based on, for example, the participant 102's response time, response time compared to a one or more immediately preceding response times, response time compared to a typical response time. The quality score may also be affected by determinations as to whether the participant 102's responses were consistent with previous responses or collected sensor data. As an example, if a cumulative quality score for the sleep quality section of the module is not reached, the client device 104 may determine that the participant 102 has failed the section and must retake it before being presented prompts from the cardiovascular health section. Alternatively, the participant 102 may be presented the next section of the module regardless, but may have to retake the failed section at a later time (e.g., may be automatically incorporated into a follow-up module for the user). In some cases, if the participant 102 fails a section of the module, the client device 104 determines that the user has failed the module.

In some cases, the server system 110, instead of the client device 104, determines the scores 124a-124d and makes the determinations 126a-126d. For example, the form data package 120 may include one or more prompts. The client device 104 may present these prompts to the participant 102 and collect the corresponding responses. The client device 104 may provide these responses to the server system 110 which may refer to the rules 114 (e.g., scoring parameters and collection parameters) to determine the scores 124a-124d and make the determinations 126a-126d.

In the system, the scoring of a module (or components of a module) has a purpose and function that is often very different from the scoring of tests in educational settings and tests for personality testing. For example, the scoring is not typically used to measure the user's academic ability or recall of facts, but to assess other aspects of the process of collecting information about the current state (e.g., physiological, emotional, mental, etc.) of an individual. Instead, the scoring can be used to perform functions such as to check data quality, check data sufficiency, determine when a confidence level is reached (e.g., regarding a health risk)

For example, the individual scores and/or the cumulative score can be a measure of data quality for data being gathered through presentation of a module, e.g., consistency, timing, precision, etc., whether the input falls within a reasonable or accepted range, and so on. A cumulative score may represent a level of data quality, starting at 10 with points being deducted for omitted answers, slow responses, delays, inconsistencies, implausible answers, contradiction among answers or between current answers and prior stored data, and so on. If the cumulative score falls below a predetermined threshold, such as 7, over the course of receiving user responses, the module can direct actions to respond to address the issue. Examples include adding additional verifying questions to confirm data that is of suspect validity, to add interactions that can obtain the data through more objective means (e.g., instruct the user obtain weight from a scale having wireless connectivity rather than the user self-reporting), or potentially terminating the session and re-scheduling for another time.

To assess data sufficiency, the cumulative score can be a measure of how well the current presentation of the module has acquired the data needed to reach a data collection goal. The module can be designed to acquire needed information through any of multiple different combinations of inputs. For example, information about a user's activities of the day may be needed and this could be obtained through techniques such as the system accessing calendar data for the user along with the user answering a question to confirm the activities that occurred, the user responding to questions each asking about the amounts of time spent on different categories of activities, or the answering questions to select specific activities from a list of activities. If the user answers the initial questions successfully, the cumulative score can increase based on the added information value of the answered questions to represent the progress toward reaching the system's information gathering goal of obtaining data characterizing the user's activities. Once it reaches a threshold (e.g., after 5 of 15 questions), the presentation of the module or of the section regarding activities can be terminated without completing all of the questions. On the other hand, if the user skips some questions or does not provide sufficient information, or if the answers provided demonstrate that there are gaps in the collected information, the cumulative score representing the acquired data will not reach the threshold so early, and further questions in the module are presented until the cumulative score reaches the threshold or the end of set of questions is reached. If the end of the module or section is reached and the cumulative score still has not been reached, the module can be scheduled to be re-run for the user at a different time, since the low cumulative score indicates that the data collection was not fully successful.

As another example, the cumulative score may be indicative of a confidence level for making a determination about an individual's health. The module may provide questions that are used to assess the likelihood or severity of a health risk or other health condition. Different questions may provide different levels of information, and different answers for a single question may provide different levels of information. For example, for some questions a positive answer may be highly predictive of a health risk, but a neutral or negative answer may be inconclusive or only slightly predictive of the health risk being absent. The module can include a cumulative scoring arrangement so that the cumulative score indicates when sufficient information is achieved to make a high-confidence decision for a user, for example, to determine when the confidence in the system's decision is above threshold (e.g., 80%).

In some cases, the system can start at a neutral score, e.g., 0, and then accumulate a positive or negative contribution to the cumulative score for each question in a series of questions, until the score either reaches a lower threshold (e.g., −5 indicating a high-confidence prediction that a heart attack risk is present) or a higher threshold (e.g., +5 indicating a high-confidence prediction that a heart attack risk is not present). A question can have asymmetrical value or different information contributions resulting in different levels of effect on the cumulative score depending on the user response provided.

The cumulative score for a module can be checked or compared with a reference to determine how to proceed with the presentation of the module at different times or points in presentation. One is at the end of a series of questions or block of questions, whether shown together or individually and sequentially. Another option is to check the cumulative score after the response for each item, e.g., for each individual response or question.

Figure 2:
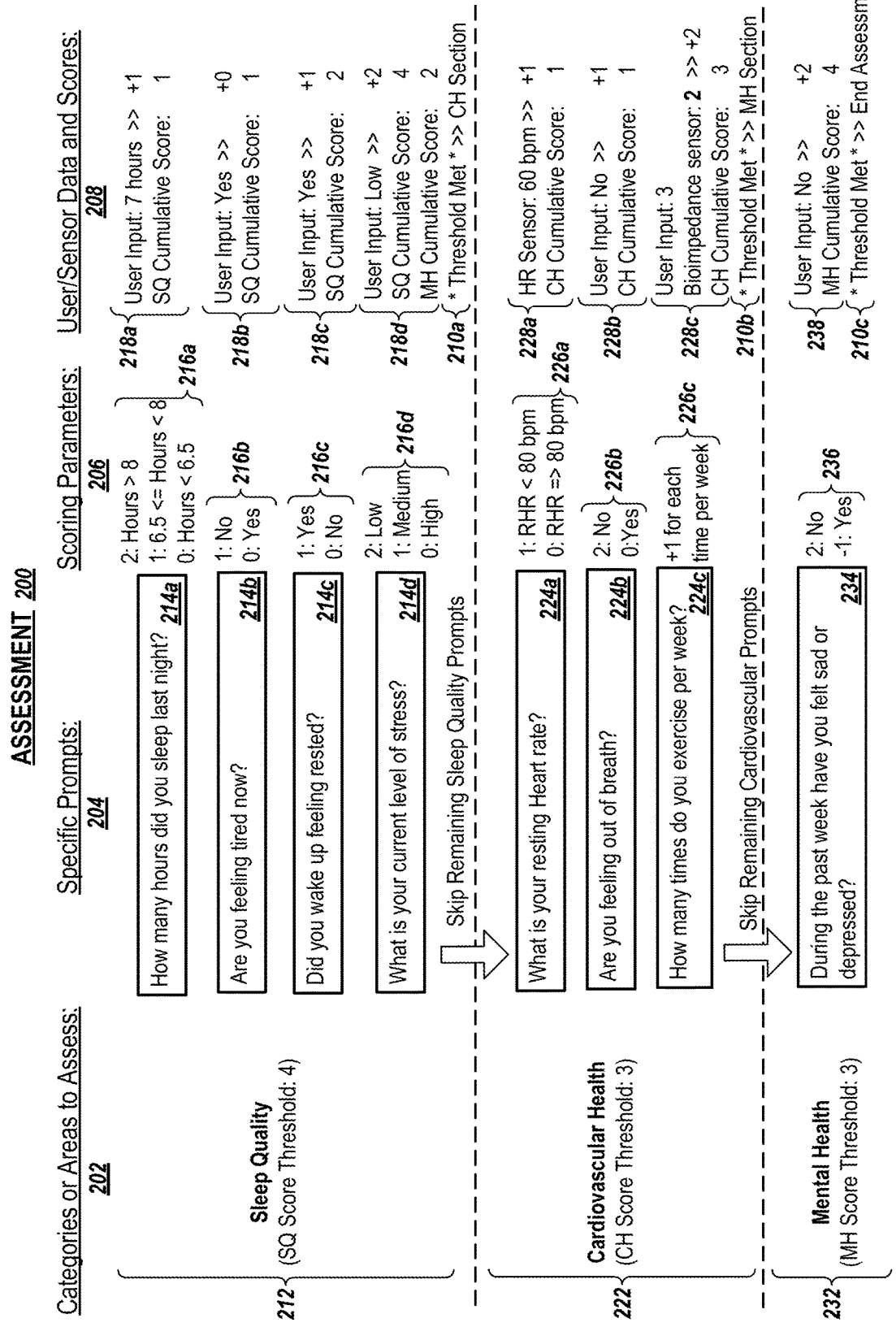
FIG. 2 is a diagram that illustrates example interactions of an interactive module.

FIG. 2 is a diagram that illustrates interactions of an example interactive module 200. As illustrated, the module 200 has already been conducted with a user (e.g., a study participant). The module 200 includes multiple categories or areas to assess 202 (categories 202), e.g., multiple sections. The module 200 further includes various prompts 204 that were previously selected (e.g., by the client device 104 shown in FIG. 1) for presentation to the user. The module 200 has scoring parameters 206 that directly correspond to the prompts 204. Finally, the module includes user/sensor data and scores 208 that correspond to the prompts 204 and the scoring parameters 206. The inputs may have been provided by the user, by a device of the user, or a combination of the two. Specifically, the inputs may be in the form of user responses or sensor data, for example. The scores may be generated using the inputs and the corresponding scoring parameters 206.

As shown, the categories 202 include a first category 212 for sleep quality. Prompts in the category 212, such as the prompts 214a-214d, are designed to gather sleep-related data from user(s). For example, the prompt 214a requests that the user input the number of hours that they slept last night. The data collected during the completion of the category 212 can be used to, for example, conclude with sufficient confidence that the user is at risk of a sleep condition or is not at risk of a sleep condition. For example, the client device 104 may conclude with sufficient confidence that the user is at risk of insomnia is a sleep quality score threshold is not met after the user responds to each sleep quality prompts in the first category 212.

A second category 222 for cardiovascular health similarly includes prompts, such as the prompts 224a-224c, that are designed to gather cardiovascular health. As an example, the prompt 224c asks the user to provide the number of times they exercised over the past week. The data collected from the user (or one or more sensor devices) during the completion of the category 222 can be used to, for example, conclude with sufficient confidence that the user is at risk of a cardiovascular condition or is not at risk of a cardiovascular condition. For example, the client device 104 may conclude with sufficient confidence that the user is not at risk of a heart attached if a cardiovascular score threshold is met prior to completing all of the cardiovascular health related prompts in the second category 222.

The final category shown is a third category 232 for mental health. The third category 232 includes at least one prompt, such as the prompt 234, that is designed to gather mental health related data from the user being assessed. The data collected from the user (or one or more sensor devices) during the completion of the category 232 can be used to, for example, conclude with sufficient confidence that the user is at risk of a mental health condition or is not at risk of a mental health condition. For example, the client device 104 may conclude with sufficient confidence that the user is not at risk of a depression if a mental health score threshold is met prior to completing all of the mental health related prompts in the third category 232. Although the module 200 is shown as having three categories (e.g., sections), the module 200 may have additional categories that were not directly assessed in the example of FIG. 2, e.g., due to other user responses and/or collected sensor data satisfying the scoring parameters for those one or more additional categories.

Forms may obtain information from various sources including stored data on a user's device or from other devices such as a server. A form may prompt a user to allow access to this data. For example, a prompt in the first category 212 may request a user to give permission to access sensor data related to the user's sleeping habits (e.g., bed times, amount of time to fall asleep, hours of sleep, wake-up times, etc.). As another example, a prompt in the third category 232 may, for example, request that a user give permission (e.g., to the server system 110) to access a subset of the user's health records (e.g., relating to mental health treatment).

In some cases, the prompts may task a user with performing one or more actions while sensor data is collected and/or accessed. As an example, a prompt in the second category 222 (e.g., cardiovascular health) may ask a user to jump up and down for thirty seconds as sensor data is collected using one or more sensors of a user device (e.g., heart rate sensor, accelerometer, etc.) or of a device connected to the user device (e.g., a fitness tracker that is wirelessly connected to the user's smart phone over Bluetooth). As part of a module, a form element may instruct or request that the user perform any of various physical actions and cause one or more devices to record sensor data characterizing the action. An element can ask the user to walk in a line or pattern and cause the user's device measure speed, consistency, and balance with accelerometers or other sensors. An element can ask the user to take deep breaths and measure respiration rate, heart rate, and other parameters during the exercise. Other actions may include assuming a pose (e.g., standing, sitting, standing on one leg, holding a yoga pose, etc.), walking, running, staying still, breathing in a specified manner, and so on. These and other requested activities can be used to test the user's balance, endurance, concentration, strength, breathing, and other physical capabilities.

The sensor data acquired in response to these prompts may include physiological measurements of the user, such as their heart rate, blood oxygen level, their weight, their height, etc. Similarly, sensor data about the environment can also be collected and, optionally, used to normalize the physiological measurements and/or to adjust scores for the corresponding prompts. As an example, if the user is outside and the temperature is over 100° outside, then the user device (and/or the server system 110) may normalize the collected heartrate data to account for the high heat (e.g., to estimate what the user's heart rate would be when the temperature is 70°).

As with other elements and modules, the sensor data that is collected during a module element that monitors the user during a physical activity can be dynamically scored as the user performs the activity. For example, a module element can test a user's balance by measuring movement of device carried or worn by the user as the user walks for 30 seconds. This module element can have associated rules that are used to assess the results received from the test during and/or after the activity is complete. The user's device or a server receiving the data can determine a stability score during the test, e.g., for each second, each five second, or on a cumulative basis during the test. The scoring rules can specify that if the stability scores shows high stability over the first 10 seconds, e.g., a score of 8 on a scale of 0 to 10, then the device should terminate the test early, since good balance has been confirmed. A score for the test can also indicate that further tests or questions about balance and mobility can be skipped. The scoring rules can specify that if the scores show very low stability over the first 10 seconds, e.g., a score of 2 on the scale of 0 to 10, the device may instruct the person to terminate the test, because the person may be at risk of falling by performing the test. A low score for the balance element can then lead the system to provide questions if the person has fallen lately or has noticed issues with balance—safer ways to confirm that balance may indeed be a problem for the person. The rules for the module may indicate that if no movement is determined in the first five seconds then the test needs to be restarted or rescheduled for another time. Other rules may specify that if the test has been taken recently, such as in the last five days, then the test does not need to be performed at all. These and other rules or scoring parameters can be manually set by an administrator. As another option, the server system 110 can provide access to form modules that have predetermined sets of scoring conditions or rules already associated with them. For example, a balance module item or module can have a standard set of scoring criteria and rules that are part of the element when the an administrator select it from a library or repository of form modules.

In some cases, the data collected in one of the categories of the module 200 has relevance to one or more other categories. For example, the prompt 214d in the first category 212 may also be relevant to the third category 232 such that a determined score for the prompt 214d may be added to a cumulative score for both the first category 212 and the third category 232 (or may be added to a cumulative score of the third category 232 after a weight is applied to the score in accordance with the scoring parameters 206).

The scoring parameters 206 include particular scoring parameters 216a-216d that correspond to the prompts 214a-214d respectively. Similarly, with respect to the second category 222, particular scoring parameters 226a-226c correspond the prompts 224a-224c respectively. With respect to the third category 232, particular scoring parameters 236 correspond to the prompt 234.

The scoring parameters 206 provide various examples of how user input and/or sensor data corresponding to the prompts 204 can be scored. Specifically, the scoring parameters 206 may include scores assigned to particular predetermined responses. For example, the scoring parameters 216b provide that a score of one is assigned to a predetermined response of "No" and a score of zero is assigned to a second predetermined response of "Yes." The scoring parameters 206 may include scores that are assigned to particular thresholds or ranges of values. For example, the scoring parameters 226a provide that a score of one is assigned to the response if it falls below a threshold value of 80, and a score of zero is assigned if the response meets the threshold value. The scoring parameters 206 may also use formulas that are used to generate scores based on a user's input and/or sensor data. For example, the scoring parameter 226c provides that the score corresponding to the prompt 224c is increased by a value of one for each time per week that the user exercises.

As illustrated in FIG. 2, the scoring parameters 206 may be used to generate scores that are indicative of the user's traits. For example, the scoring parameters 206 may be used to generate scores that correspond to the user's health in the first category 212, the second category 222, and/or the third category 232. However, the scoring parameters 206 may additionally or alternatively provide for generating scores that are indicative of the quality of data collected (e.g., the user's responses, the sensor data collected, etc.). These quality scores may be generated by the client device 104 or the server system 110 based on the scoring parameters and/or the collection parameters.

As an example, a prompt may ask a user with walking in a straight line for 50 ft. The client device 104 may collect sensor data, such as accelerometer data and/or GPS data while the user is performing the assigned task. The accelerometer data and/or GPS data may be used to determine if the user is suffering from any instability or balance problems. The GPS data may also be used to determine when the task is complete, e.g., when the user has walked a length of fifty feet. However, if the accelerometer data indicates that the user experienced an acceleration greater than 20 m/s$^2$ at one or more points in their walk, then the client device 104 (or the server system 110) may determine that the accelerometer data is out of range and cannot be trusted. As such, the client device 104 may determine a relatively low quality score for the prompt based on the possibly inaccurate sensor being used to collect the data.

As discussed above, there may be one or more cumulative quality scores that are used to determine, for example, if the user successfully completed the module 200 or if they failed the module 200. For example, if, after all prompts have been responded to, a threshold cumulative quality score for the module 200 is not met, then the client device 104 or the server system 110 may determine that the use failed the module 200. As such, the client device 104 may present the user with an interface to retake the module or to schedule a new time to take the module (or a modified module). In some cases, the user may only fail a particular portion of the module 200. For example, if a cumulative quality score for the first category 212 is not met after the user has responded to all prompts in the first category 212, the client device 104 (or the server system 110) may determine that the user failed the first category 212. As such, the client device 104 (or the server system 110) may determine that the user failed the entire module 200, or, instead, just the portion of the module 200 corresponding to the first category 212. The server system 110 may add all or a subset of prompts from the first category 212 to a new module for the user to take at a later time.

The user/sensor data and scores 208 include the particular user/sensor data and scores corresponding to each of the prompts 204 and the different categories of the module 200. For example, user/sensor data and scores 218a-218d correspond to the prompts 214a-214d respectively, user/sensor data and scores 228a-228c correspond to the prompts 224a-224c respectively, and user/sensor data and scores 238 correspond to the prompt 234. As described above with respect to FIG. 1, the client device 104 and/or the server system 110 can track cumulative scores, e.g., corresponding to the different categories of the module 200 and/or to the entire module. As shown, through the module 200 a sleep quality cumulative score (SQ cumulative score), a mental health cumulative score (MH cumulative score), and a cardiovascular health cumulative score are tracked.

The scores in the user/sensor data and scores 208 may be used to make one or more determinations. For example, based on the sleep quality cumulative score reaching a score threshold for the first category 212, a determination 210a is made that the threshold is met and that user should be presented prompt(s) of the second category 222. As an example, the score threshold for the first category 212 may have been set to a value of four, and therefore was met by the sleep quality cumulative score of four. Similarly, a determination 210b is made that provides that a cardiovascular health cumulative score has met a score threshold corresponding to the second category 222. The determination 210b further provides that the third category 232 should be started by presenting one or more prompts corresponding to the third category 232 to the user. As an example, the score threshold for the second category 222 may have been set to a value of three, and therefore was met by the cardiovascular health cumulative value of three. A final determination 210c of the module 200 provide that a score threshold corresponding to the third category 232 (or a score threshold corresponding to the entire module 200) has been met and that, in response, the module 200 should be ended (e.g., marked as complete). As an example, the score threshold for the third category 232 may have been set to a value of three that was met by the mental health cumulative score of four.

In some cases, sensor data is used to override or supplement user input (e.g., user responses). For example, the user/sensor data and scores 228c show that the user indicated that the exercised three times per week but sensor data (e.g., from a bioimpedance sensor of a fitness tracker or other mobile device) indicates that the user only exercises twice a week. The scoring parameters and/or collection parameters for the module may indicate a preference for sensor data (e.g., for the specific prompt 224c) over user responses. Accordingly, a score of two is determined for the prompt 224c based on the sensor data instead of a score of three had the user input been accepted. Alternatively, the client device 104 and/or the server system 110 may determine that the prompt 224c should not be presented to the user if it determines that the bioimpedance sensor data is available. In such a case, the client device 104 or the server system 110 may determine, without presenting the prompt 224c and waiting for a corresponding user response, that a score of two should be added to the cardiovascular health cumulative score. Supplementing the module 200 in this way with available sensor data can further help to reduce the length of the module 200, and improve the confidence in the module 200's results.

Figure 3:
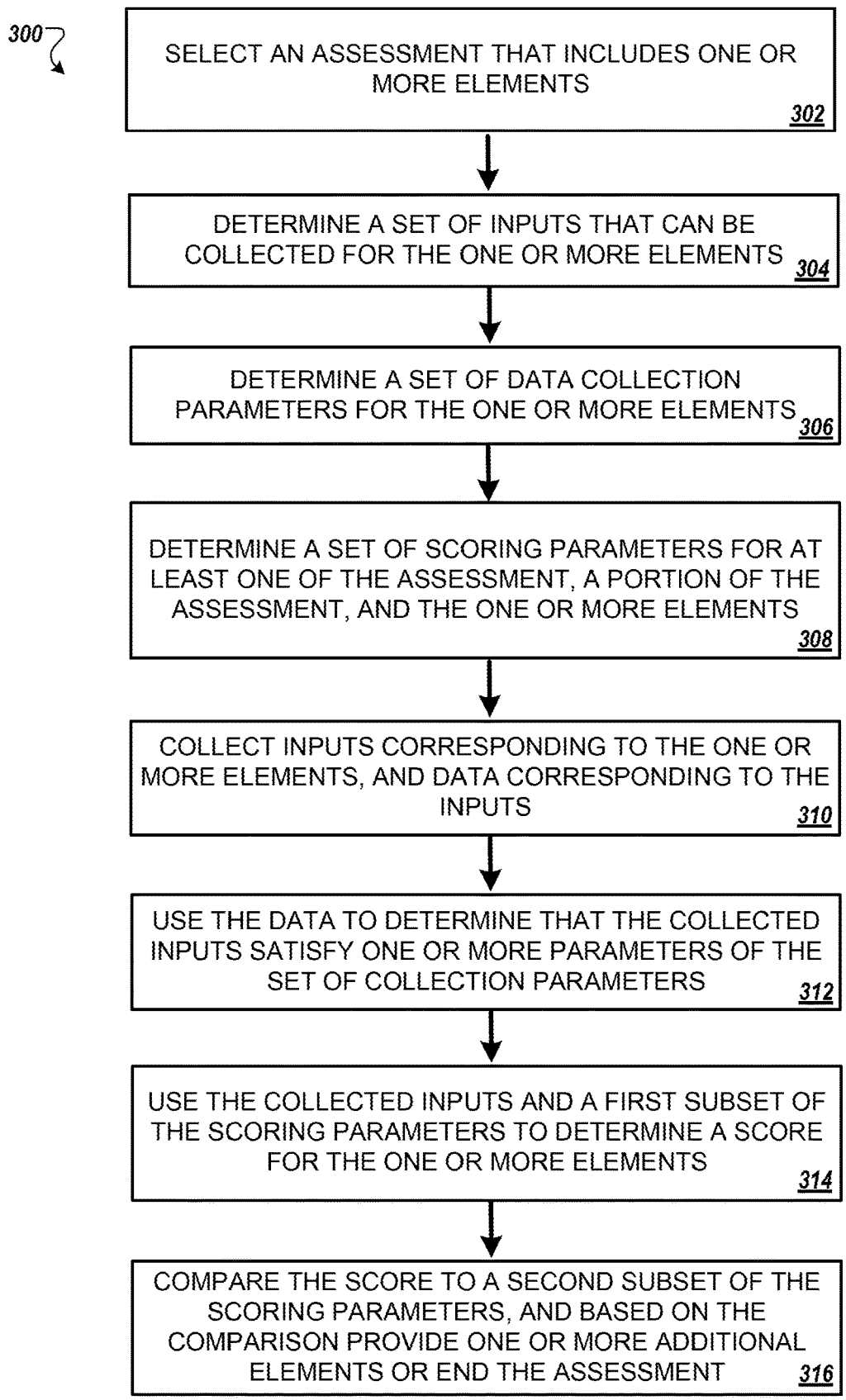
FIG. 3 is a flowchart diagram that illustrates an example process for presenting and scoring an interactive module.

FIG. 3 is a flowchart diagram that illustrates an example process 300 for conducting a module. The process 300 gives an example of how various parameters for data collection, response scoring, and other aspects of a module can be used to enhance or customize the presentation and delivery of modules. The process 300 may be performed in whole or in part by the server system 110 shown in FIG. 1 and FIGS. 4A-4B, the client device 104 shown in FIG. 1, and/or the client device 454 shown in FIG. 4B.

In general, an interactive module can include a single survey or form, or a group of surveys or forms. Each survey or form, and even each element or item (e.g., question or prompt), can have its own data collection needs, data collection parameters, and scoring parameters. For example, the various parameters for a module (whether for the module as a whole, for groups of elements, or individual elements) can specify what data to collect, how the data can be collected, and how to interpret or evaluate that data. The data collection parameters can specify how a data item can be sourced. For example, a user's weight may be required for a module, but the data collection parameters may indicate that if the value was entered or measured recently (e.g., within a month) the prior weight value is still applicable, and so can be taken from prior input or measurements without requesting the individual to enter it again. The time period of use is specified by the data collection parameter. As another example, the parameters can specify data quality checks, such as to verify that the entered weight is within an expected range (e.g., to rule out data entry errors), or that the weight value is within a range including the prior weight value for the user (e.g., within 5% of the previous value, to detect a mismatch compared to a previous survey response). When data does not pass the data quality standards, the survey can notify the user and request the user to the update the result or confirm that the input is accurate.

The scoring of inputs and user behavior during data collection can be used both to determine which module elements to provide and which to omit, as well as to assess the overall quality of collection. For example, the scoring can assess the data quality and data sufficiency for individual items or across multiple items, indicating whether the survey is collecting sufficient information to serve the purpose for which the survey is given (e.g., to assess a health risk, to provide monitoring for a chronic condition, to gather data needed for a research study, etc.). If not, the survey can dynamically adjust its behavior based on the scoring, such as to repeat an element, to continue an activity or test until the needed data is generated, to skip an element that is unnecessary or is providing data of unacceptable quality, to substitute one element for one or more other elements that can obtain needed information in a different way, and so on. The scoring scheme defined for a module can include logic to select from among various different outcomes, such as (i) to continue in the current group of elements, (ii) to terminate the current group of elements (e.g., because the needed data is already obtained, or because the system determined that the needed data cannot be obtained, etc.), or (iii) trigger presentation of other elements (e.g., another survey, form, EMA, or EMI).

The process 300 includes selecting a module that includes one or more elements (302). The one or more elements may be, for example, prompts of a module. As an example, a module may be selected by the server system 110 from the data store 112 shown in FIG. 1. The module may be selected based on instructions received from a researcher or an administrator that identify the specific module and indicate that a particular user or a particular group of users are tasked with completing the module. The module may be selected based on a determination that the module is similar to other modules completed by a particular user. Similarly, the module may be selected based on a determination that the module is required for a particular user or group of user to further evaluate areas where data is sparse or missing, or where a potential risk has been identified. For example, the results of a recently completed mental health module may indicate that a particular user should also complete a sleep quality module due the results indicating that the user may be at risk of sleep insomnia but that further data is needed to conclude with sufficient confidence that the user has sleep insomnia or is at risk of sleep insomnia.

The process 300 includes determining a set of inputs that can be collected for the one or more elements (304). The set of inputs may include predetermined inputs that are stored with corresponding prompts, e.g., in the data store 112 as part of a particular module. The predetermined inputs may include a set of response choices, such as "Yes" and "No", or predetermined multiple choice responses as shown in prompt 442 in FIG. 4B described below. The predetermined inputs may include specific values or ranges of acceptable values. For example, the predetermined inputs for a particular prompt may include a range of values between zero and ten, such as the slider presented in the interface 122a for the first prompt shown in FIG. 1.

The process 300 includes determining a set of collection parameters for the one or more elements (306). The collection parameters may be specified by a researcher or an administrator that created or updated the module. The collection parameters may include rules for determining the validity of responses, such as minimum response times to ensure that a particular user is reading the prompts prior to giving a response. The collection parameters may also indicate the type of response that is being sought after, such as a numerical response, a text response, an interface element selection, an interface slider selection, etc. Similarly, the collection parameters may indicate whether sensor data should be requested, e.g., from the client device 104 or one or more other sensing devices (e.g., fitness tracker, smart watch, etc.). The collection parameters may provide that, if relevant sensor data is able to be obtained, the sensor data should be preferred over user responses, such that, for example, any prompts that are meant to elicit responses to obtain the same or substantially similar data will not be presented to the user (or will only be presented to the user after other prompts have been presented to the user).

The collection parameters may also dictate a minimum number of responses that users taking the module need to provide, e.g., for the entire module or for particular sections of the module. For example, even if a score threshold for completing a section is met, the client device 104 may refrain from switching sections of the module until a user has responded to a threshold number of prompts in the section.

The server system 110 may include the collection parameters, or a subset of the collection parameters (e.g., corresponding to a specific prompt of the module, or a specific section of the module) in a form data package that is to be sent to the client device 104. The client device 104 may use this form data package to conduct at least a portion of the module.

The process 300 includes determining a set of scoring parameters for at least one of the module, a portion of the module, and the one or more elements (308). The scoring parameters may be specified by a researcher or an administrator that created or updated the module. The scoring parameters may include, for example, rules for determining scores for each of the prompts of the module, such scoring parameters 206 shown in FIG. 2. The scoring parameters may also include one or more score thresholds, e.g., that the server system 110 or the client device 104 uses to make determinations and/or trigger particular actions. For example, there may be a first score threshold for determining when a module has been successfully completed, and one or more additional score thresholds for each section of the module for determining when a section is complete. If, for example, the first score threshold is not met after all prompts of the module have been responded to, and/or after each of the section of the module has been completed, the module may be determined to be failure. In response, the user may be asked to retake the module, or may be presented an alternate or modified module.

The process 300 includes collecting inputs corresponding to the one or more elements, and data corresponding to the inputs (310). The inputs collected may include responses provided by a user that is taking the module. The inputs may be collected using an interface, such as the interface 122 of the client device 104 shown in FIG. 1. The inputs may be in the form of interface element selections, numerical data, and/or text data. The data corresponding to the inputs may include, for example, response times (e.g., the time it took a user to provide an input after being presented an element).

In some cases, the inputs include sensor data collected from one or more sensing devices. For example, sensor data such as GPS data may be collected from the client device 104 to determine if a response from the user is accurate, and/or if the corresponding element (e.g., prompt) even needs to be presented to the user.

The process 300 includes using the data to determine that the collected inputs satisfy one or more parameters of the set of collection parameters (312). For example, the client device 104 shown in FIG. 1 may compare the collected inputs to the collection parameters to determine that the inputs are the correct type/format required. If, for example, a numerical input is required for a particular element as specified in the collection parameters, and a user provides a text input, the client device 104 may determine that the collected input does not satisfy that the collection parameters. The client device 104 may avoid using the collected input to score the element, and may request that the user provide an alternate response in the proper format.

The process 300 includes using the collected inputs and a first subset of the scoring parameters to determine a score for the one or more elements (314). The first subset of the scoring parameters may include rules for determining scores for individual elements. For example, the first subset of the scoring parameters may include the scoring parameters 206 shown in FIG. 2. The first subset of scoring parameters may include various ways to determine a score for a particular element, such as using ranges of values that are each associated with a different score, and/or formulas.

The process 300 includes comparing the score to a second subset of the scoring parameters, and based on the comparison provide one or more additional elements or end the module (316). The second subset of the scoring parameters may include, for example, score thresholds. As an example, with respect to FIG. 1, in response to a score threshold for the sleep quality section of the module being met, the client device 104 may switch sections and present the participant 102 a prompt from a cardiovascular health section of the module.

Figure 4A:
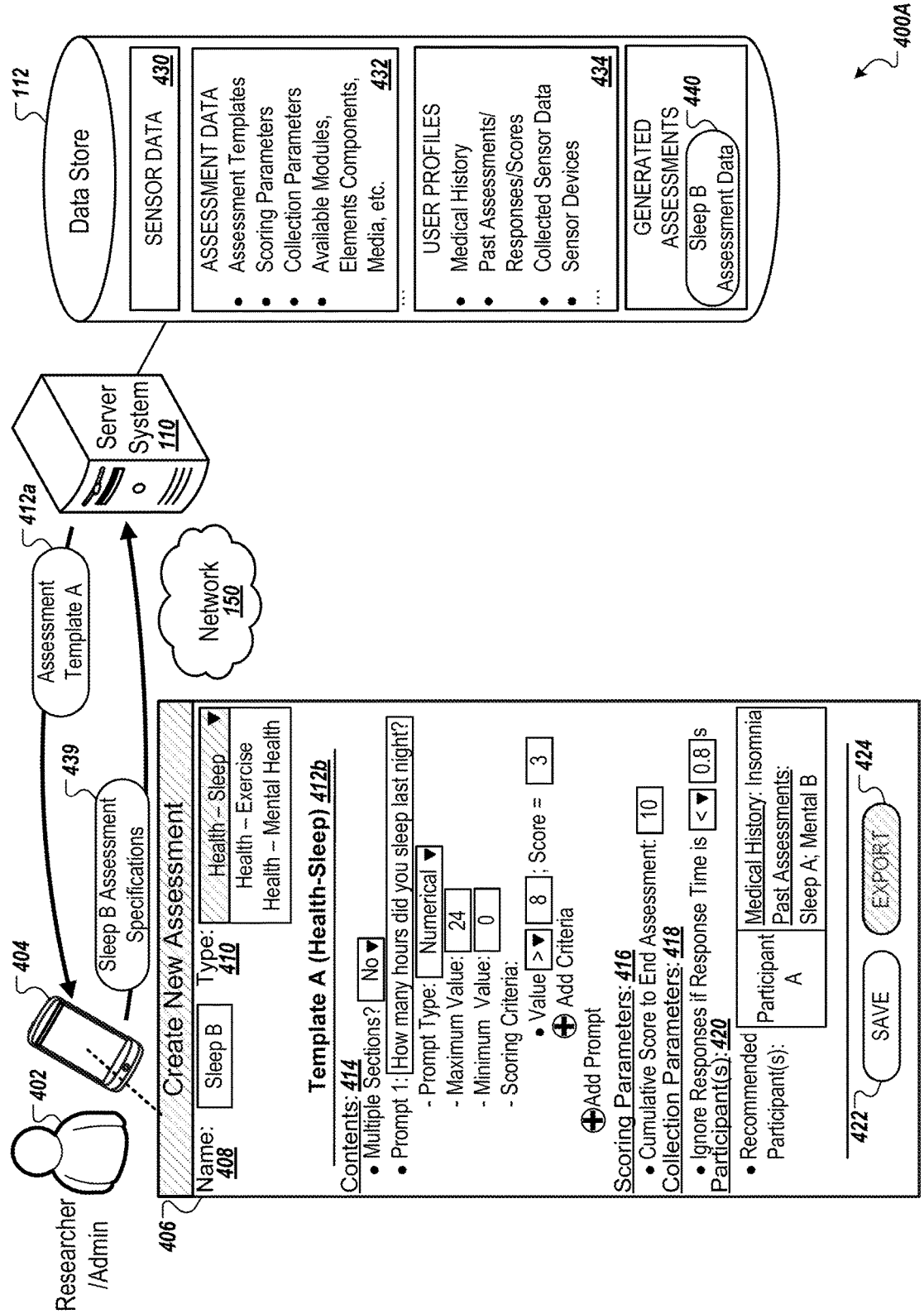
FIG. 4A is a diagram that illustrates an example system for generating an interactive module.

FIG. 4A is a diagram that illustrates an example system 400A for generating a module. The system 400A allows a researcher or administrator 402 (researcher/admin 402) to generate new modules and/or update previously generated modules. The system 400A includes the server system 110, the data store 112, and an administrator device 404 used by the researcher/admin 402. The components of the system 400a can communicate over a wired connection, a wireless connection, or a combination of a wired and wireless connection using the network 150.

As discussed further below, the server system 110 can provide data for a user interface 406 that enables the researcher/admin 402 to generate modules from collections of elements from the data store, e.g., templates for individual prompts, for groups of prompts, and more; media; data collection parameters; response scoring parameters; and so on. The user interface 406 can be an interface of an application installed at the device 404, an interface of a web page or web application in a web browser of the device 404, or another user interface.

The system allows an administrator user to easily configure and publish surveys, including with customized and automated scoring. The system provides functionality for the administrator to provide separate scoring functions and criteria for one or more surveys, or survey instruments within an EMA, as well as configure questions in each form. First, the system enables the administrator to set the hierarchy of surveying modules, surveying content, and related questions for expected inputs (e.g., follow up questions for certain answers, to branch into different levels of detail or specificity as needed). The system also provides an interface for the administrator to set the collection parameter and scoring parameters. The system provides interface controls for the administrator to define outcome-level logic for individual survey responses as well as groups of survey responses, and groups of survey modules. Some examples are:

If the score of the response to question 1 is lower than 5, then hide question 2.

If the score of the response to question 1 is higher than 8, then jump to question 7 because question 2-6 are deemed unnecessary for the user.

Additionally, independent of the answer provided by an individual, evaluate the manner in which data is entered based on the collection parameters, such as user response being too fast, too forced, or inconsistent with previous responses. Restart where necessary and provide explanatory response to individual on a reason for the failure. Alternately, score risk in case of pertinent mental health tests or physical health and attempt to seek help if the user scores at a high-risk level.

If the cumulative score of the first 10 questions are over 80, then end the test. Otherwise, present the next set of questions, or the next EMA.

If the cumulative score of the first 10 questions are over 50, then we should show a message to the user that he/she might have a higher risk of diabetes, and possible deliver an EMI.

The following provide some varying examples of survey instrumentation—where the instruments could be separate EMAs, or combined within the same EMA, or collect additional measures from data on the participant device, devices, or history of data from other providers. Such instruments include, but not limited to:

1) Patient Health Questionnaire-9 (PHQ-9), a 9-item self-report questionnaire that assesses the severity of depressive symptoms (e.g., sadness, crying, or losing interest in life)
2) Generalized Anxiety Disorder-7 (GAD-7), a 7-item self-report questionnaire that assesses the severity of worry and general anxiety
3) Fear of COVID-19 Scale (FCV-19s), a 7-item self-report scale that assesses fears directly related to COVID-19
4) Pittsburgh Sleep Quality Index (PSQI), a single-item measure of sleep quality.
5) Satisfaction with Life: 5-statement battery (7-point agreement scale)
6) Rumination/Experiencing Negative or Unpleasant Event: 4-statement (5-point agreement scale)
7) Adult Hope Scale: 8-statement battery (8-point true/false scale)
8) PCL-5: 20-statement battery with emotion/stress related statements (5-point frequency scale)
9) Meaning in Life: 5-statement battery (7-point true/untrue scale)
10) Self-Compassion: 26 statement battery (5-point frequency scale)
11) Subjective Happiness (4 questions)
   a. In general, "I consider myself . . . " (7-point scale)
   b. Compared to most of my peers (7-point scale)
   c. Characterization statement (7-point scale)
12) Impulse Control: 20-statement battery (4-point agreement scale)
13) Gratitude: 6-statement battery (7-point agreement scale)
14) Emotional Distress: P7D 20-statement battery with emotion/stress related statements (5-point frequency scale)
15) Perceived Social Support: 12-statement battery (7-point agreements scale)
16) Loneliness: 4-statement frequency battery (3-point frequency scale)
17) Mini International Personality Item Pool: 20-statement battery (5-point accuracy scale)
18) Perceived Stress Scale: 4-statement battery with stress related statements
19) PANAS-SF: 20 attribute battery (5-point degree scale)
20) Brief Mood Introspection Scale (BMIS), a 16-point mood scale Various components can be used to provide interactive modules to users. The interactive module can be a programmed module, set by an administrator as discussed in FIG. 4A, that is delivered to the individual through an application. The module includes a survey or survey instrumentation that the end user experiences and is instructed to. The module also includes form sequencing data, which can be the logic or rules for adjusting the order and sequence of related survey questions or forms. A form can be displayable portion of the module that specifies the individual question, informative content, or request. Different portions of a module (e.g., a question, group of questions, or module as a whole) can have data quality requirements specified thorough collection parameters.

During presentation of a module, input data can be anything that the participant provides directly through input, or indirectly through access and permission to data and existing records (according to the parameters associated with the module). Form constructor software, running at a client device or server, uses the module data and available data to determine whether to show or hide certain elements or form fields based on scoring parameters and data collection parameters. Additional elements may involve data access rules and data quality requirements related to necessary inputs. A form collecting agent can be software, at the client or server, for collecting and managing data related to form completion requirements. A form scoring agent can be an expression evaluation engine for scoring actions and outcomes of forms or a series of forms, related to the survey provided by a module.

For example, the system can include a form constructor that includes a "Question" or "Instructions" form as text, or as a video, or as a game. Various form fields in the constructed form provide input data. These fields can be visible user input fields in the interface. As another example, the fields may be invisible to the presentation layer, representing other data that is collected by the system, such as sensor measurements, EHR data, previously reported data, independent form timers. For scoring purposes, a default score may be applied when an answer has not been collected, and individuals may also optionally skip an interaction or question for some modules.

In addition, the data inputs can also have a "Question Answer" as well as a "Question Answer Group" entity. The "Question Answer" entity defines the structure and data for one specific answer for a question, whether visible or invisible to the individual's view in the user interface. Data may be passed into an algorithm for weighting and distribution techniques, or it can be directly assigned a value based on lookup tables associated with the "Question Answer" entity. For example, as a table lookup:

A question has 3 choices, where user can select only one answer

Choice 1 is considered to be the wrong answer, and it has a score of 0

Choice 2 is considered to mostly correct but not comprehensive enough, and so its score is 1

Choice 3 is the most comprehensive and correct answer, it has a score of 3

If the user selects choice 2, the system will evaluate the score of that question for this particular user to be a score of "1."

A "Question Answer Group" denotes multiple fields or entries by the individual for their response to a given instruction or question. It defines groups of answers and apply scoring to those answers as a group. Special consideration is given to algorithmic and table-based opportunities. Where in the case of knowledge-based types of questioning, multi-selection results in a higher scoring factor when considering individual selections absent of the most-correct or aligned with the goals of the module.

In addition, a group of forms or an entirety of the survey instrument can be collectively weighted and scoring applied using additional logic. For example, for a depression assessment module, a total score of all completed sections may indicate a classification of "range 2" of a 5-range classification scale, where range 2 is classified as mostly depressed.

A module can include data collection parameters, scoring parameters, displayable forms, and sequencing parameters (e.g., the order of items or forms, indicating which items to present together, instructions for varying of the order, criteria for determining different sequences, etc.) for the module as a whole. Each form can have its own data collection parameters, scoring parameters, sequencing parameters, and input data to be received, and each input data item can have additional parameters (e.g., to qualify or validate inputs, to modify or customize appearance, content, and behavior, etc.). Thus a module can have a layered structure, with a set of rules and parameters at the module level, another set of rules and parameters at the survey or form level, another set of rules and parameters for individual form elements (e.g., individual user prompts), and another set of rules and parameters for specific inputs or data elements to be collected. These rules allow significant flexibility in customizing the actual presentation of a module. For example, a module may include a form or prompt to obtain data of a type such as resting heart rate or a user's weight is available from a data source (e.g., a mobile device, a connected device, a prior survey response, electronic health records, or other source allowed by the module's rules). Then, when the module is presented, the form or element can be removed from the default sequence of forms to be presented for the module.

Forms are often used to collect information from or about the user. While there are many purposes for this information collection, one relatively common use is to arrive to a numerical value or total score as a result. Some examples include modules to assess a user's knowledge, capability or proficiency, or risk for a disease (e.g., to identify or rule out whether an individual presents a high risk for a certain disease). The platform for generating and delivering modules provides versatile method for scoring results in any type of form or combination of forms. The techniques are particularly helpful forms composed of selection-based questions, where the user response is a selection from among multiple options. Nevertheless, the forms may acquire other types of information from users, such as text inputs, number inputs, sensor data acquired during and about a user activity, and so on.

The data store 112 stores sensor data 430 collected from various devices, e.g., of client devices belonging to study participants. The sensor data 430 may be grouped by the particular users (e.g., study participants) or groups of users (e.g., study cohort) that the sensor data 430 is associated with. For example, the sensor data 430 may be organized by each user that sensor data was collected from. The sensor data 430 may additionally or alternatively grouped by particular research studies or time/date (e.g., sensor data collected over the last six months may be grouped together as more reliable than sensor data collected prior than six months ago). Similar to grouping the sensor data 430 by particular users, the sensor data 430 may be further or alternatively organized by the particular devices that were used to generate the sensor data 430.

The server system 110 may use the sensor data 430 to modify a previously generated module, and/or to make recommended modifications to how a previously generated module is to be presented or to a module currently being created. As an example, if a particular user is known to consistently wear a fitness tracker that includes a heart rate monitor and a GPS unit (e.g., based on their corresponding user profile of the user profiles 434), the server system 110 may determine a prompt asking the user to provide their resting heart rate (RHR) and a prompt asking the user for the number of miles that they ran over the past week be hidden from the user (or removed from a version of the module that is sent to a client device of the user) as the user completes the module. As will be discussed in more detail below, particular prompts or categories of prompts may be recommended for inclusion in a module or a version of a module if it is determined that specific sensor data is not available. For example, if it known that a user does not have a device with a heart rate monitor (e.g., based on a user profile of the user), the server system 100 generate a recommendation for a module with a cardiovascular health section to include one or more prompts that ask the user for their heart rate, or that elicit responses that can be used to estimate the user's current heart rate (e.g., "are you sweating?," "do you feel out of breath?," "what is your resting heart rate?," etc.).

The data store 112 also includes module data 432. The module data 432 may include various module templates and previously generated modules. For example, any modules created by the researcher/admin 402 using the administrator device 404 may be stored as part of the module data 432. In some cases, the server system 110 can use the previously generated modules to create different versions of previously generated modules that are tailored to particular users or particular groups of users (e.g., particular cohorts of a research study). For example, if each of the participants in a particular cohort are known to be diagnosed with a particular medical condition, prompts in a previously generated module that are meant to elicit data to determine if users have or at risk of the particular medical condition may be hidden from the corresponding participants as they complete the module (or may be removed from a version of the module that is sent to the cohort participants).

The module templates may correspond to particular types of assessments. For example, there may be a first module template for sleep health, a second module template for exercise or cardiovascular health, and a third module template for mental health. The module templates may include predetermined (e.g., recommended) rules, such as recommended scoring parameters and collection parameters. For example, a module template for sleep health may include an indication of a recommended score threshold of ten, e.g., to conclude with sufficient confidence that a participant does not have insomnia and to end the assessment. As another example, the collection parameters for the module template may provide a recommendation of a minimum number of prompts that should be included in the assessment, e.g., to determine with sufficient confidence that a user is at risk or has sleep insomnia.

The templates may include or be associated with predetermined (e.g., recommended) content, such as listing of prompts and corresponding responses (or response limits) that are recommended for the type of assessment that template corresponds to, or that have previously been associated with this type of assessment. For example, the module template may include a listing (or a link to a listing) of prompts that have been used in previously generated modules that were used to evaluate sleep quality.

The module templates can include collections of content and user interfaces to be shown to a user. For example, a template may include a series of questions with certain layout characteristics, data collection requirements, and scoring parameters. A user interface 406 for generating or adjusting a module include various fields that allow the researcher/admin 402 to customize the content and rules of the module that is being created using the templates. The user interface 406 may include, for example, numerical fields, text fields, Boolean operator fields, and/or mathematical equation fields for the researcher/admin 402 to define or adjust the content and behavior of the module. The user interface 406 may additionally allow the researcher/admin 402 to specify specific users (e.g., study participants) that are to be tasked with completing the resulting modules. Similarly, the module templates may include or be populated with one or more study participants that are recommended for the module (e.g., based on known health concerns, a time that has passed since they completed an assessment, having completed similar assessments such as previously generated modules of the same type as the module being generated, etc.).

The data store 112 further includes the user profiles 434. The user profiles 434 may include a profile for each user that has previously completed a module, has been tasked with completing a module, and/or is anticipated to be tasked with completing a module. For example, a user profile may be generated for each user when they register for a research study. The user profiles 434 may include medical histories for the users. The server system 110 may use these medical histories to, for example, recommend previously generated modules for particular users, recommend particular users as recipients for a module in the process of being generated, recommend a modification a previously generated module (e.g., to remove or replace one or more prompts, adjust scoring parameters, etc.) for a particular user, and/or to modify the way that a previously generated module is to be presented to a particular user (e.g., hide one or more specific prompts; change the order that sections of the module are presented to the user; etc.).

The user profiles 434 may also include historical data such as past modules completed by the users, responses provided by the sensors, and/or previous scores for the users' responses and/or completed modules. The server system 110 may use this historical data to make recommendations, such as to recommend a particular user as a recipient for a module based on having completed similar modules in the past and/or based on scores for past modules indicating that a particular user is at risk of a particular medical condition. For example, if a user has received low scores in one or more modules or one or more module sections related to cardiovascular health, the server system 110 may recommend that the user be tasked with taking a new cardiovascular health type module.

The user profiles 434 may further include the sensor data collected for various users, or indications of the sensor data collected for various users. For example, a user profile of the user profiles 434 may include an indication (e.g., a link) of a subset of the sensor data 430 that corresponds to the specific user. The user profiles 434 may further include an indication of sensor devices that were previously used and/or are being used to collect sensor data from the users. For example, a user profile may include an indication that a particular user has a smart phone with a GPS unit, a fitness tracker, and sleep sensor that was loaned to the user for a previous study. The server system 110 may use this information to determine that sensor data from the smart phone and the fitness tracker can still be obtained, but that sensor data from the sleep sensor cannot since the study has concluded. The server system 110 may use this information when recommending prompts for a new module. This information can be further used by the server system 110 (or the client device 104 shown in FIG. 1) to change how a module is presented, e.g., by helping the server system 110 determine what prompts should be hidden or how prompts should be rearranged when presenting a module.

In some cases, the sensor data 430 or portions of the sensor data 430 are stored at multiple locations in addition to or in place of the data store 112 (e.g., such as in one or more databases or servers). Similarly, the module data 432 or portions of the module data 432 may be stored at multiple locations in addition to or in place of the data store 112. The user profiles 434 or groups of the user profiles 434 may additionally or alternatively be stored at multiple locations in addition to or in place of the data store 112.

As illustrated in FIG. 4A, the researcher/admin 402 is using the administrator device 404 to create a new module. The researcher/admin 402 opens a new module interface 406 on the administrator device 404 that they can use in creating the new module. The interface 406 may be part of a mobile application for managing and/or creating modules.

Using the interface 406, the researcher/admin 402 inputs a name 408 for the module ("Sleep B"). In some cases, the researcher/admin 402 may receive an error if the name for the module has previously been used and/or a confirmation notification requesting that the researcher/admin 402 confirm that they want to replace the previously generated module. The researcher/admin 402 may also select a type of module 410. For example, the researcher/admin 402 may select "Health-Sleep" using a drop-down list containing various types of modules. The "Health-Sleep" type of module may indicate that the new module will be used to assess the sleep health/quality of one or more users. In some cases, an option may be presented to the researcher/admin 402 to create a new type of module or a custom module.

In response to selecting the type of module 410, the server system 110 may send a module template 412a (Module Template A) from the module data 432. The module template 412a may correspond to the type of module 410 selected by the researcher/admin 402. For example, after selecting the type of module 410, the administrator device 404 may send an indication of the type of the module 410 to the server system 110. The server system 110 may select the module template 412a as a template corresponding to the type of module 410. For example, the module template 412a may be a template for sleep modules.

After the receiving the module template 412a, the client device 404 may present characteristics of the module template 412a on the interface 406. Optionally, the interface 406 may provide a preview (e.g., a rendered view or other visual indication) of the form or survey that the template 412a represents. The researcher/admin 402 may proceed to complete or change different aspects of the module template 412a, to create a customized module template 412b. For example, under a contents area 414 of the module template 412b, the researcher/admin 402 has used a dropdown menu to indicate, with a selection of "no," that the new module does not have multiple sections. In the contents area 414, the researcher/admin 402 may be able to add and customize different prompts for the new module.

As shown, the researcher/admin 402 can enter text to present to participant(s) completing the new module in a text field. For example, the researcher/admin 402 can enter the text "How many hours did you sleep last night?" in the text field for the first prompt. The researcher/admin 402 can further indicate a type of prompt, e.g., corresponding to the type of response that is expected from a participant completing the new module. For example, as shown, the researcher/admin 402 has used to a dropdown menu to select a numerical prompt type, providing that a participant must provide a numerical value when responding to the first prompt. If for example, a participant provides a non-numerical response while responding to the first prompt of the new module, an error may occur and the participant may be presented with a notification requesting that they provide a numerical response (e.g., potentially within certain value limits).

The researcher/admin 402 may further specify value limits, e.g., when a numerical prompt type is selected. For example, the researcher/admin 402 may set the maximum acceptable value to twenty-four, and the minimum acceptable value to zero. If, for example, a participant provides a response value outside of these bounds, an error may occur and the participant may be presented (e.g., by the client device 104 shown in FIG. 1) a request to provide a different response within the value limits.

The researcher/admin 402 may also provide and/or customize the scoring criteria for the prompts using the interface 406. For example, the researcher/admin 402 may add scoring criteria for the first prompt that indicates if a user provides a response value greater than eight, the user will receive a score of three for the first prompt. The researcher/admin 402 may use an interface to add additional scoring criteria. In response to selecting the interface element, the researcher/admin 402 may be presented a list of different types of scoring criteria, such as specific value conversions (e.g., converting a particular response to a particular score), Boolean operators (e.g., used to create outline thresholds and/or ranges), equations (e.g., which would allow the researcher/admin 402 to enter a specific equation used to generate a score based on a response), etc. The scoring criteria may be considered scoring parameters and may alternatively be included in the scoring parameters area 416.

The contents area 414 may also include an interface element that allows the researcher/admin 402 to add a prompt to the module. When the researcher/admin 402 select the interface element, they may be presented a blank prompt form (e.g., similar to first prompt with the fields being empty) or an option for a blank prompt. Additionally or alternatively, the researcher/admin 402 may be presented with a list of previously generated prompts, such as those that have been used in previously generated sleep type modules, and/or those that are otherwise recommended for the new module (e.g., by the server system 110).

The scoring parameters area 416 may include, for example, one or more score thresholds and corresponding actions or determinations. For example, the template 412a may include a score threshold for ending the module. The researcher/admin 402 may fill out the field corresponding to this score threshold with a value of ten. Accordingly, once a cumulative score of ten is achieved, the module may be automatically ended or marked as complete. If, for example, the score threshold is not achieved after the user has provided responses to all prompts, the server system 110 may determine that the user is at risk of insomnia or another sleep-related medical condition such as sleep apnea. The researcher/admin 402 may be able to add, remove, or replace scoring parameters in the scoring parameters area 416. For example, the researcher/admin 402 may add a first score threshold for concluding that the user is not at risk of sleep insomnia, and a second score threshold for concluding that the user is not at risk of sleep apnea.

The collection parameters area 418 may include, for example, one or more rules for determining if user responses are valid and/or if score adjustments need to be made. For example, the template 412a may include a collection parameter that requires a minimum or maximum response time for a user to provide a response to a prompt. The researcher/admin 402 may select a Boolean operator from a dropdown menu to indicate that the rule is for a minimum response time, and may further fill out a numerical field that corresponds to a number of seconds with a value of 0.8. Accordingly, if a user responds to any prompt of the new module in less than 0.8 seconds, an error may occur and the user may be notified that they should take additional time to consider the question. The researcher/admin 402 may be able to add, remove, or replace collection parameters in the collection parameters area 418. For example, the researcher/admin 402 may add a collection parameter that indicates, for the first prompt, sensor data corresponding to sleep should be acquired if available from a device of the user (e.g., a fitness tracker, smart phone, sleep sensor, etc.).

A participant(s) area 420 of the template 412b may include recommended and/or specified users. The participant(s) area 420 may include one or more participants that have been recommended by the server system 110 to complete the new module based on the user profiles 434. For example, the server system 110 may recommend all participants whose user profiles indicate that they have been diagnosed with a sleep-related medical condition (e.g., insomnia, sleep apnea, etc.). Similarly, the server system 110 may recommend all participants whose user profiles indicate that they have recently (e.g., in the past month, past six months, past year, etc.) completed a sleep-related module.

As an example, the server system 110 has recommended a Participant A to complete the new module based on the participant having been previously diagnosed with sleep insomnia, and having previously completed a sleep module (Sleep A) and a mental health module (Mental B).

The researcher/admin 402 may also specify particular participants that should be tasked with completing the new module in the participant(s) area 420. For example, the researcher/admin 402 may be able to type names of particular participants. Similarly, the researcher/admin 402 may use the interface 406 to select particular participants from a list of registered participants, or select particular participants from a list of recommended participants (e.g., recommended by the server system 110).

In some cases, one or more fields of the template 412b are pre-filled. For example, the fields corresponding to the first prompt may have been pre-filled as part of the template 412a. Of note, the maximum value field may have been pre-filled with a value of twenty-four because the first prompt is asking for a number of hours and there is the maximum number of hours in a day. Similarly, the field for the cumulative score to end the module of the scoring parameters 416 may have been pre-filled with the value of ten.

The researcher/admin 402 may interact with an interface element 422 to save the new module, e.g., to save as a draft for later revisions. Alternatively, the researcher/admin 402 may select the interface element 424 to export the new module to the server system 110 where it can be distributed to one or more participants. If the researcher/admin 402 attempts to export an incomplete module, an error may occur and the researcher/admin 402 may be presented a corresponding notification indicating the error that has occurred. For example, the researcher/admin 402 here may be presented an error for trying to export the new module that has a score threshold of ten but only a single prompt with a maximum score of three (e.g., therefore the score threshold could never be reached in the module's current state).

Once the researcher/admin 402 has successfully finalized the characteristics of the new module, the content and parameters selected for the module are provided as module specifications 439 to the server system 110. The server system can then use the specifications 439 to generate and store module data 440 (Sleep B Module) that the server system 110 can then use to enable client devices to present the module. The module data 440 may be a form data package as described above with respect to FIG. 1. The server system 110 may store the module data 440 along with any other modules created by the researcher/admin 402 or others. The server system 110 may enable a client device to present the module by providing a form data package that the client device can interpret and run, e.g., a self-contained package enabling the presentation and scoring of the module. As another example, the server system 110 may use the module data 440 to server interactions of the module, where portions of the module are served incrementally to the client device during presentation, and the server system 110 performs the scoring and evaluation of responses.

Figure 4B:
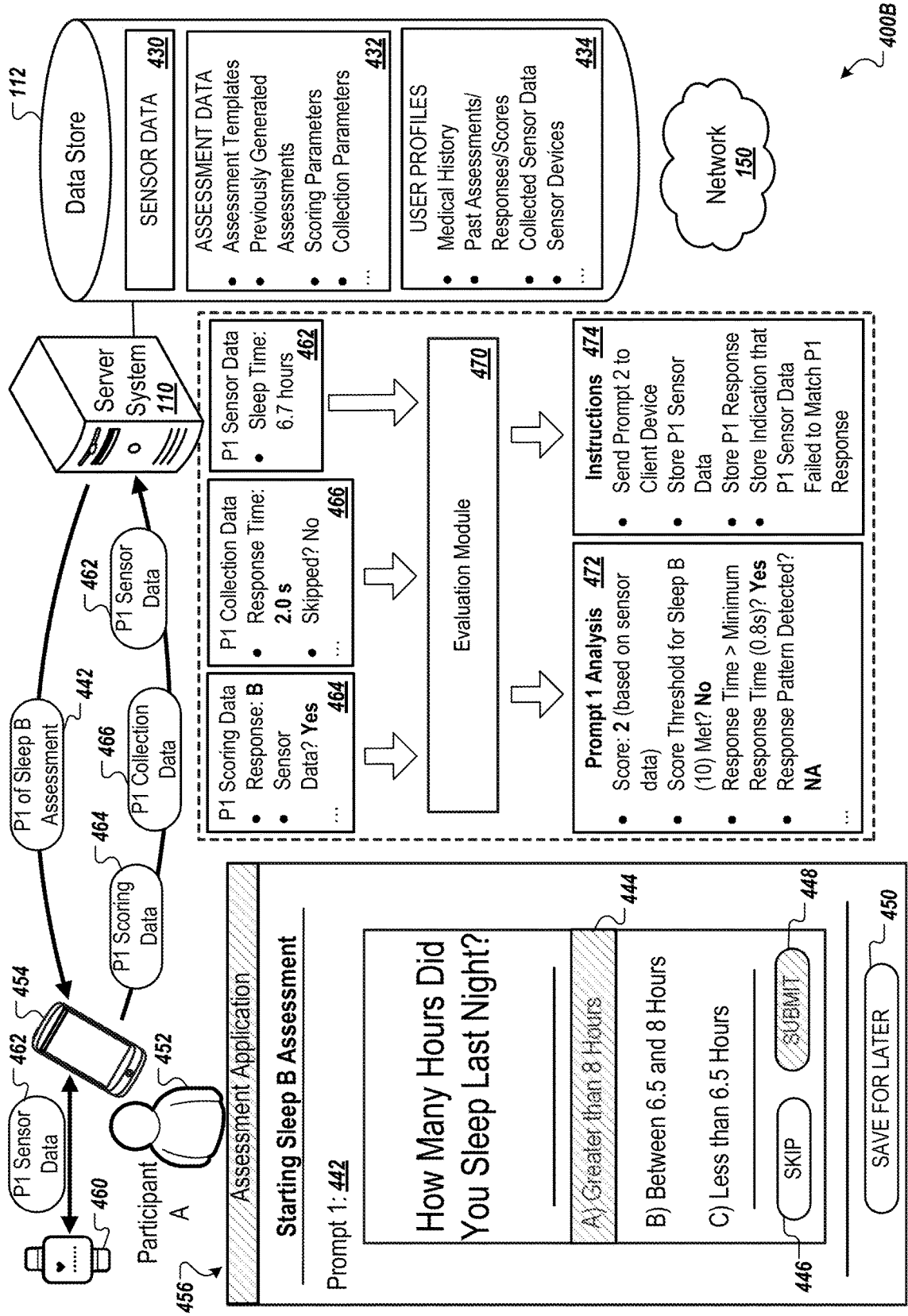
FIG. 4B is a diagram that illustrates an example system for dynamically scoring and presenting an interactive module.

FIG. 4B is a diagram that illustrates an example system 400B for dynamically scoring and presenting the module 440. The system 400B includes the server system 110, the data store 112, and a client device 454 of a participant 452 (Participant A). The client device 454 may be capable of receiving various inputs from the participant 452 and sensor data from a sensing device 460. The sensing device 460 may be, for example, a smart watch or a fitness tracker.

The server system 110 may send the module 440 discussed above with respect to FIG. 4A or a portion of the module 440 to the client device 454. For example, as shown, the server system 110 may send the first prompt 442 of the module 440 to the client device 454. Alternatively, the server system 110 may generate and send a form data package to the client device 454 that contains the entirety of the module 440, or a portion of the module 440 (e.g., along with scoring parameters and collection parameters that the client device 454 may use to score the participant 452's responses).

In response to receiving the prompt 442, the client device 454 may present the prompt 442 on a module interface 456 of the client device 454. The module interface 456 may correspond to a mobile application for conducting modules that is presently running on the client device 442. As shown, the prompt 442 is displayed in the interface 456.

The prompt 442 may include one or more predetermined responses. For example, the prompt 442 includes three multiple choice options that the participant 452 can select from when responding to the prompt 442. As shown, the participant has selected a first choice 444 "(A) Greater than 8 Hours") from among the multiple choices.

The interface 456 may also present various interface elements in addition to the prompt 442. For example, the interface 456 may present an interface element 450 that allows the participant 452 to save their current progress in the module 440 so that they can return at a later time to complete the module 440. As another example, the interface 456 may present an interface element 446 for skipping the prompt 442. If the participant 452 selects the interface element 446, a subsequent prompt of the module 440 may be presented to the participant 452. Specifically, the client device 454 may generate a request for a new prompt of the module 440 that it sends to the server system 110, e.g., along with an indication that the prompt 442 was skipped. In response, the server system 110 may send the client device 454 a different prompt of the module 440 to present to the participant 442. The prompt 442 may later be presented to the participant 452 after a threshold number of other prompts have been responded to, a threshold amount of time has passed, or as the last prompt. In some cases, the prompt 442 is not later presented to the participant 452, e.g., if a score threshold for ending the module 440 is reached.

The interface 456 may also include an interface element 448 that allows the participant 452 to submit their current response selection. After the interface element 448 has been selected, the participant 452's response (e.g., scoring data 464) and corresponding information (e.g., collection data 466) may be sent to the server system 110. One or more additional actions may also be performed, such as obtaining sensor data from the client device 454 or the sensing device 460. For example, in response to selecting the interface element 448, the client device 454 may request sensor data 462 from the sensing device 460 that specifies or indicates the number of hours that the participant 452 slept last night. For example, the sensor data 462 may indicate that the participant 452 actually slept for 6.7 hours last night, in contrast to the participant 452's response of greater than eight hours.

The client device 454 may also track additional information, such as the participant 452's response time for the prompt 442 (e.g., time elapsed between the prompt 442 being presented to the participant 452 and the participant 452 selecting the interface element 448). This information may be part of the collection data 466 that is sent by the client device 454 to the server system 110 along with the sensor data 462 and the scoring data 464 that contains the participant 452's response to the prompt 442.

In addition to the responses provided by the participant 452, the scoring data 464 may include an indication of whether sensor data was obtained that is applicable to the prompt 462. For example, the scoring data 464 may include an indication that sensor data was obtained that may be used to supplement or override the participant 452's prompt 442 response.

In some cases, the scoring data 464 does not include a response. For example, the client device 454 may determine that a response is not needed if there is available sensor data that can be used in place of a response to the prompt 442. The client device 454 may avoid presenting the prompt 442 to the participant 452, and, instead, may send the sensor data directly to the server system 110. The server system 110 can proceed to determine a score for the prompt and/or one or more other prompts using the sensor data.

After receiving the scoring data 464, the collection data 466, and, optionally, the sensor data 462, the server system 110 uses an evaluation module 470 to generate one or more score(s) for the prompt 442 and/or to make determinations that relate to the presentation of the module 440. The evaluation module 470 may include one or more algorithms, such as one or more machine learning models or static algorithms that it can use to generate the score(s) for the prompt 442 and/or to indicate how the presentation of the module 440 should proceed. The one or more algorithms may include or be based on predetermined scoring parameters and/or collection parameters for the module 440. For example, the server system 110 may provide the scoring data 464, the collection data 466, and the sensor data 462 the evaluation module 470 as input to one or more algorithms to the evaluation module 470. The evaluation module 470 may use this information to generate an analysis 472 for the prompt 442, and instructions 474 that describe actions that should be taken by the server system 110, the client device 454, or a combination of the client device 454 and the server system 110.

The analysis 472 may include scores generated and/or previously generated for the current module. These scores may include one or more scores that are generated for the prompt 456, and/or cumulative scores for the module (and/or different sections of the module). The scores themselves may be indicative of traits that the participant 452 possesses, such as their physiological health. The server system 110 may alternatively or additionally determine quality scores when generating the analysis 472. The quality scores may indicate the quality of data collected during the module, such as a quality of the participant 452's response 444. As an example, a quality score for the prompt 456 may be lowered relative to a response time of the participant 452 such that the quicker the user responds (e.g., under a threshold response time), the lower the quality score for the prompt 456. Similarly, if the user was presented the same prompt 456 earlier in the module (or a different version of the same prompt possibly with different interface elements) and gave a different response (e.g., seven hours), then the server system 110 may determine a low quality score for the prompt 456 to account for the inconsistent responses. Alternatively, the server system 110 may determine the responses to be invalid, and, therefore, may not even determine a score for the participant 452's response 444.

In generating the analysis 472, the evaluation module 470 may determine that the sensor data 462 should be used to generate the score for the prompt 442 over the participant 452's response in the scoring data 464. This determination may be based on sensor data being, by default, trusted over participant responses. The determination may also or alternatively be based on the device used to obtain the sensor data and the participant 452's consistency using the device (e.g., as may be indicated in the user profiles 434). For example, if the sensing device 460 is known to produce sufficiently accurate sensor data, the evaluation module 470 may determine that the sensor data 462 should be used to score the prompt 442 over the response 444.

Using the sensor data 462, the evaluation module 470 determines a score of two for the prompt 442. The evaluation module 470 may proceed to compare the score to one or more scoring parameters for the module 440, such as a score threshold for the module 440 to determine if the module 440 should be ended (e.g., marked as successfully completed). As shown, it is determined that the score threshold is not yet met. The score for the prompt 442 can then be added to cumulative score for the module 440 that the evaluation module 470 tracks.

In generating the analysis 472, the evaluation module 470 may compare the collection data 466 to one or more collection parameters for the module 440. For example, by comparing the participant 452's response time of 2.0 seconds to a minimum response time requirement, the evaluation module 470 determines that the minimum response time was not violated. In some cases, the evaluation module 470 may not compare the collection data 466 to the corresponding collection parameters if only the sensor data 462 is being used to score the prompt 442.

The evaluation module 470 may also be used to detect patterns in the participant 452's responses and corresponding information. For example, the evaluation module 470 may identify correlations between response times or ranges of response times and the participant 452's response accuracy. If, for example, the evaluation module 470 determines that the participant 452's responses have less than a fifty percent chance of being accurate when the corresponding response time is less than one second (e.g., where accuracy is confirmed by leveraging sensor data), then the evaluation module 470 may generate instructions to increase the minimum response time from 0.8 seconds to 1.0 seconds. Alternatively, the evaluation module 470 may reduce the scores for prompts when the response time is less than 1.0 second to account for the increased risk of inaccuracy. For example, the evaluation module 470 may apply a weight of 0.5 to a prompt score to account for the 50% accuracy likelihood. The evaluation module 470 may also save an indication of this behavioral pattern as part of the user profiles 434 for the participant 452. Because only one response has been received at this point in the module 440, the evaluation module 470 is yet unable to detect any patterns corresponding to the participant 452. However, that evaluation module 470 may note that the response 444 did not match or substantially match the sensor data 462.

The evaluation module 470 may proceed to generate the instructions 474 based on the analysis 472. For example, the evaluation module 470 may generate instructions to send a second prompt to the client device 454 since the score threshold for completing the module is not met. Instructions may also be generated for storing the sensor data 462 as part of the sensor data 430 and/or the user profiles 434, and/or the participant 452's response 444 as part of the user profiles 434. The evaluation module 470 may optionally generate instructions for storing an indication that the sensor data 462 did not match or substantially match the response 442. However, the evaluation module 470 may wait to generate these or similar instructions until more data points can be obtained (e.g., from additional responses of the participant 452) that indicate that the participant 452 often or consistently provides inaccurate responses.

In some cases, if a determination is made that a participant often or consistently provides inaccurate responses, the evaluation module 470 may generate instructions that modify the collection and/or scoring parameters for the module 440 to emphasize the importance of sensor data over the participant 452's responses, and/or generate a recommendation that the participant 452 start using one or more sensing devices to collect additional sensor data.

In some cases, the server system 110 (or the client device 454) determines one or more quality scores. For example, the server system 110 may track a cumulative quality score for the module that serves as indicator of the quality of data collected during the module (e.g., user responses, sensor data, etc.). The server system 110 may also determine a quality score for each of the prompts, including the prompt 456. The quality score may be based on, for example, the participant 452's response time, response time compared to a one or more immediately preceding response times, response time compared to a typical response time. The quality score may also be affected by determinations as to whether the participant 452's responses were consistent with their previous responses (e.g., previous responses in the current module, or previous responses as provided in his profile of the user profiles 434) or collected sensor data. As an example, if the sensor data 462 collected from the sensing device 460 indicates that the participant 452 slept six hours last night instead of the more than eight hours that the participant 452 indicates in their response 444, the server system 110 may determine a lower quality score corresponding to the prompt 456 due to the inconsistency. For example, the server system 110 may determine a quality score of 0.6 (e.g., out of a maximum of 1.0) for the prompt 456. The server system 110 may proceed to add the 0.6 quality score to a cumulative quality score for the module.

In some cases, a quality score may be lowered if a user response is out of range. For example, instead of being presented multiple choice options in the prompt 456, the participant 452 may be presented a field where they can enter the number of hours. If they enter a negative value or a value greater than twenty-four, then the server system 110 may determine that the participant 452's response was out of range. In response to this determination, the server system 110 may lower a score determined for the prompt 456 (or set the score to zero for the prompt 456), and/or may determine a lower quality score for the prompt 456 (or set the quality score to zero for the prompt 456). The server system 110 may further generate and send instructions to the client device 454 to present the prompt 456 a second time and ask the user to provide a different response (e.g., optionally with an indicator stating that their previous response was out of range).

In some cases, the client device 454, instead of the server system 110, performs the analysis 472 and/or generates the instructions 474. For example, the client device 454 may receive a form data package from the server system 110 that includes data corresponding to one or more prompts, and corresponding rules (e.g., scoring parameters and collection parameters). The form data package may also include, for example, a profile for the participant 452. The client device 454 may use the contents of the form data package to present one or more prompts of the module, to score the participant 452's responses, and/or to determine a quality score based on data collected. The client device 454 may proceed to make one or more determinations, e.g., using the contents of the data package. For example, the client device 454 may use the contents to determine what prompt to present next, to determine if the participant 452 needs to reconsider a prompt, to determine when to switch sections of the module, to determine if the participant 452 failed a section and/or the module itself, etc.

Figure 5:
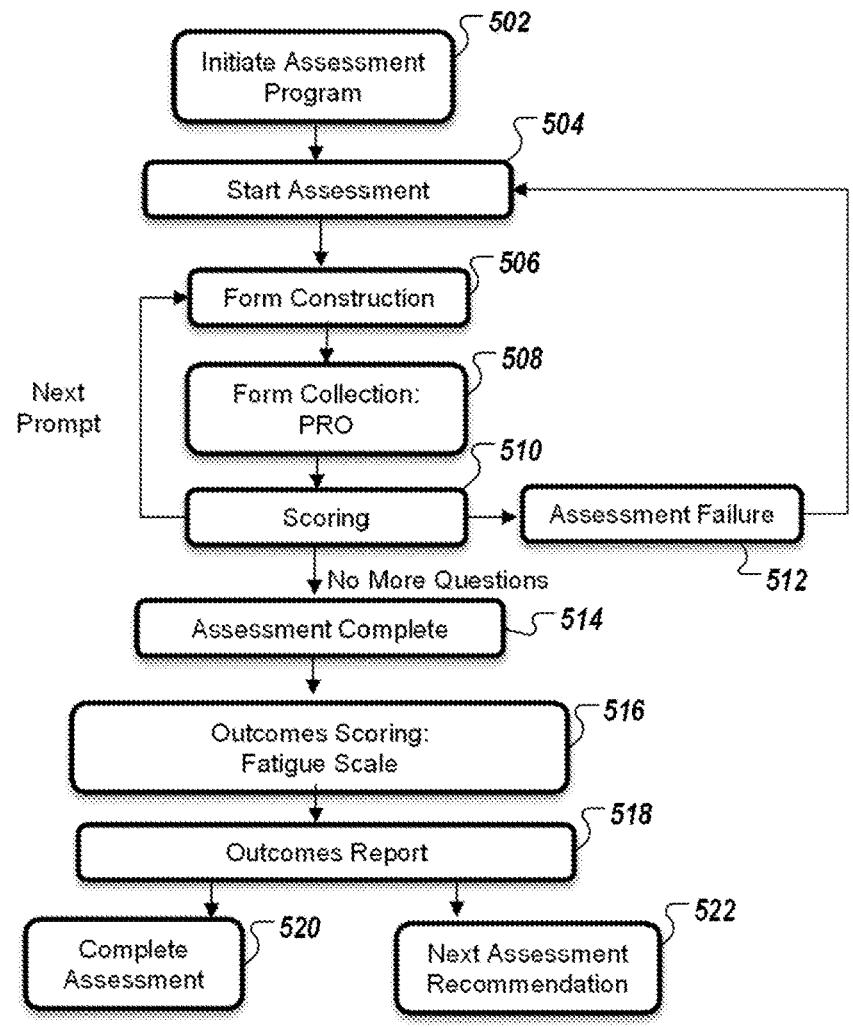
FIGS. 5-7 are flowchart diagrams that illustrate example processes for providing and scoring interactive modules.

FIG. 5 is a flowchart diagram that illustrates an example process 500 for conducting an assessment using an interactive module. The process 500 may be performed in whole or in part by the server system 110 shown in FIG. 1 and FIGS. 4A-4B, the client device 104 shown in FIG. 1, and/or the client device 454 shown in FIG. 4B.

The example of FIG. 5 shows an example for a memory recall test or mental health test. The example describes form construction and a model for scoring during the assessment. The scoring is used to determine whether additional questions are required and to determine the overall outcome of the assessment module. In addition, data collection parameters and scoring parameters can be used to determine whether the confidence and quality of the test is suspect, so the system can re-run the test if appropriate. Table 1 shown below describes inputs related to an assessment module that specifies an EMA for memory recall, utilizing a "brain fog" test tool as a method for assessing and scoring on a fatigue scale related to the brain fog test.

The process 500 includes initiating an assessment program (502). For example, with respect to FIG. 1, the client device 104 may run a mobile application for conducting assessments. The application may be opened in response to receiving the form data package 120 from the server system 110 or another message from the server system 110, or through user action. As another example, the server system 110 itself may run an assessment program to generate and deliver contents of interactive modules.

The process 500 includes starting an assessment (504). For example, with respect to FIG. 1, the client device 104 may start an assessment by extracting the contents of the form data package 120. Alternatively, the client device 104 may start the assessment 104 by presenting a portion of the assessment on an interface of the client device 104, such as predetermined first prompt of the assessment. The assessments can be managed by the server system 110 and provided one interaction or set of interactions at a time. For example, starting the assessment can involve the server system 110 loading a saved module that a researcher or administrator created, as well as information about the user the module will be presented to.

The process 500 includes constructing the form of the assessment (506). For example, the client device 104 may use the extracted contents of the data package 120 to determine how the assessment, or portions of the assessment should be presented to the user. As another example, the server system 110 can determine, based on saved module data, a form or UI element to be presented, and then generate data (e.g., HTML, XML, JSON, text, instructions, media, etc.) defining that form element to serve to the client device 104. Constructing the form of the assessment may include, for example, determining an order for presenting different prompts of the assessment, or an order for presenting different sections for the assessment. Similarly, constructing the form of the assessment may include determining one or more prompts of the assessment that do not need to be presented to a user, or sections of the assessment that do not need to be presented to the user. For example, if the client device 104 determines that it has sufficient sensor data to conclude that a user is not at risk of sleep condition, the client device 104 may determine that it does not need to present prompts in the sleep quality section of the assessment to the user.

In some cases, constructing the form of the question may be based on a user profile for a user that will take the assessment. For example, a user profile may indicate that a user has been previously diagnosed with depression. As such, the client device 104 may determine that it should presents prompts corresponding to a mental health section of the assessment at the beginning of the assessment or at the end of the assessment, when the user is more likely to be paying attention.

The process 500 includes collecting inputs for the assessment (508). For example, the client device 104 may collect inputs from a user through an interface of the client device 104. Similarly, the server system 110 can collect inputs provided by the client device 104 over the network. The inputs may include numerical data, text data, and interface element selection. The inputs may, in some cases, include sensor data obtained using sensors of the client device 104 or from one or more other sensing devices, such as a fitness tracker or a smartwatch. As an example, the inputs may include participant reported outcomes from a clinical trial. The inputs can include contextual data or data describing user actions in responding, such as the time between presentation of a prompt and a user response, how many times a user changed their response before submitting, sensor data collected while the prompt was displayed, etc.

The process 500 includes scoring at least a portion of the assessment (510). For example, the client device 104 may use one or more scoring parameters from the form data package to determine a score for the first prompt of the assessment. The client device 104 may compare the user's response to the first prompt to the scoring parameters to determine a score. In some cases, if the user's response does not meet the collection parameters, the client device 104 may determine a score of zero for the first prompt. Alternatively, the client device 104 may ask the user to review their response and resubmit. The server system 110 may score the response, for example, to generate a score and also evaluate the score with respect to a reference (e.g. a threshold, range, prior score for the user, distribution of scores for other users, etc.).

The scoring parameters may be used to generate a score that indicative of the participant's traits, such as their physiological health. The scoring parameters may additionally or alternatively provide for generating a quality score that indicates the trustworthiness and/or validity of the data collected.

After a response to a prompt is scored (e.g., by the client device 104 or the server system 110), the client device 104 or the server system 110 may again perform form construction by selecting a new prompt to present to the user and/or a new section of the assessment to have the user start.

Scoring at least a portion of the assessment module may include tracking one or more cumulative scores. For example, the client device may track a cumulative score for the entire module, and then cumulative scores for each section of the module. The client device 104 may compare these cumulative scores to corresponding scoring parameters to determine one or more actions to perform, such as switching sections of the module or determining that the module is complete.

The process 500 optionally includes determining that the assessment has failed to achieve the intended goal (512), e.g., collection of data, assessment of a capability or attribute of the user, etc. As shown, this can be a result of the scoring that is done during the course of the presentation of the module, e.g., during the series of prompts or interactions of the module, and not necessarily only at defined points in the presentation of the module, such as the completion of the module, a section of the module, or an element. Even during the response period for a specific element, the client or server may determine that factors may cause the element or the module as a whole to be unreliable, for example, due to erratic input patterns, sensor data that is absent or inconsistent, lack of input, etc.

An assessment may be determined to fail if, for example, it is determined that a user's responses are unreliable. For example, if the response time for the user's inputs consistently does not meet a minimum response time, or if the user's inputs are the same for a threshold number of inputs (e.g., same response of choice A was provided for the last five questions, or the same response of choice A was provided for the last five questions within the last ten seconds). Similarly, a user's inputs may otherwise be determined to be unreliable and, therefore, a reason for determining that the assessment has failed. For example, the client device 104 may determine that the user's inputs are unreliable if the user's inputs are consistently shown to be incorrect when compared to collected sensor data.

In some cases, determining that the assessment has failed may include determining that one or more score thresholds have not been met after all or subset of prompts have been responded to. For example, if a score threshold (e.g., a quality score threshold) for completing the assessment is not met after the client device 104 has presented all prompts of the assessment to the user and the corresponding responses have been scored, the client device 104 may determine that the assessment has failed.

In response to determining that the assessment has failed, the client device may request that the user retake the assessment. The form of the assessment or for a particular portion of the assessment, such as a particular section, may be modified in an effort to get the user to successfully complete the assessment. Alternatively, the client device 104 may recommend an alternate assessment for the user to take.

In some cases, failure may be detected or a failure result assigned when particular patterns and/or events occur. For example, if the user fails to meet a minimum response time for eight questions in a row, the client device 104 may end the assessment and determine that the user has failed the assessment.

The process 500 includes determining that the assessment is complete (514). As an example, the assessment may be determined to be complete after the user has responded to all prompts in the assessment. Additionally or alternatively, the assessment may be determined to be complete after one or more score thresholds have been met. For example, the client device 104 shown in FIG. 1 may mark the assessment as complete once a score threshold corresponding to the end of the assessment met based on a tracked cumulative score for the assessment. Similarly, the assessment may be complete after the score threshold for each of the sections of the assessment are met, e.g., using corresponding section cumulative scores tracked by the client device 104.

In some cases, successful completion may depend on a variety of criteria being met. For example, the client device 104 or the server system 110 may determine that a user has successfully completed an assessment if they have responded to at least a threshold number of prompts and the corresponding responses had an average quality score above 0.8/1.0.

The process 500 includes scoring the outcomes of the assessment (516). With respect to FIG. 1, the client device 104 may compare the inputs and/or the determined scores to condition criteria. For example, the client device 104 may compare the cumulative score for a cardiovascular section of the assessment to a threshold score that corresponds to a risk of the user having high blood pressure. If, for example, the cumulative score does not meet the threshold score, the client device 104 may conclude the user is at risk of having high blood pressure. The client device 104 may additionally or alternatively use sensor data and/or the particular responses to come to the conclusion that the user is at risk of having high blood pressure. For example, the client device 104 may use sensor data to increase the confidence in its conclusion (or to revoke its conclusion) that the user is at risk of having high blood pressure.

The process 500 includes reporting the outcomes of the assessment (518). The outcomes of the assessment may be reported to the user taking the assessment. For example, after completing the assessment, the client device 104 may display a notification indicating that the user is at risk of high blood pressure and should consult a cardiologist. The outcomes may also be reported to researchers, such as those conducting a clinical trial that the user is a participant in. Where the outcomes of the assessment include a determination with a sufficient confidence that the user is at risk of a serious health condition or has a serious health condition, the outcomes may be reported directly to a physician or to emergency services. For example, the outcomes may be sent to the server system 110 for storage on the data store 112. The server system 110 may proceed to contact a physician for the user and/or emergency services.

The process 500 optionally includes reporting that the assessment is complete (520). For example, the client device may display a notification on the interface 122 indicating the user has successfully completed the assessment. The client device 104 may send an indication that the user has successfully completed the assessment to the server system 110. In response, the server system 110 may update a user profile of the user to include the indication (and/or the responses provided by the user, or the corresponding scores), and may send the indication to researcher conducting a study that the user is a participant of.

The process 500 optionally includes reporting a next assessment recommendation (522). For example, if the outcomes indicate that the user is potentially at risk of a medical condition, the client device 104 (or the server system 110) may recommend that the user complete another module related to the medical condition. Similarly, if the outcomes of the assessment indicate that more information is required to make a determination as to whether the user is at risk of a medical condition or has a medical condition, the client device 104 (or the server system 110) may recommend that the user completes an assessment containing prompts that will elicit the data required to make those determinations.

The table below illustrates example input data and corresponding collection parameters and scoring parameters. The collection parameters may provide various criteria for determining the validity of the input data. For example, the collection parameters may provide that repeated prompts are permitted for prompts that correspond to participant reported outcome (PRO). These may be used to determine, for example, if the user is paying attention and/or suffering from fatigue. If the participant gives a different response to the same question, for example, then the client device 104 or the server system 110 may determine that the response is invalid (e.g., and therefore not be used for scoring). As shown, the scoring parameters may outline how an assessment may be passed or failed. For example, a participant providing PRO will be determined by the client device 104 or the server system 110 to fail the test if they provide the same response within in ten seconds for ten prompts in a row.

TABLE 1

| Input Data | Collection Parameters | Scoring Parameters |
| --- | --- | --- |
| Participant Reported Outcome (PRO) | Brain Fog Test Within the Test Length Time Randomization allowed Repeat Questions Allowed | Same answer applied within 10 seconds for 10 prompts fails the test Expected average response time should increase throughout the test based on measures of fatigue |
| Test Length | Time Specified (e.g. based on average response time of 10 seconds per question and up to 1 minute, where the total question set is 25 would typically yield between 4 minutes and 25 minutes, thresholds could be thus set to no less than 2 minutes and no greater than 50 minutes.) | Incomplete result requires retesting Speedy entry is considered an incomplete result, where time is less than 2 minutes Suspending the test is considered an incomplete result, where test time is greater than 50 minutes. |
| Schedule | Once Only | Not available after successful completion |

In an example, data indicating the parameters described in Table 1 above may be used in the process 500. For example, the client device 104 (or the server system 110) may use the types of data indicated in column 1 (Input Data) during form construction and/or before collecting inputs for an assessment, a particular portion of the assessment, or a particular prompt of the assessment. As illustrated in FIG. 5, after a response and/or data is acquired for a particular prompt, the form of the assessment is constructed (e.g., a subsequent prompt is selected by the client device 104 or the server system 110 to be presented to the participant), and the a form collection is performed. The type of form collection may be based on the particular prompt or type of prompt that is selected during the form construction. For example, as shown, the form collection for the next prompt (or for a section of the assessment, or the entire assessment) may be participant reported outcome (PRO). Based on the type of form collection being PRO, the client device 104 may anticipate, for example, responses in the form of multiple choice selections, field entries (e.g., text types into text input fields), and other types of inputs discussed in more detail above.

The client device 104 or the server system 110 may also use data indicating data collection parameters, as described in column 2 (Collection Parameters), to determine, for example, if the data collected (e.g., the responses, sensor data, electronic medical records, etc.) during the assessment is valid. Finally, if the responses are valid and appropriately collected, the client device 104 or the server system 110 may use parameters as described in column 3 (Scoring Parameters) to determine one or more scores corresponding to the particular prompt, and/or to determine if the user has successfully completed the assessment. These one or more scores may be a score that indicative of the user's traits, such as their physiological health. Similarly, these one more scores may include a quality score that indicates the quality of data collected (e.g., the trustworthiness of the user's responses based on their previous responses, past responses, response time, etc.).

Figure 6:
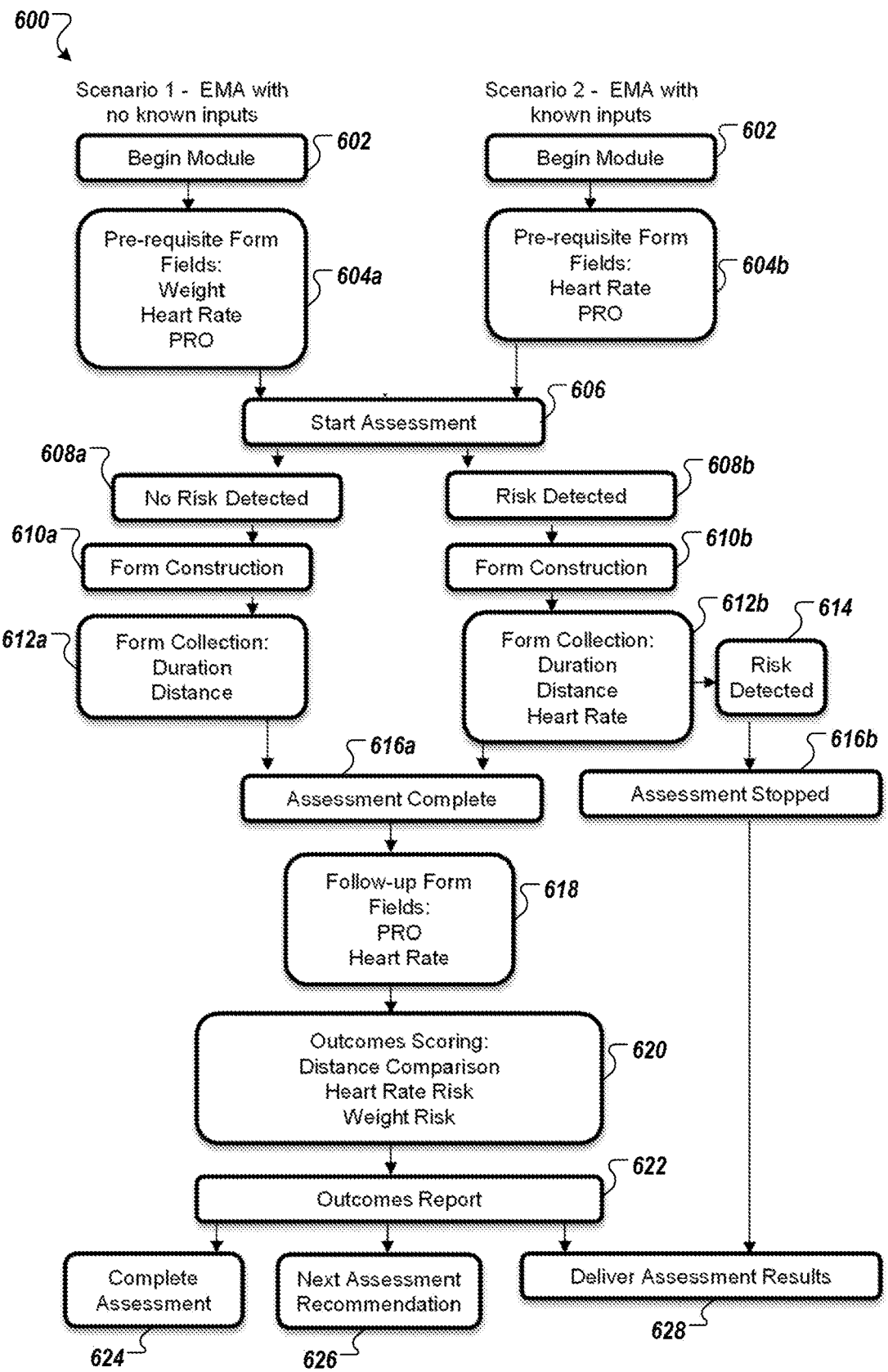

FIG. 6 is a flowchart diagram that illustrates an example process 600 for conducting an assessment using an interactive module. The process 600 may be performed in whole or in part by the server system 110 shown in FIG. 1 and FIGS. 4A-4B, the client device 104 shown in FIG. 1, and/or the client device 454 shown in FIG. 4B.

The example of FIG. 6 shows the use of an assessment that includes a walking test as a measure of a user's physical health and capability. The example describes the ability to retrieve data and modify a form based on previously-collected data. It also describes the ability to apply constraints for different forms or tests in the module with separate sets of parameters for each form or test. Scoring parameters define conditions that, when detected, may cause the test to be stopped prematurely in order to deliver an immediate EMI. Table 2 below describes inputs related to a module that specifies an EMA for reporting an observed (e.g., sensed) physical measure, such as exercise performance (e.g., distance, balance, etc.) during a timed and guided activity.

The example shows different branches that can be used for different situations. For example, users having different sets of data available about them prior to beginning interaction with a module can be shown different sets or types of interactions. For example, there can be different "entry points" or versions of a module presented depending on which information about a user is already available in a user profile, health records, etc. for the user.

The process 600 includes starting an interactive module (602). For example, with respect to FIG. 1, the client device 104 may begin processing a form data package 120 from the server system 110. As another example, the server system 110 may access module data and begin generating and serving data for the module.

The process 600 includes identifying data related to the module that has already been acquired (604). This already-captured data is indicated as pre-requisite form fields represent types of data that is desired, but which may have been already collected. The steps 604a and 604b can represent the retrieval, from user profile data, for two different users, where the system determines that different sets of data are available for the two users. In step 604a, a user has previously provided weight, heart rate, and a patient-reported outcome (PRO). In step 604b, a user has provided heart rate and a PRO, but has not provided weight data. The module can be started with either of these combinations of pre-requisite data available (or other combinations potentially), but the behavior of the module can be changed depending on which data is available. For example, without weight data, the system may ask the user additional questions, which may be about weight or about other health factors. Similarly, the scoring may be different depending on which data is available.

In some cases, previously collected data can be used to change which items are presented in a user-fillable form in the module. For example, the server system 110 may retrieve information from a user profile of the user profiles 434. The information may include a weight of the user. Based on this information, the server system 110 can update the form to remove form fields corresponding to the weight of the user. That is, any prompts that previously requested that the user enter their weight or stand on a scale that can wirelessly communicate with a client device, may be removed from the module. The retrieved information may be used in place of the fields or the fields, or the entire element related to the fields can be omitted. That is, the retrieved information may be used to fill in or partially fill in the module for the user beforehand. Whether this occurs may depend on the reliability of the retrieved information. For example, if the weight of the user was taken less than three months ago, it may be considered by the server system 110 to still be reliable. Accordingly, the form fields may correspond only to the data of the user that must be collected because the data is not otherwise available, or because it is determined to be unreliable (e.g., due to age, due to source, etc.).

The process 600 includes starting a module (606). For example, with respect to FIG. 1, the client device 104 may start a module by extracting the contents of the form data package 120. Alternatively, the client device 104 may start the module 104 by presenting a portion of the module on an interface of the client device 104, such as predetermined first prompt of the module. Regardless of which of multiple paths is used to reach step 606, e.g., 604a or 604b, either of the paths following step 606, e.g., 608a or 608b may be followed depending on the information detected.

The process 600 includes determining a different set of interactive elements depending on whether no health risk is detected (608a) or if a health risk is detected (608b). These determinations can be based on a user profile and data from prior module interactions of the user. For example, the server system 110 may use previously obtained information corresponding to a user to determine if the use is at risk of a particular condition (e.g., of a particular health condition). The server system 110 may make this determination by setting, in collected data for the module, at least some data retrieved in the pre-requisite or prior data. For example, if weight is to be gathered by the module, and weight data is already available, the system can insert the prior-collected weight value as a weight value provided as a result of this use of the module. This information may be obtained from a user profile for the user of the user profiles 434, and may include, for example, previous responses by the user, medical health records for the user, past modules taken by the user, collected sensor data of the user (e.g., physiological measurements of the user), etc.

The process 600 includes constructing the displayable form (610a/610b). For example, the client device 104 may use the extracted contents of the data package 120 to determine how the module, or portions of the module, should be presented to the user. Constructing the form of the module may include, for example, determining an order for presenting different prompts of the module, or an order for presenting different sections for the module. Similarly, constructing the displayable form may include determining one or more prompts of the module that do not need to be presented to a user, or sections of the module that do not need to be presented to the user. For example, if the client device 104 determines that it has sufficient sensor data to conclude that a user is not at risk of sleep condition, the client device 104 may determine that it does not need to present prompts in the sleep quality section of the module to the user.

In some cases, constructing the form of the question may be based on a user profile for a user that will take the assessment. For example, a user profile may indicate that a user has been previously diagnosed with depression. As such, the client device 104 may determine that it should present prompts corresponding to a mental health section of the module at the beginning of the module or at the end of the module, when the user is more likely to be paying attention.

The process 600 includes collecting inputs for the module (612a/612b). For example, the client device 104 may collect inputs from a user through an interface of the client device 104. The inputs may include numerical data, text data, and interface element selection. The inputs may, in some cases, include sensor data obtained using sensors of the client device 104 or from one or more other sensing devices, such as a fitness tracker or a smartwatch. As an example, the inputs may include participant reported outcomes from a clinical trial.

The inputs collected or the extent of the type of inputs collected may depend on whether a risk was previously detected. For example, additional data (e.g., one or more additional types of data) may be collected when a risk is detected. This may be to better monitor the risk during the presentation of the module, to assist in confirming that the user is at risk, to rule out the risk, to determine with sufficient likelihood that the user has a particular condition, or to rule out the user having a particular condition with sufficient likelihood.

As illustrated, if no risk was previously detected at the start of the module (e.g., risk of cardiovascular failure), then the data being collected includes data that indicates a duration and distance that the user walked, jogged, or ran (e.g., during the module, or during a portion of the module). Specifically, a prompt of the module may have tasked the user with walking, jogging, or running for a predetermined amount of time (or for the duration of all or part of the module). However, if a risk was previously detected at the start of the module, such as a risk of cardiovascular failure, then the data being collected includes data that indicates a heart rate of the user in addition to the duration and distance that the user walked, jogged, or ran (e.g., during the module, or during a portion of the module). This additional heart rate data may be used to, for example, confirm that the user is it at risk of having cardiovascular failure (e.g., at some point in the future, or now in the process of completing the module), and/or to more accurately monitor the user's cardiovascular health.

The process 600 optionally includes detecting a risk for the second time (614). Instead of being limited to only previously obtained data, detecting the risk here may be based on only the data collected during the module, or a combination of the data collected during the module and the previously obtained data. The risk may be the same as the previously detected risk or within the same category of risks. As an example, the previously obtained data may include a weight for a user that indicates that that they are obese. Based on this information, the server system 110 may have determined that the user was at a higher risk of cardiovascular failure. After collecting the duration data, the distance data, and the heart rate data from the user, the client device 104 and/or the server system 110 may determine (e.g., with greater confidence) that the user is at risk of cardiovascular failure. In some cases, the risk that is detected may be wholly different from the previously detected risk.

With the additional data collected during the module, the client device 104 or the server system 110 may be able to identify the risk(s) in more detail. As an example, with the additional heart rate data, the server system 110 may determine that the user is at risk of having a heart attack in the immediate future with sufficient likelihood if they continue to complete the module (e.g., continue to walk in accordance with the prompt(s) of the module).

Detecting the risk may include, for example, tracking a cumulative score for a portion of the module (e.g., a particular section of the module, a subset of prompts related to cardiovascular health or that are otherwise indicative of the user's cardiovascular health), and determining if the cumulative score meets a threshold score corresponding to the risk. For example, after responding to all cardiovascular health related prompts, if a cumulative score for those cardiovascular health related prompts does not meet a threshold score corresponding to a risk of cardiovascular failure, then the client device 104 or the server system 110 may determine that the user is at risk of cardiovascular failure.

The process 600 optionally includes stopping the module in response to detecting the risk for the second time (614). For example, if the client device 104 or the server system 110 determines that the user is at risk of having a heart attack in the immediate future with sufficient likelihood, then the client device 104 or the server system 110 may immediately stop the module. The client device 104 or the server system 110 may further generate and send notifications in response to detecting the risk. For example, based on the severity of the risk and/or the confidence in the risk (or confidence in the user having an underlying health condition), the client device 104 or the server system 110 may generate and send notifications to emergency services, and/or to a physician of the user.

As discussed above, the module may be stopped early for other reasons. For example, if the cumulative quality score for a portion of the module (e.g., a section of the module, or a threshold number of prompts) does not meet a threshold quality score, then the client device 104 or the server system 110 may end the module.

The process 600 optionally includes determining that the module is complete (616a). As an example, the module may be determined to be complete after the user has responded to all prompts in the module. Additionally or alternatively, the module may be determined to be complete after one or more score thresholds have been met. For example, the client device 104 shown in FIG. 1 may mark the module as complete once a score threshold corresponding to the end of the module met based on a tracked cumulative score for the module. Similarly, the module may be complete after the score threshold for each of the sections of the module are met, e.g., using corresponding section cumulative scores tracked by the client device 104.

In some cases, successful completion may depend on a variety of criteria being met. For example, the client device 104 or the server system 110 may determine that a user has successfully completed a module if they have responded to at least a threshold number of prompts and the corresponding responses had an average quality score above 0.8/1.0.

The process 600 optionally includes determining follow-up form fields (618). The follow-up form fields may correspond to the data that is recommended (e.g., by the client device 104 and/or the server system 110) to be collected from the user in the future, such as in a subsequent module. These fields can be used during the construction of a form of the same module or a different module that is to be sent and presented to the user at a future point in time. The follow-up form fields may be selected based on, for example, the data that has been previously collected from the user (e.g., in their user profile of the user profiles 434, and/or during the current module). For example, in generating a new module, the server system 110 may not include fields for entering data that is already available.

The follow-up form fields may additionally or alternatively be based on inability to determine a condition of the user or to confirm the condition of the user with sufficient likelihood. As an example, when no initial risk is detected for the user, if the duration and distance of walking each do not meet a particular threshold, the client device 104 or the server system 110 may determine that additional data concerning the user's stability and/or joint health should be collected during a subsequent module. That is, the duration and distance data may not be enough to conclude with sufficient likelihood that the user is at risk of having one or more joint health issues. Therefore, the client device 104 or the server system 110 may determine that the follow-up forms should include accelerometer data and/or GPS data, and a subsequent module should include prompts that are designed to illicit data that is relevant to the joint health of the user (e.g., walking tasks, jumping tasks, one-leg standing tasks, etc.).

As illustrated, the follow-up form fields may include PRO and heart rate. As such, a subsequent module may provide for the collection of PRO and heart rate data, e.g., in order to identify a particular cardiovascular condition that the user is suffering from or to rule out one or more cardiovascular conditions.

The process 600 includes scoring the outcomes of the module (620). With respect to FIG. 1, the client device 104 may compare the inputs and/or the determined scores to condition criteria. For example, the client device 104 may compare the cumulative score for a cardiovascular section of the module to a threshold score that corresponds to a risk of the user having high blood pressure. If, for example, the cumulative score does not meet the threshold score, the client device 104 may conclude the user is at risk of having high blood pressure. The client device 104 may additionally or alternatively use sensor data and/or the particular responses to come to the conclusion that the user is at risk of having high blood pressure. For example, the client device 104 may use sensor data to increase the confidence in its conclusion (or to revoke its conclusion) that the user is at risk of having high blood pressure.

As illustrated, a score may be generated for the distance that the user walked (e.g., during the module in accordance with prompts of the module), the user's heart rate, and the user's weight. The client device 104 or the server system 110 may determine a distance score based on, for example, comparing the distance the user walked with a typical distance. The typical distance may be the average distance that other users (e.g., other healthy users) travelled when completing the module or a similar module, or when walking for a similar duration. For example, the client device 104 may determine a perfect score for distance if the user's distance meets or exceeds the typical distance. However, a lower score may be determined if the user's distance does not meet typical distance is not met. For example, if the user's distance is 80% below the typical distance, a score of 0.2 (e.g., out of a maximum score of 1.0) may be determined for the distance.

Determining the heart rate risk may include comparing a cumulative score for heart rate related prompts (e.g., prompts that collected heart rate sensor data and/or asked the user to input their heart rate) to one or more threshold scores. For example, if the cumulative score does not meet a first threshold, then the server system 110 may determine that there is a severe heart rate risk. Based on this, the server system 110 may, for example, contact emergency services. If the cumulative score meets the first threshold but not a second threshold, then the server system 110 may determine that there is a moderate heart rate risk. Based on this, the servers system 110 may generate and send a notification to a physician of the user, and/or to a researcher that is conducting a study that the user is a participant of. Finally, if the cumulative score meets the first and second threshold but not a third threshold, then the server system 110 may determine that there is a slight heart rate risk. Based on this, the server system 110 may generate and send a notification to the client device of the user indicating that a risk has been detected, and/or may recommend that a subsequent module for the user include additional prompts related to heart rate data.

Determining a weight risk may be similar to determining heart rate risk in the example above. In addition to using the weight of the user, the server system 110 (or the client device 104) may also use other information to determine if the user's weight risk. For example, one or more prompts of the module may provide for eliciting a height of the user, a body mass index of the user, a fat percentage of the user, etc. In scoring a weight of the user, one or more thresholds may be used that are adjusted based on the height and/or fat percentage of a user. For example, a first weight threshold corresponding to obesity (or otherwise unhealthy weight) may be set to 230 lb for a person that is 6' tall and has a body fat percentage of 25% or greater. However, if it is determined that the user is 5' 10" and has a body fat percentage of 30%, then the threshold weight may be lowered to 210 lb to account for the user's physiological measurements. The server system 110 may also use information that indicates how well the user is able to get around, e.g., walking speed, stair climbing speed, stability, etc. That is, in determining a weight risk, the server system 110 may take into account the user's ability to physically manage their weight/the extent to which their weight is disabling.

The process 600 includes reporting the outcomes of the module (622). The outcomes of the module may be reported to the user taking the module. For example, after completing the module, the client device 104 may display a notification indicating that the user is at risk of high blood pressure and should consult a cardiologist. The outcomes may also be reported to researchers, such as those conducting a clinical trial that the user is a participant in. Where the outcomes of the module include a determination with a sufficient confidence that the user is at risk of a serious health condition or has a serious health condition, the outcomes may be reported directly to a physician or to emergency services. For example, the outcomes may be sent to the server system 110 for storage on the data store 112. The server system 110 may proceed to contact a physician for the user and/or emergency services.

The process 600 optionally includes reporting that the module is complete (624). For example, the client device may display a notification on the interface 122 indicating the user has successfully completed the module. The client device 104 may send an indication that the user has successfully completed the module to the server system 110. In response, the server system 110 may update a user profile of the user to include the indication (and/or the responses provided by the user, or the corresponding scores), and may send the indication to researcher conducting a study that the user is a participant of.

The process 600 optionally includes reporting a next module recommendation (626). For example, if the outcomes indicate that the user is potentially at risk of a medical condition, the client device 104 (or the server system 110) may recommend that the user complete another module related to the medical condition. Similarly, if the outcomes of the module indicate that more information is required to make a determination as to whether the user is at risk of a medical condition or has a medical condition, the client device 104 (or the server system 110) may recommend that the user completes a module containing prompts that will elicit the data required to make those determinations.

The next module recommendation may include prompts that contain and/or elicit data related to the follow-up form fields.

The process 600 includes delivering module results (628). Delivering module results may include determining one or more parties that are to be notified, generating a notification, and sending the notification to corresponding devices of the selected parties. The parties select may depend on whether any risks were detected during the module, and/or on the outcome of the results. For example, the server system 110 may generate a notification to send to a client device of the user and to a device of a researcher of a study that the user is participant of when the user successfully completes the module, or fails the module. In the event that a risk is detected, the server system 110 may generate and send a notification that includes an indication of the risk to the researcher, to a physician of the user, and/or to emergency services depending on the confidence in the risk and/or the severity of the underlying condition (e.g., emergency services may be contacted when there is sufficiently high risk that the user is about to experience a heart attack, but only the user's physician if it is determined that the user is at risk of high blood pressure).

In generating a notification, the server system 110 (or the client device 104) may select one or more predetermined messages. For example, there may be a predetermined message for notifying the user that they have successfully completed the module, and/or if they failed the module. There may be similar predetermined messages for researchers.

In generating a notification, the server system 110 (or the client device 104) may select one or more predetermined messages that include fields to be filled in. For example, in generating a message to the researcher regarding a risk of a health condition, the server system 110 may select a predetermined message that is specific to notifying researchers of a detected health risk. The predetermined message may include a first field that corresponds to the health risk detected, and a second field that corresponds to the confidence in the user being at risk and/or having the underlying health condition.

In generating a notification, the server system 110 (or the client device 104) may use predetermined phrases along with determinations made (e.g., by the evaluation module 470) to generate a notification. For example, to generate a notification for a researcher, the server system 110 may retrieve a subset of phrases that are frequently used when reporting module outcomes to researchers. The server system 110 may appropriately arrange these phrases, and combine them with information collected during the module and/or determinations made during the module to generate the notification.

The table below illustrates example input data and corresponding collection parameters and scoring parameters. The collection parameters may provide various criteria for determining the validity of the input data, and/or requirements for the type of data collected. For example, the collection parameters may provide that the weight of the user is only valid if it has been taken within the past month. As shown, the scoring parameters may be specific to the type of input data collected, and may outline how a module (or portion of a module) is scored and/or passed. For example, a participant will only be determined to have completed the test if the total time to complete the test was six minutes or less.

TABLE 2

| Input Data | Collection Parameters | Scoring Parameters |
| --- | --- | --- |
| Participant Reported Outcome (PRO) | Fatigue and Dyspnea Measures Before and After the Test Length Time | Reporting Scale - e.g. Borg Scale |
| Test Length | Time Specified (e.g. 6 minutes) | Anything outside of 6 min is considered incomplete |
| Weight | Within the last month | Informative Only |
| Distance | During the Test Length Time | Distance is within a community average, or personal average |
| Heart Rate | Before and After the Test Length Time | Informative Only |
| Schedule | Once a year, No more than once a day | Once successfully completed, individual cannot complete again until the next day After one year of a successful completion, a notification can be sent to the individual to complete |

The information in Table 2 may be used in the process 600. For example, the client device 104 (or the server system 110) may use parameters as described in column 2 (Collection Parameters) to determine, for example, if the data collected (e.g., the responses, sensor data, electronic medical records, etc.) during presentation of the module is valid. Finally, if the responses are valid, the client device 104 or the server system 110 may use parameters as described in column 3 (Scoring Parameters) to determine one or more scores corresponding to the particular prompt and/or to determine if the user has successfully completed the module. These one or more scores may be a score that indicative of the user's traits, such as their physiological health. Similarly, these one more scores may include a quality score that indicates the quality of data collected (e.g., the trustworthiness of the user's responses based on their previous responses, past responses, response time, etc.).

Figure 7:
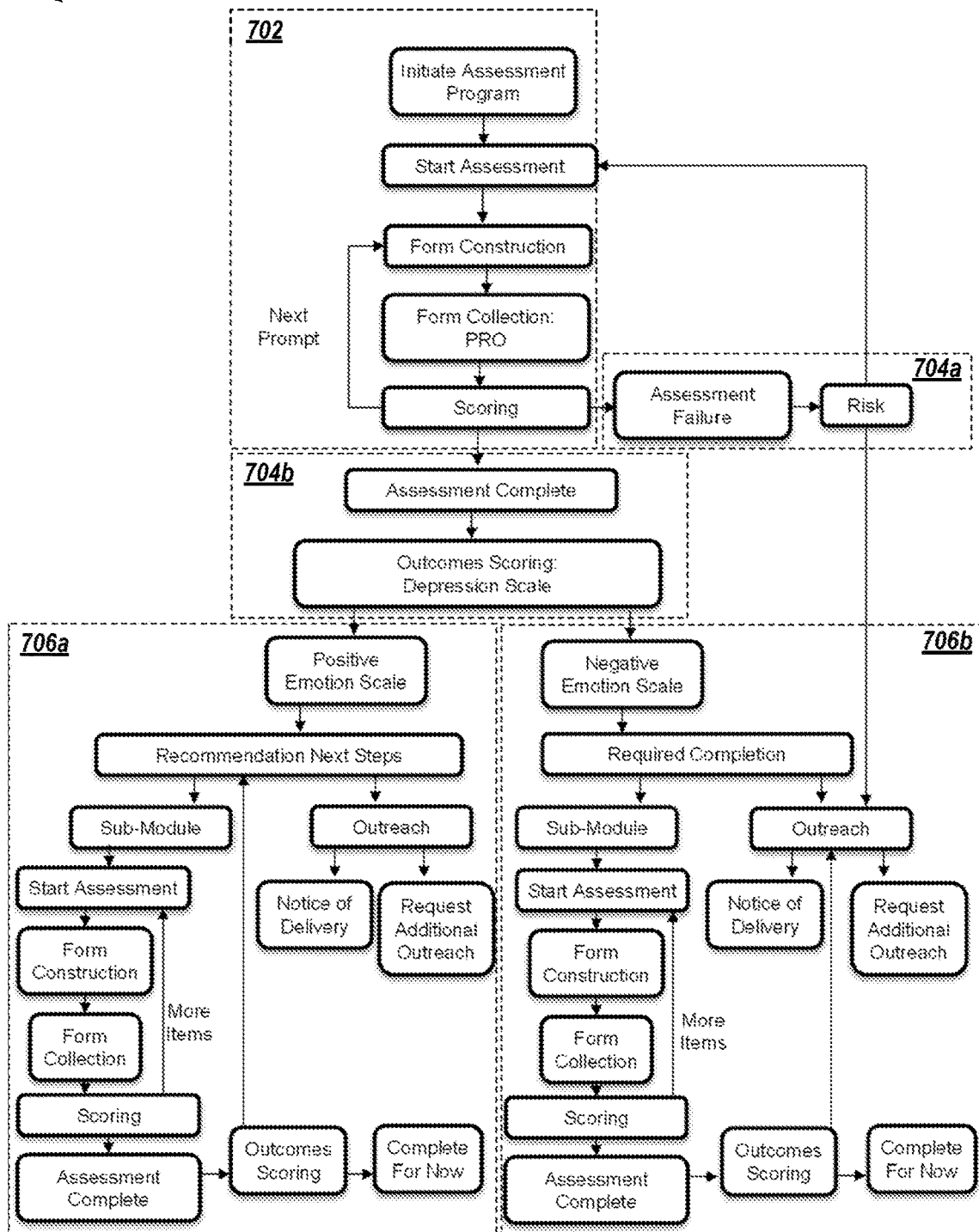

FIG. 7 is a flowchart diagram that illustrates an example process 700 for conducting a module. The process 700 may be performed in whole or in part by the server system 110 shown in FIG. 1 and FIGS. 4A-4B, the client device 104 shown in FIG. 1, and/or the client device 454 shown in FIG. 4B.

As an example, the process 700 illustrates conducting a module that collects data related to the user's mental health. For example, the module may include a mental health or depression section, or may be entirely focused on the user's mental health. The example describes the ability of the system to perform a baseline measure, assess risk, and then, depending on the measure, provide a recommendation or opportunities for positive outcome intervention delivery. Table 3 below describes inputs related to a module that specifies an EMI for assisting in positive outcome measures related to an observed mental measure.

The process 700 is divided into multiple sections. These sections include a first section 702 for initiating the module and conducting the module, a second optional section 704a for completing the module and scoring the outcomes of the module, a third optional section 704b for determining that the module has failed, a fourth optional section 706a that corresponds to a positive emotion scale, and a fifth optional section 706b that corresponds to a negative emotion scale.

The first section 702 can include initiating a module program. For example, with respect to FIG. 1, the client device 104 may run a mobile application for conducting modules in response to receiving the form data package 120 from the server system 110. As another example, the participant 102 may initiate a module program by opening a mobile application for conducting modules.

The first section 702 can include starting a module. For example, with respect to FIG. 1, the client device 104 may start a module by extracting the contents of the form data package 120. Alternatively, the client device 104 may start the module 104 by presenting a portion of the module on an interface of the client device 104, such as predetermined first prompt of the module.

The first section 702 can include constructing the form of the module. For example, the client device 104 may use the extracted contents of the data package 120 to determine how the module, or portions of the module should be presented to the user. Constructing the form of the module may include, for example, determining an order for presenting different prompts of the module, or an order for presenting different sections for the module. Similarly, constructing the form of the module may include determining one or more prompts of the module that do not need to be presented to a user, or sections of the module that do not need to be presented to the user. For example, if the client device 104 determines that it has sufficient sensor data to conclude that a user is not at risk of sleep condition, the client device 104 may determine that it does not need to present prompts in the sleep quality section of the module to the user.

In some cases, constructing the form of the question may be based on a user profile for a user that will take the module. For example, a user profile may indicate that a user has been previously diagnosed with depression. As such, the client device 104 may determine that it should presents prompts corresponding to a mental health section of the module at the beginning of the module or at the end of the module, when the user is more likely to be paying attention.

The first section 702 can include collecting inputs for the module. For example, the client device 104 may collect inputs from a user through an interface of the client device 104. The inputs may include numerical data, text data, and interface element selection. The inputs may, in some cases, include sensor data obtained using sensors of the client device 104 or from one or more other sensing devices, such as a fitness tracker or a smartwatch. As an example, the inputs may include participant reported outcomes from a clinical trial.

The first section 702 can include scoring at least a portion of the module. For example, the client device 104 may use one or more scoring parameters from the form data package to determine a score for the first prompt of the module. The client device 104 may compare the user's response to the first prompt to the scoring parameters to determine a score. In some cases, if the user's response does not meet the collection parameters, the client device 104 may determine a score of zero for the first prompt. Alternatively, the client device 104 may ask the user to review their response and resubmit.

The scoring parameters may be used to generate a score that indicative of the participant's traits, such as their physiological health. The scoring parameters may additionally or alternatively provide for generating a quality score that indicates the trustworthiness and/or validity of the data collected.

After a prompt is scored (e.g., by the client device 104 or the server system 110), the client device 104 may again perform form construction by selecting a new prompt to present to the user and/or a new section of the module to have the user start.

Scoring at least a portion of the module may include tracking one or more cumulative scores. For example, the client device may track a cumulative score for the entire module, and then cumulative scores for each section of the module. The client device 104 may compare these cumulative scores to corresponding scoring parameters to determine one or more actions to perform, such as switching sections of the module or determining that the module is complete.

The optional second section 704a includes determining that the module has failed. A module may be determined to fail if, for example, it is determined that a user's responses are unreliable. For example, if the response time for the user's inputs consistently does not meet a minimum response time, or if the user's inputs are the same for a threshold number of inputs (e.g., same response of choice A was provided for the last five questions, or the same response of choice A was provided for the last five questions within the last ten seconds). Similarly, a user's inputs may otherwise be determined to be unreliable and, therefore, a reason for determining that the module has failed. For example, the client device 104 may determine that the user's inputs are unreliable if the user's inputs are consistently shown to be incorrect when compared to collected sensor data.

In some cases, determining that the module has failed may include determining that one or more score thresholds have not been met after all or subset of prompts have been responded to. For example, if a score threshold (e.g., a quality score threshold) for completing the module is not met after the client device 104 has presented all prompts of the module to the user and the corresponding responses have been scored, the client device 104 may determine that the module has failed. Not meeting a threshold may correspond to a risk, such as a risk of a particular health condition. For example, if the cumulative score for mental health related prompts does not meet a threshold score, the server system 110 (or the client device 104) may determine that the user is at risk of depression.

In response to determining that the module has failed, the client device may request that the user retake the module. The form of the module or for a particular portion of the module, such as a particular section, may be modified in an effort to get the user to successfully complete the module. Alternatively, the client device 104 may recommend an alternate module for the user to take.

In some cases, failure may occur when particular patterns and/or events are detected. For example, if the user fails to meet a minimum response time for eight questions in a row, the client device 104 may end the module and determine that the user has failed the module.

The optional second section 704a can include detecting one or more risks associated with the user. The risks may include a risk of the user having a particular health condition, including mental health conditions. The server system 110 (or the client device 104) may detect a risk using, for example, scores determined for particular prompts, and/or cumulative scores. For example, if the cumulative score for mental health related prompts does not meet a threshold score, the server system 110 (or the client device 104) may determine that the user is at risk of depression. The risks may include a risk that requires immediate attention. For example, based on the user's responses to one or more prompts, it may be determined that the user is at risk of committing suicide. In response, the server system 110 (or the client device 104) may notify emergency services, and/or an emergency contact for the user.

The optional third section 704b includes determining that the module is complete. As an example, the module may be determined to be complete after the user has responded to all prompts in the module. Additionally or alternatively, the module may be determined to be complete after one or more score thresholds have been met. For example, the client device 104 shown in FIG. 1 may mark the module as complete once a score threshold corresponding to the end of the module met based on a tracked cumulative score for the module. Similarly, the module may be complete after the score threshold for each of the sections of the module are met, e.g., using corresponding section cumulative scores tracked by the client device 104.

In some cases, successful completion may depend on a variety of criteria being met. For example, the client device 104 or the server system 110 may determine that a user has successfully completed a module if they have responded to at least a threshold number of prompts and the corresponding responses had an average quality score above 0.8/1.0.

The optional third section 704b includes scoring the outcomes of the module. With respect to FIG. 1, the client device 104 may compare the inputs and/or the determined scores to condition criteria. For example, the client device 104 may compare the cumulative score for a cardiovascular section of the module to a threshold score that corresponds to a risk of the user having high blood pressure. If, for example, the cumulative score does not meet the threshold score, the client device 104 may conclude the user is at risk of having high blood pressure. The client device 104 may additionally or alternatively use sensor data and/or the particular responses to come to the conclusion that the user is at risk of having high blood pressure. For example, the client device 104 may use sensor data to increase the confidence in its conclusion (or to revoke its conclusion) that the user is at risk of having high blood pressure.

Where the module is related to mental health (e.g., depression), scoring the outcomes of the module may include determining whether further analysis of the user is required with respect to a positive emotion scale or a negative emotion scale. For example, if a cumulative score corresponding to mental health related prompts of the module does not meet a first threshold score, the server system 110 (or the client device 104) may determine that further analysis of the user is needed with respect to a negative emotion scale (e.g., user is determined to be sad and there is a high risk of the user suffering from depression). Similarly, if the cumulative score does meet the threshold score, the server system 110 (or the client device 104) may determine that further analysis of the user is needed with respect to a positive emotion scale (e.g., user is determined to be happy and is there is only a slight risk of the user suffering from depression).

The optional fourth section 706a includes using the scoring outcomes to determine that further analysis of the user is needed with respect to a positive emotion scale. As an example, the server system 110 (or the client device 104) may use the user's responses during the module to determine where the user falls along a positive emotion scale (e.g., okay, calm, pleased, thrilled, elated, etc.). Specifically, each emotion in the scale may have a corresponding threshold score range, such that it can be compared with a cumulative score for mental health related prompts of the module. For example, if the cumulative score is 7.2 and a threshold score range for the "pleased" emotion is between 6.7 and 8, then the server system 110 may determine that the user is pleased.

Due to the low risk of the user suffering from a particular health condition (e.g., depression), the optional fourth section 706a may include determining recommended next steps for the user to take. These next steps may include taking one or more additional modules (e.g., that are specifically focused on depression), and/or participating in a form of outreach (e.g., scheduled calls with mental health professionals, group meetings and/or events, etc.). The recommended next steps may be based on the detected emotion for the user along the positive emotion scale. For example, the sever system 110 may not recommend any outreach if the user is elated. However, the server system 110 may recommend that the user take another module (e.g., potentially the same module) within a week to ensure that the user is consistently being evaluated with respect to the positive emotion scale.

In some cases, the recommended next steps are selected by the server system 110 (or the client device 104). The server system 110 may implement the recommended next steps without confirmation by, for example, notifying the user of the recommended next steps. Alternatively, the recommended next steps may be first recommended to a physician of the user and/or a researcher/admin. The physician and/or researcher/admin may be able to confirm the recommendations, and/or to adjust the recommendations.

The optional fifth section 706b includes using the scoring outcomes to determine that further analysis of the user is needed with respect to a negative emotion scale. As an example, the server system 110 (or the client device 104) may use the user's responses during the module to determine where the user falls along a negative emotion scale (e.g., disappointed, annoyed, upset, angry, furious, etc.). Specifically, each emotion in the scale may have a corresponding threshold score range, such that it can be compared with a cumulative score for mental health related prompts of the module. For example, if the cumulative score is 2.2 and a threshold score range for the "angry" emotion is between 1.5 and 2.5, then the server system 110 may determine that the user is angry.

Due to the higher risk of the user suffering from a particular health condition (e.g., depression), the optional fifth section 706b may include determining required next steps for the user to take. These next steps may include assigning the user one or more additional modules (e.g., that are specifically focused on depression), and/or tasking the use with participating in a form of outreach (e.g., scheduled calls with mental health professionals, group meetings and/or events, etc.). These next steps may be required due to the heightened risk of the user suffering from depression or another mental ailment. The required next steps may be based on the detected emotion for the user along the negative emotion scale. For example, the sever system 110 may require the user to attend weekly group meetings if they are determined to be angry or furious, in addition to weekly calls with a healthcare professional. However, the server system 110 may only schedule monthly calls with a healthcare professional if the user is disappointed, and will not require weekly group meetings.

In some cases, the required next steps are selected by the server system 110 (or the client device 104). The server system 110 may implement the required next steps without confirmation by, for example, notifying the user of the required next steps and/or scheduling outreach for the user. Alternatively, the required next steps may be first recommended to a physician of the user and/or a researcher. The physician and/or researcher may be able to confirm the recommendations, and/or to adjust the recommendations.

The table below illustrates example input data and corresponding collection parameters and scoring parameters. The collection parameters may provide various criteria for determining the validity of the input data, and/or requirements for the type of data collected. For example, the collection parameters may provide that the total time to take the module is no more than two hours. As shown, the scoring parameters may be specific to the type of input data collected, and may outline how a module (or portion of a module) is scored and/or passed. The scoring parameters may also indicate one or more actions that should be taken in response to particular conditions being detected (e.g., where the conditions may be based on determined scores). For example, the scoring parameters may provide that a positive emotion response (e.g., based on a cumulative score for prompts related to mental health and/or more specifically to emotion response evaluation) will result in an optional sub-module selection and outreach (e.g., instead of required sub-module and/or outreach).

TABLE 3

| Input Data | Collection Parameters | Scoring Parameters |
|---|---|---|
| Participant Reported Outcome (PRO) | PHQ-9 | Positive emotion response results in optional sub-module selection and outreach<br>Negative emotion response results in required sub-module and/or outreach |
| Test Length | Within 2-hour time period | Ignored or unreported attempts result in outreach after 1 day |
| Schedule | At least 3 times a day within +/−2 hours at 6am, 12pm, and 6pm, no limit on number of entries | Regular reminders based on schedule and other triggers.<br>Schedule will occur every hour until successful response, and then at 6am, 12pm, and 6pm unless response was recently collected within 2 hours prior to scheduled update |
| Supplement Test Kit | Sleep and Stress Test Collected once | Suggested based on sleep score data |
| Sub-Modules | Mental break Individual finds a quiet space for 2 minutes to meditate and breath | No activity for 2 minutes, passive sensing determines ambient audio levels, app usage and movement |
| | Diet and Exercise Individual walks or works out within the next hour for at least 5 min or more | Detects movement and motion consistent with workout or heart rate data consistent with workout |
| | Sleep Adjustment Individual is requested to sleep at a specified time and wake at a specified time | Alarms are set using the phone to reminder sleep time adjustment and to help wake the individual |
| | CBT Sessions Individual receives 10 course to take in a 4-week time period | Additional content is shown for the next course including video, reading materials and knowledge checks |
| Outreach | Support Group | Push notifications are sent to a group, a hotline or a predetermined contact In case this is not successful, then participant is asked to call a contact until a phone call is made and registered |

Table 3 describes an example of parameters that can be used in the process 700. For example, the client device 104 (or the server system 110) may use parameters as described in column 2 (Collection Parameters) during the collection of form data during the first section 702 to determine if the collected data is valid, and use parameters as described in column 3 (Scoring Parameters) during the scoring of the collected data during the first section 702 to determine score(s) for the collected data and/or determining if the module is complete in the optional third section 704b.

Moreover, the server system 110 may refer to the "sub-modules" input data and the corresponding parameters in the optional fourth section 706a or the optional section 706b of the process 700. For example, the server system 110 may refer to the "sub-modules" input data when determining the recommended next steps in the optional fourth section 706a and when constructing a form of a subsequent module.

A number of implementations have been described. Nevertheless, it will be understood that various modifications may be made without departing from the spirit and scope of the disclosure. For example, various forms of the flows shown above may be used, with steps re-ordered, added, or removed.

In the claims, the term "or" is generally intended to be inclusive, not exclusive. For example, the phrase "A or B" should be interpreted as encompassing (1) A only, (2) B only, and (3) A and B together. Thus, absent any modifying word or phrase to specify exclusivity (e.g., "either A or B" or "only one of A or B"), listed items are not mutually exclusive.

Embodiments of the invention and all of the functional operations described in this specification can be implemented in digital electronic circuitry, or in computer software, firmware, or hardware, including the structures disclosed in this specification and their structural equivalents, or in combinations of one or more of them. Embodiments of the invention can be implemented as one or more computer program products, e.g., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the invention can be implemented on a computer having a display device, e.g., a cathode ray tube or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the invention, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Particular embodiments of the invention have been described. Other embodiments are within the scope of the following claims. For example, the steps recited in the claims can be performed in a different order and still achieve desirable results.

What is claimed is:

1. A method performed by one or more computers, the method comprising:
    identifying, by the one or more computers, a selected form module with which to provide a form at a user device, wherein the form module has been selected from among a plurality of form modules, wherein each of the form modules includes (i) a set of form elements, (ii) scoring parameters for evaluating responses to the respective form elements of the form module, and (iii) data collection parameters for collecting data using the elements of the form module;
    obtaining, by the one or more computers, the data collection parameters from the selected form module, wherein the data collection parameters indicate a timing or frequency for collecting input through the form by the user device;
    obtaining, by the one or more computers, the scoring parameters from the selected form module, wherein the scoring parameters specify criteria for generating scores for responses to the form elements of the selected form module;
    generating, by the one or more computers, one or more scores for the form based on responses to at least some of the form elements of the selected form module, wherein the responses are collected according to the data collection parameters of the selected form module, and wherein the one or more scores are determined based on the scoring parameters; and based on an evaluation of the generated one or more scores, providing, by the one or more computers, at least one of (i) an additional form to present at the user device, (ii) an interactive module configured to prompt a user for input, or (iii) data indicating a completion event for a session at the user device.

2. The method of claim 1, comprising:

determining a set of data elements to be collected through presentation of the form based on the selected form module; and providing form data to the user device over a network, the form data enabling the user device to present a form configured to collect the determined set of data elements.

3. The method of claim 1, wherein the data collection parameters specify a range of time that a collected data item is valid; and wherein the method comprises:
determining that a data item associated with the user device was previously collected within the range of time specified by the data collection parameters; and
omitting from presentation one or more form elements configured to collect the data item.

4. The method of claim 1, comprising:
determining that a data item corresponding to a particular form element can be collected using a sensor of the user device or another device in communication with the user device;
collecting the data item using the sensor of the user device or the other device; and
omitting the particular form element from presentation.

5. The method of claim 1, wherein one or more of the form elements prompt for input of data that is dependent on a current context of the user device or a user of the user device.

6. The method of claim 1, wherein one or more of the form elements prompt for input describing a current experience, current behavior, or current mood of a user of the user device.

7. The method of claim 1, wherein the collection parameters specify at least one of:
a type of data to be collected through the form;
a maximum response time for a form element;
a maximum response time for the form as a whole;
an order of presentation of the form elements;
a frequency with which to present the form;
an activity for a user to perform;
characteristics of responses to measure for one or more form elements;
a validity period for prior data collected; or
an alternative source of data for one or more form elements.

8. The method of claim 1, wherein the scoring parameters specify at least one of:
criteria for assessing validity of responses;
criteria for assessing validity of input patterns;
a threshold or reference for comparison with generated scores for the form;
data specifying conditions for achieving a goal or purpose of the form; or
criteria for determining when to end a session of interaction with a user.

9. The method of claim 1, wherein the scoring parameters indicate a threshold score that, when reached, indicates that (i) a presentation of a form based on the selected form module is complete or (ii) that a section of the module is complete.

10. The method of claim 1, wherein the scoring parameters include one or more rules or equations for deriving scores from responses to the elements of the selected form module.

11. The method of claim 1, wherein the scoring parameters indicate (i) different scoring techniques for generating scores for responses to different elements of the selected form module, and (ii) one or more thresholds, wherein the selected form module is configured to cause a change in the presentation of the form module when the generated one or more scores for the form satisfy the one or more thresholds.

12. A system comprising:
one or more computers; and
one or more computer-readable media storing instructions that are operable, when executed by the one or more computers, to cause the one or more computers to perform operations comprising:
identifying, by the one or more computers, a selected form module with which to provide a form at a user device, wherein the form module has been selected from among a plurality of form modules, wherein each of the form modules includes (i) a set of form elements, (ii) scoring parameters for evaluating responses to the respective form elements of the form module, and (iii) data collection parameters for collecting data using the elements of the form module;
obtaining, by the one or more computers, the data collection parameters from the selected form module, wherein the data collection parameters indicate a timing or frequency for collecting input through the form by the user device;
obtaining, by the one or more computers, the scoring parameters from the selected form module, wherein the scoring parameters specify criteria for generating scores for responses to the form elements of the selected form module;
generating, by the one or more computers, one or more scores for the form based on responses to at least some of the form elements of the selected form module, wherein the responses are collected according to the data collection parameters of the selected form module, and wherein the one or more scores are determined based on the scoring parameters; and
based on an evaluation of the generated one or more scores, providing, by the one or more computers, at least one of (i) an additional form to present at the user device, (ii) an interactive module configured to prompt a user for input or (iii) data indicating a completion event for a session at the user device.

13. The system of claim 12, wherein the operations comprise:
determining a set of data elements to be collected through presentation of the form based on the selected form module; and
providing form data to the user device over a network, the form data enabling the user device to present a form configured to collect the determined set of data elements.

14. The system of claim 12, wherein the data collection parameters specify a range of time that a collected data item is valid; and
wherein the operations comprise:

determining that a data item associated with the user device was previously collected within the range of time specified by the data collection parameters; and omitting from presentation one or more form elements configured to collect the data item.

15. The system of claim 12, wherein the operations comprise:

determining that a data item corresponding to a particular form element can be collected using a sensor of the user device or another device in communication with the user device;

collecting the data item using the sensor of the user device or the other device; and omitting the particular form element from presentation.

16. The system of claim 12, wherein one or more of the form elements prompt for input of data that is dependent on a current context of the user device or a user of the user device.

17. The system of claim 12, wherein one or more of the form elements prompt for input describing a current experience, current behavior, or current mood of a user of the user device.

18. The system of claim 12, wherein the collection parameters specify at least one of:

a type of data to be collected through the form;
a maximum response time for a form element;
a maximum response time for the form as a whole;
an order of presentation of the form elements;
a frequency with which to present the form;
an activity for a user to perform;
characteristics of responses to measure for one or more form elements;
a validity period for prior data collected; or
an alternative source of data for one or more form elements.

19. The system of claim 12, wherein the scoring parameters specify at least one of:

criteria for assessing validity of responses;
criteria for assessing validity of input patterns;
a threshold or reference for comparison with generated scores for the form;
data specifying conditions for achieving a goal or purpose of the form; or
criteria for determining when to end a session of interaction with a user.

20. One or more non-transitory computer-readable media storing instructions that are operable, when executed by one or more computers, to cause the one or more computers to perform operations comprising:

identifying, by the one or more computers, a selected form module with which to provide a form at a user device, wherein the form module has been selected from among a plurality of form modules, wherein each of the form modules includes (i) a set of form elements, (ii) scoring parameters for evaluating responses to the respective form elements of the form module, and (iii) data collection parameters for collecting data using the elements of the form module;

obtaining, by the one or more computers, the data collection parameters from the selected form module, wherein the data collection parameters indicate a timing or frequency for collecting input through the form by the user device;

obtaining, by the one or more computers, the scoring parameters from the selected form module, wherein the scoring parameters specify criteria for generating scores for responses to the form elements of the selected form module;

generating, by the one or more computers, one or more scores for the form based on responses to at least some of the form elements of the selected form module, wherein the responses are collected according to the data collection parameters of the selected form module, and wherein the one or more scores are determined based on the scoring parameters; and based on an evaluation of the generated one or more scores, providing, by the one or more computers, at least one of (i) an additional form to present at the user device, (ii) an interactive module configured to prompt a user for input, or (iii) data indicating a completion event for a session at the user device.

* * * * *